United States Patent
Lubelski et al.

(10) Patent No.: US 12,319,924 B2
(45) Date of Patent: Jun. 3, 2025

(54) LIVER-SPECIFIC VIRAL PROMOTERS AND METHODS OF USING THE SAME

(71) Applicant: uniQure IP B.V., Amsterdam (NL)

(72) Inventors: Jacek Lubelski, Amsterdam (NL); David Johannes Francois Du Plessis, Amsterdam (NL); Ying Pui Liu, Amsterdam (NL); Olivier Ter Brake, Amsterdam (NL); Juan Manuel Iglesias Gonzalez, Lothian (GB); Ross Fraser, Lothian (GB); Michael Roberts, Lothian (GB)

(73) Assignee: uniQure IP B.V., Amsterdam (NL)

( * ) Notice: Subject to any disclaimer, the term of this patent is extended or adjusted under 35 U.S.C. 154(b) by 1006 days.

(21) Appl. No.: 17/320,758

(22) Filed: May 14, 2021

(65) Prior Publication Data
US 2022/0073943 A1  Mar. 10, 2022

Related U.S. Application Data

(63) Continuation of application No. PCT/EP2019/081743, filed on Nov. 19, 2019.

(30) Foreign Application Priority Data

Nov. 19, 2018 (EP) .................... 18207027

(51) Int. Cl.
| | | |
|---|---|---|
| *C12N 15/85* | (2006.01) | |
| *A61P 1/16* | (2006.01) | |
| *C12N 15/86* | (2006.01) | |
| *A61K 48/00* | (2006.01) | |

(52) U.S. Cl.
CPC ................ *C12N 15/85* (2013.01); *A61P 1/16* (2018.01); *C12N 15/86* (2013.01); *A61K 48/00* (2013.01); *C12N 2750/14123* (2013.01); *C12N 2750/14143* (2013.01); *C12N 2750/14171* (2013.01); *C12N 2830/008* (2013.01)

(58) Field of Classification Search
CPC ............ C12N 15/85; C12N 15/86; A61P 1/16
See application file for complete search history.

(56) References Cited

FOREIGN PATENT DOCUMENTS

WO    WO-2016/168728 A2    10/2016

OTHER PUBLICATIONS

Marinee K Chuah et al: "Liver-Specific Transcriptional Modules Identified by Genome-Wide In Silico Analysis Enable Efficient Gene Therapy in Mice and Non-Human Primates", Molecular Therapy, vol. 22, No. 9, Sep. 1, 2014 (Sep. 1, 2014), pp. 1605-1613.
Nisha Nair et al: "Computationally designed liver-specific transcriptional modules and hyperactive factor IX improve hepatic gene therapy", Blood, May 15, 2014 (May 15, 2014), pp. 3195-3199.
International Search Report and Written Opinion of the International Searching Authority in PCT/EP2019/081743 mailed Apr. 1, 2020, 16 pages.

*Primary Examiner* — Evelyn Y Pyla
*Assistant Examiner* — Katherine R Small
(74) *Attorney, Agent, or Firm* — N.V. Nederlandsch Octrooibureau

(57) ABSTRACT

The present invention relates to promoters that function specifically or preferentially in the liver. These promoters are capable of enhancing liver-specific expression of genes. The invention also relates to expression constructs, vectors and cells comprising such liver-specific promoters, and to methods of their use. The present invention future relates to adeno-associated virus (AAV) gene therapy vectors comprising the liver-specific promoters, therapeutic agents comprising the liver-specific promoters, and methods using the same.

22 Claims, 32 Drawing Sheets
Specification includes a Sequence Listing.

Fig. 2

APOC2 (65 bp):

GAGCGGAAGTGGGTCTCAACCACTATATAAATCCCTCTGTGCCCGTCCGGAGCTGGTGAGGACAGC

SERPINE1 (65 bp) (p1@SERPINE1):

TCATCTATTTCCTGCCACATCTGGTATAAAAGGAGGCAGTGGCCCAAGAGGAGCACAGCTGTG

C6PC (70 bp):

GGGCATATAAACAGGGGCAAGGCACAGAGACTCATAGCAGAGCAATCACCACCAAGCCTGGAATAA
CTGCA

SERPINA1 (186 bp):

GGGCGACTCAGATCCAGCCAGTGGACTTAGCCCCCTGTTTGCTCCTCCGATAACTGGGGTGACCT
                                                                               p1@SERPINA1
TGGTTAATATTCACCAGCAGCCTCCCCGTTGCCCCTCTGGATCCACTGCTTAAATACGGACGAG
                                                                                **********
GACAGGGCCCTGTCTCCTCAGCTTCAGGCACCACCACTGACCTGGGACAGTGAATG

Fig. 8A
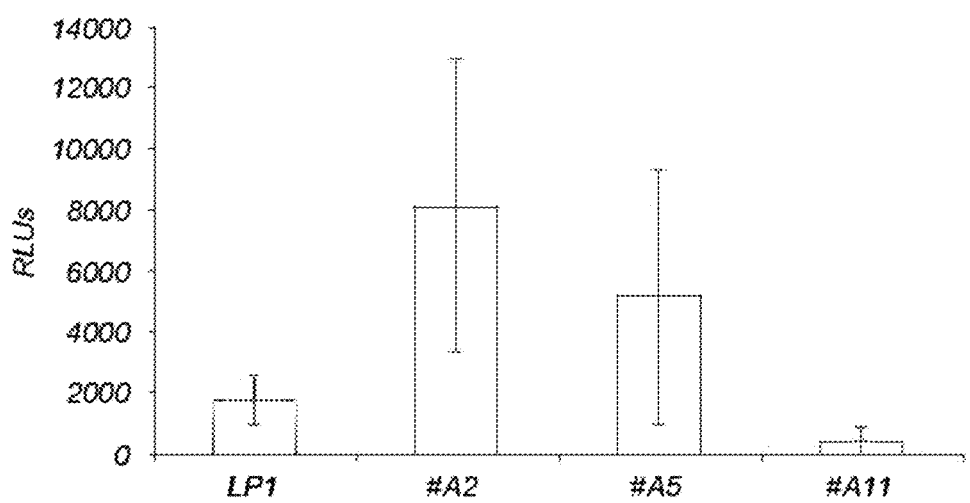
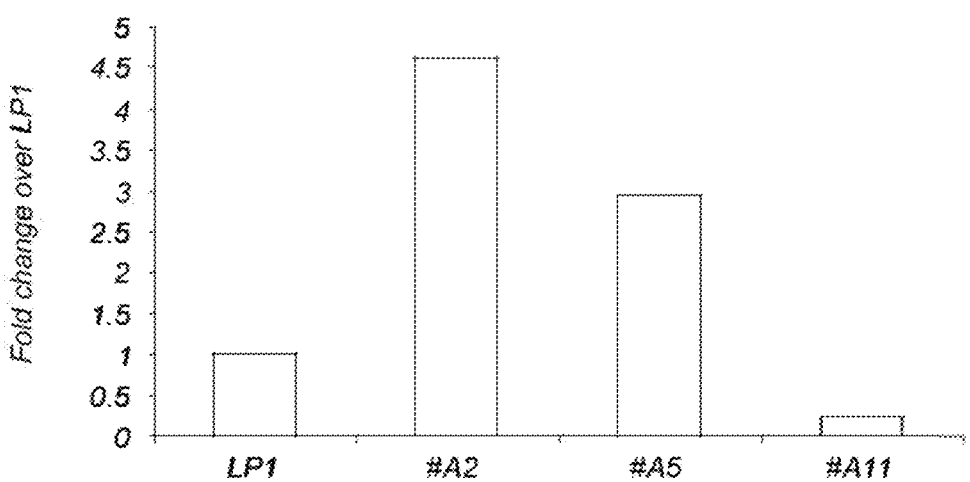
Fig. 8B

Fig. 10A
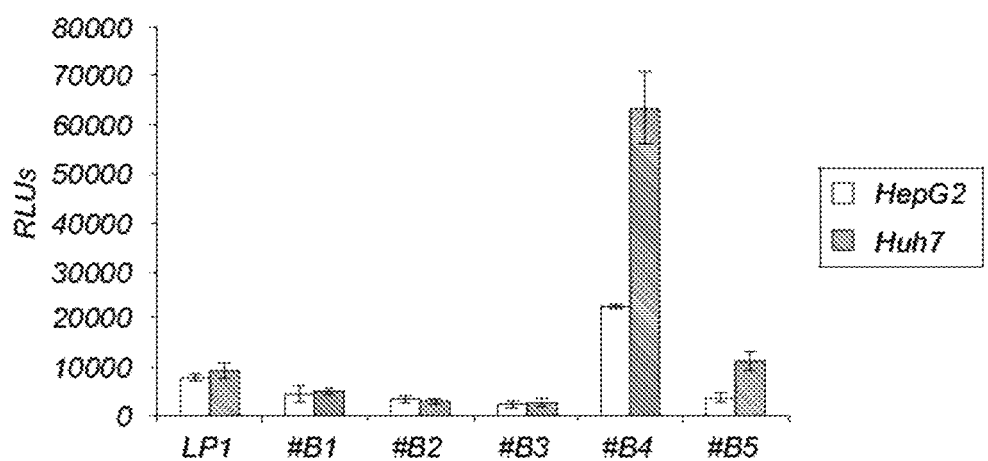
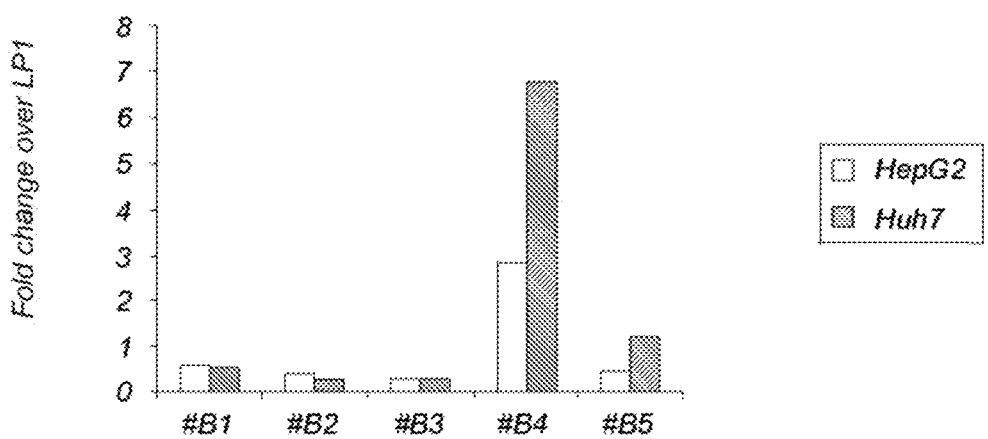
Fig. 10B

Fig. 11A
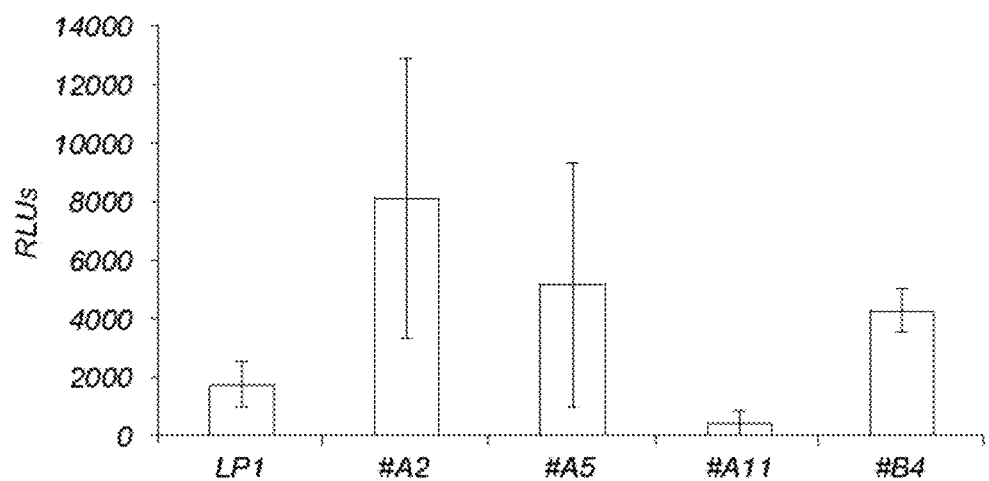
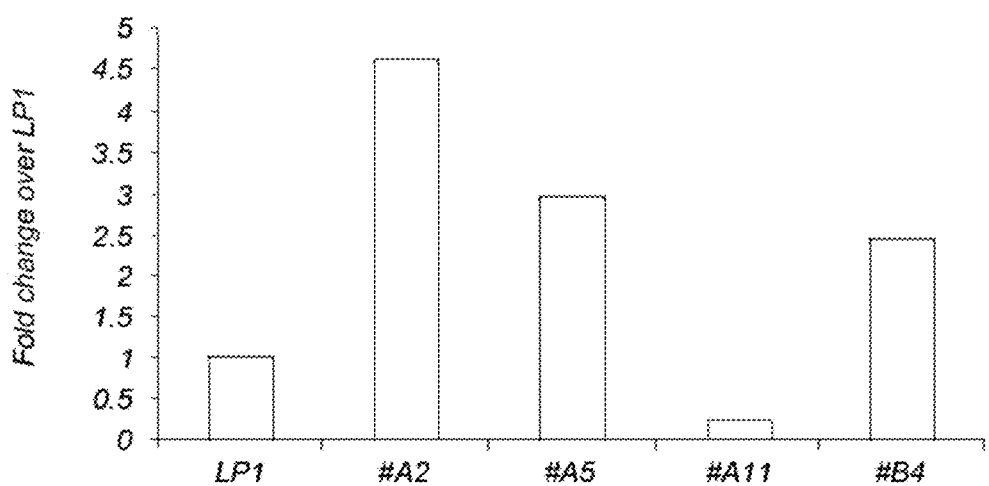
Fig. 11B

FIG. 13A
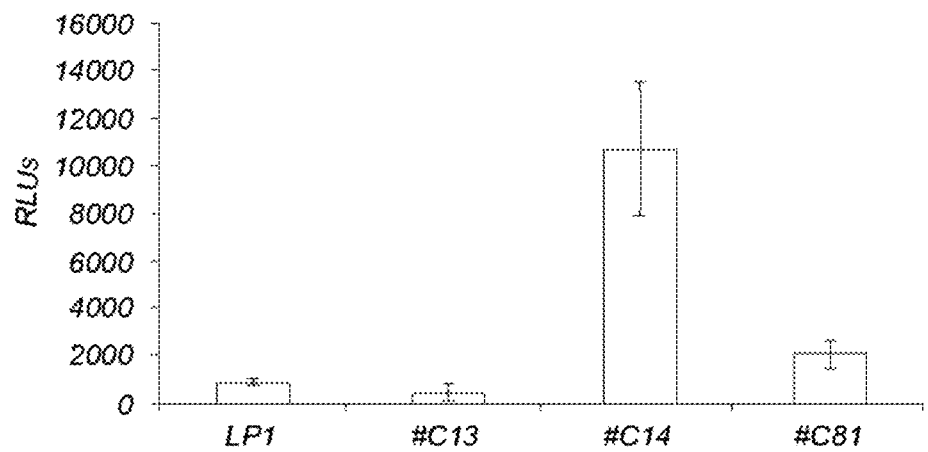
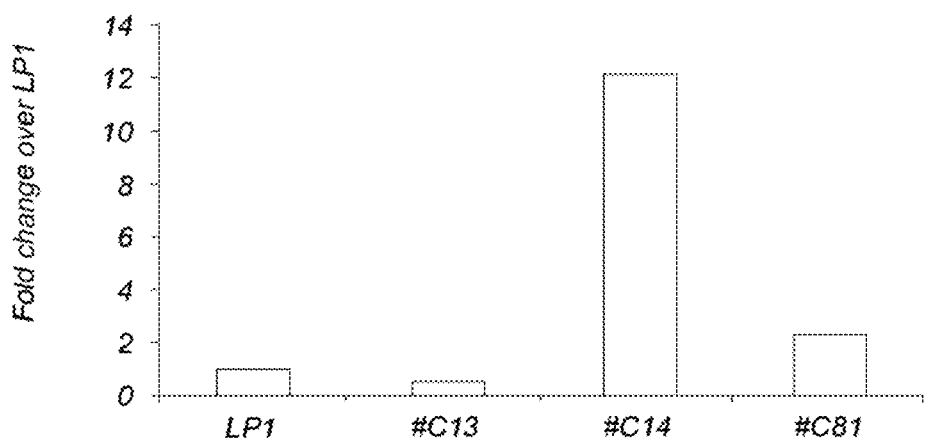
FIG. 13B

C13 TTTCTCTGGCCTAACTGGCCGGGTACCGTCGACTGTGCTGGACCCTGTAGATGCTAGTCTAGAAGAGGTTCAAAGGTCA

C13 TACCTAGGATAAGGAAGTACTTCTAGGTAGGCCCAGGTCACCCTGACCCTCTTCTAGGATAAGGAAGTACTTCTAGAAG

C13 AGGTCAGGGTGACCTGGCCTACCGGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCCAGTTAGGCC

C13 CTACAGGTCCGAGCACAGTCGACGAGAAATGTTCTGNCACCTG

SEQUENCE LISTING

<160> NUMBER OF SEQ ID NOS: 108

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aagcaaatat tgtgggttat ggattaactc gaa                                    33

<210> SEQ ID NO 2
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 2
ctgtttgccc actctatttg ccc                                              23

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcgcccttt ggaccttttg caatcctgg                                        29

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agcaaacagc aaacac                                                      16

<210> SEQ ID NO 5
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggacttagcc cctgtttgct cctccgataa ctggggtgac cttggttaat attcaccagc      60
agcctc                                                                 66

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gcccctgttt gctcctccga taactggggt gaccttggtt aatattcacc a               51

<210> SEQ ID NO 7
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcatctattt cctgcccaca tctggtataa aaggaggcag tggcccacag aggagcacag      60
ctgtg                                                                  65

<210> SEQ ID NO 8
```

```
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gggcgactca gatcccagcc agtggactta gccctgttt gctcctccga taactggggt    60
gaccttggtt aatattcacc agcagcctcc cccgttgccc ctctggatcc actgcttaaa   120
tacggacgag gacagggccc tgtctcctca gcttcaggca ccaccactga cctgggacag   180
tgaatc                                                              186

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gagcggaagt gggtctcaac cactataaat cctctctgtg cccgtccgga gctggtgagg    60
aca                                                                  63

<210> SEQ ID NO 10
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gggcatataa aacaggggca aggcacagac tcatagcaga gcaatcacca ccaagcctgg    60
aataactgca gccacc                                                    76

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttaatattta ac                                                        12

<210> SEQ ID NO 12
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12 agcttca                                                               7

<210> SEQ ID NO 13
<211> LENGTH: 7
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 13 cctttga                                                                    7

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
tgacctttga acct                                                            14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
ggtaattatt aacc                                                            14

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
ctagtagcaa ggctgactac acgagcacat atca                                      34

<210> SEQ ID NO 17
<211> LENGTH: 7
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17 tgagtca                                                                    7

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
ctggactttg gactc                                                           15

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
tcacttcctc ttttt                                                      15

<210> SEQ ID NO 20
<211> LENGTH: 558
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
ccctaaaatg gcaaacatt gcaagcagca aacagcaaac acacagccct ccctgcctgc       60
tgaccttgga gctggggcag aggtcagaga cctctctggg cccatgccac ctccaacatc     120
cactcgaccc cttggaattt cggtggagag gagcagaggt tgtcctggcg tggtttaggt     180
agtgtgagag gggaatgact cctttcggta agtgcagtgg aagctgtaca ctgcccaggc     240
aaagcgtccg ggcagcgtag gcgggcgact cagatcccag ccagtggact tagcccctgt     300
ttgctcctcc gataactggg gtgaccttgg ttaatattca ccagcagcct cccccgttgc     360
ccctctggat ccactgctta aatacggacg aggacagggc cctgtctcct cagcttcagg     420
caccaccact gacctgggac agtgaatccg gactctaagg taaatataaa attttttaagt   480 gtataatgtg ttaaactact gattctaatt gtttctctct tttagattcc aacctttgga   540
actgaattct agaccacc                                                   558

<210> SEQ ID NO 21
<211> LENGTH: 304
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
taaagcaaat atttgtggtt atggattaac tcgaacttct agaagctgtt tgcccactct     60
atttgcccat cctaggtagg cgcccttttgg acctttttgca atcctggctt ctagaagagc    120
aaacagcaaa cacatcctag gtaggactta gcccctgttt gctcctccga taactggggt    180
gaccttggtt aatattcacc agcagcctca tgctagcctc gaggatatca gatctgagcg    240
gaagtgggtc tcaaccacta taaatcctct ctgtgcccgt ccggagctgg tgaggacagc    300
cacc                                                                  304

<210> SEQ ID NO 22
<211> LENGTH: 238
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
aagcaaatat ttgtggttat ggattaactc gaactgtttg cccactctat ttgcccggcg     60
ccctttggac cttttgcaat cctggagcaa acagcaaaca cggacttagc cctgtttgc    120 tcctccgata actggggtga ccttggttaa tattcaccag cagcctcatg agcggaagtg    180
ggtctcaacc actataaatc ctctctgtgc ccgtccggag ctggtgagga cagccacc      238

```
<210> SEQ ID NO 23
<211> LENGTH: 211
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
taaagcaaat atttgtggtt atggattaac tcgaacttct agaagctgtt tgcccactct      60
atttgcccat cctaggtagg cgccctttgg accttttgca atcctggctt ctagaagagc     120
aaacagcaaa cacatcctag gtaggactta gcccctgttt gctcctccga taactggggt     180
gaccttggtt aatattcacc agcagcctca t                                    211

<210> SEQ ID NO 24
<211> LENGTH: 177
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
taaagcaaat atttgtggtt atggattaac tcgaactgtt tgcccactct atttgcccgg      60
cgccctttgg accttttgca atcctggagc aaacagcaaa cacggactta gcccctgttt     120
gctcctccga taactggggt gaccttggtt aatattcacc agcagcctca tgccacc        177

<210> SEQ ID NO 25
<211> LENGTH: 311
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
taaagcaaat atttgtggtt atggattaac tcgaacttct agaagctgtt tgcccactct      60
atttgcccat cctaggtagg cgccctttgg accttttgca atcctggctt ctagaagagc     120
aaacagcaaa cacatcctag gtaggactta gcccctgttt gctcctccga taactggggt     180
gaccttggtt aatattcacc agcagcctca tgctagcctc gaggatatca gatctgggca     240
tataaaacag gggcaaggca cagactcata gcagagcaat caccaccaag cctggaataa     300
ctgcagccac c                                                          311

<210> SEQ ID NO 26
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
aagcaaatat tgtggttat ggattaactc gaactgtttg cccactctat ttgcccggcg       60
ccctttggac cttttgcaat cctggagcaa acagcaaaca cggacttagc ccctgtttgc     120
tcctccgata actggggtga ccttggttaa tattccag cagcctcggg catataaaac       180
aggggcaagg cacagactca tagcagagca atcaccacca gcctggaat aactgcagcc     240 acc                                                                   243
```

<210> SEQ ID NO 27
<211> LENGTH: 214
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
aagcaaatat tgtggttat ggattaactc gaaggcgccc tttggaccttt ttgcaatcct      60 ggagcaaaca gcaaacacgg ccctgttttg ctcctccgat aactggggtg accttggtta    120
atattcacca gcagcctcgg gcatataaaa caggggcaag gcacagactc atagcagagc    180
aatcaccacc aagcctggaa taactgcagc cacc                                 214

<210> SEQ ID NO 28
<211> LENGTH: 228
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
aagcaaatat tgtggttat ggattaactc gaactgtttg cccactctat ttgcccggcg      60
ccctttggac cttttgcaat cctggagcaa acagcaaaca cgcccctgtt tgctcctccg    120
ataactgggg tgaccttggt taatattcac cagggcatat aaaacagggg caaggcacag    180
actcatagca gagcaatcac caccaagcct ggaataactg cagccacc                  228

<210> SEQ ID NO 29
<211> LENGTH: 427
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
taaagcaaat atttgtggtt atggattaac tcgaacttct agaagctgtt tgcccactct      60
atttgcccat cctaggtagg cgcccttttgg acctttttgca atcctggctt ctagaagagc   120
aaacagcaaa cacatcctag gtaggactta gcccctgttt gctcctccga taactggggt    180
gaccttggtt aatattcacc agcagcctca tgctagcctc gaggatatca gatctgggcg    240
actcagatcc cagccagtgg acttagcccc tgtttgctcc tccgataact ggggtgacct    300
tggttaatat tcaccagcag cctcccccgt tgcccctctg gatccactgc ttaaatacgg    360
acgaggacag ggccctgtct cctcagcttc aggcaccacc actgacctgg gacagtgaat    420
cgccacc                                                               427

<210> SEQ ID NO 30
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
taaagcaaat atttgtggtt atggattaac tcgaacttct agaagctgtt tgcccactct      60
atttgcccat cctaggtagg cgcccttttgg accttttgca atcctggctt ctagaagagc    120
aaacagcaaa cacatcctag gtaggactta gcccctgttt gctcctccga taactggggt    180
gaccttggtt aatattcacc agcagcctca tgctagcctc gaggatatca gatcttcatc    240
tatttcctgc ccacatctgg tataaaagga ggcagtggcc cacagaggag cacagctgtg    300
ccacc                                                                 305

<210> SEQ ID NO 31
<211> LENGTH: 239
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
aagcaaatat ttgtggttat ggattaactc gaactgtttg cccactctat ttgcccggcg     60 cccttttggac cttttgcaat cctggagcaa acagcaaaca cggacttagc ccctgtttgc   120
tcctccgata actggggtga ccttggttaa tattcaccag cagcctcatt catctatttc    180
ctgcccacat ctggtataaa aggaggcagt ggcccacaga ggagcacagc tgtgccacc    239

<210> SEQ ID NO 32
<211> LENGTH: 255
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
aagttaatat ttaacatcct agcacagctt cacttccagg tatgaccttt gaacctcttc     60
tagaagggta attattaacc tagctaggta tgaccttcga acctcttcta gaagtgaagc   120
tatgctagta gcaaggctga ctacacgagc acatatcaac gcgtcgacga tatcagatct   180
gggcatataa acaggggcaa ggcacagact catagcagag caattaccac caagcctgga   240
atagctgcag ccacc                                                    255

<210> SEQ ID NO 33
<211> LENGTH: 193
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
ttaatattta acatcctagc acagcttcac ttccaggtat gacctttgaa cctcttctag     60
aagggtaatt attaacctag ctaggtatga ccttcgaacc tcttctagaa gtgaagctgg   120
gcatataaac aggggcaagg cacagactca tagcagagca attaccacca agcctggaat   180
agctgcagcc acc                                                       193

<210> SEQ ID NO 34
<211> LENGTH: 283
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
taggttaata attacccttc taggattgag tcacttctag aagctggact ttggactcat    60
cctagaagtc acttcctctt ttttacctag aagaggttca aaggtcatac ctagcatagc   120
ttcacttcta gaagggtaat tattaaccta gctagtagca aggctgacta cacgagcaca   180
tatcaacgcg tcgacgatat cagatctggg catataaaac aggggcaagg cacagactca   240
tagcagagca atcaccacca ggcctggaat aactgcagcc acc                     283
```

<210> SEQ ID NO 35
<211> LENGTH: 222
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 35

```
ggttaataat tacccttcta ggattgagtc acttctagaa gctggacttt ggactcatcc    60
tagaagtcac ttcctctttt ttacctagaa gaggttcaaa ggtcatacct agcatagctt   120
cacttctaga agggtaatta ttaaccgggc atataaaaca ggggcaaggc acagactcat   180
agcagagcaa tcaccaccag gcctggaata actgcagcca cc                      222
```

<210> SEQ ID NO 36
<211> LENGTH: 432
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: modified_base
<222> LOCATION: (261)..(261)
<223> OTHER INFORMATION: a, c, t, or g

<400> SEQUENCE: 36

```
catagcttca cttctagaag aggtcagggt gacctgggcc tacctagcta ggttaataat    60
tacccttcta gaagtgactc aatcctagaa gccggaagtg gcatcctaga agaggttcaa   120
aggtcatacc tagtaaaaa agaggaagtg acttctagga taaggaagta cttctagaag   180
tacttcctta tcctagcata gcttcacttc tagaagaggt tcaaaggtca tacctaggta   240 tgaccttga acctcttcta naagttaata tttaacatcc tagaagggta attattaacc   300
tagcaaggct gactacacga gcacatatca gcgcgtcgac gatatcagac ctgggcatat   360
aaaacagggg caaggcacag actcatagca gagcaatcac caccaagcct ggaataactg   420
cagccaccat gg                                                       432
```

<210> SEQ ID NO 37
<211> LENGTH: 224
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 37

```
gtaaaaaaga ggaagtgact tctagaagag gttcaaaggt catacctagc taggttaata    60
attacccttc tagaagtact tccttatcct agtagcaagg ctgactacac gagcacatat   120
caacgcgtcg acgatatcag atctgggcat ataaaacagg gcaaggcac agacccatag   180 cagagcaatc accaccaagc ctggaataac tgcagccacc atgg                    224
```

<210> SEQ ID NO 38
<211> LENGTH: 410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
aagaggtcag ggtgacctgg gcctacctag gataaggaag tacttctaga agtgactcaa      60
tcctagaagg gtaattatta acctagctag gatgagtcca aagtccagct tctaggtagt     120
agggcaaagg tcacttctag gattgagtca cttctaggat gagtccaaag tccagcttct     180
agaagaggtt caaaggtcat acctaggtaa aaaagaggaa gtgacttcta gaagttaata     240
tttaacatcc taggagtcac ttcctctttt ttacctagta gcaaggctga ctacacgagc     300
acatatcaac gcgtcaacga tatcagatct gggcatataa acagggca aggcacagac      360 tcatagcaga gcaatcacca ccaagcctgg aataactgca gccaccatgg              410

<210> SEQ ID NO 39
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (291)..(291)
<223> OTHER INFORMATION: a, c, t, or g

<400> SEQUENCE: 39
tttctctggc ctaactggcc ggtaccgtcg actgtgctcg gacctgtaga tgctagtcta      60
gaagaggttc aaaggtcata cctaggataa ggaagtactt ctaggtaggc ccaggtcacc     120
ctgacctctt ctaggataag gaagtacttc tagaagaggt cagggtgacc tgggcctacc     180
tagaagtact tccttatcct aggtatgacc tttgaacctc ttctagacta gcatctacag     240
gtccgagcac agtcgacggt accggccagt taggccagag aaatgttctg ncacctg       297

<210> SEQ ID NO 40
<211> LENGTH: 263
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
tagtagggca aaggtcactt ctagaagccg gaagtggcat cctagaagtg actcaatcct      60
agaagaggtc agggtgacct gggcctacct agaagtgact caatcctagg atgtttaaata    120 ttaacttcta gtagcaaggc tgactacacg agcacatatc aacgcgtcga cgatatcaga    180
tctgggcata taaacagggg caaggcaca gactcatagc agagcaatca ccaccaagcc     240
tggaataact gcagccacca tgg                                          263

<210> SEQ ID NO 41
<211> LENGTH: 177
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
aagcaaatat ttgtggttat ggattaactc gaactgtttg cccactctat ttgcccggcg    60
ccctttggac cttttgcaat cctggagcaa acagcaaaca cgggcatata aacaggggc    120 aaggcacaga ctcatagcag agcaatcacc accaagcctg gaataactgc agccacc      177
```

<210> SEQ ID NO 42
<211> LENGTH: 227
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
aagcaaatat ttgtggttat ggattaactc gaactgtttg cccactctat ttgcccggcg    60
ccctttggac cttttgcaat cctggggact tagcccctgt ttgctcctcc gataactggg    120
gtgaccttgg ttaatattca ccagcagcct cgggcatata aacaggggc aaggcacaga    180 ctcatagcag agcaatcacc accaagcctg gaataactgc agccacc                 227
```

<210> SEQ ID NO 43
<211> LENGTH: 214
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
aagcaaatat ttgtggttat ggattaactc gaactgtttg cccactctat ttgcccagca    60
aacagcaaac acggacttag cccctgtttg ctcctccgat aactggggtg accttggtta    120
atattcacca gcagcctcgg gcatataaaa caggggcaag gcacagactc atagcagagc    180
aatcaccacc aagcctggaa taactgcagc cacc                                214
```

<210> SEQ ID NO 44
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
ctgtttgccc actctatttg cccggcgccc tttggaccct ttgcaatcct ggagcaaaca    60
gcaaacacgg acttagcccc tgtttgctcc tccgataact ggggtgacct tggttaatat    120
tcaccagcag cctcgggcat ataaaacagg ggcaaggcac agactcatag cagagcaatc    180
accaccaagc ctggaataac tgcagccacc                                     210
```

<210> SEQ ID NO 45
<211> LENGTH: 220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
aagcaaatat ttgtggttat ggattaactc gaaggcgccc tttggaccct tgcaatcct    60
```

```
ggagcaaaca gcaaacacgg acttagcccc tgtttgctcc tccgataact ggggtgacct    120
tggttaatat tcaccagcag cctcgggcat ataaaacagg ggcaaggcac agactcatag    180
cagagcaatc accaccaagc ctggaataac tgcagccacc                          220
```

<210> SEQ ID NO 46
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
agcttcactt ccaggtatga cctttgaacc tcttctagaa gggtaattat taacctagct    60
aggtatgacc ttcgaacctc ttctagaagt gaagctgggc atataaacag ggcaaggca    120 cagactcata gcagagcaat taccaccaag cctggaatag ctgcagccac c             171
```

<210> SEQ ID NO 47
<211> LENGTH: 155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
ggttaataat tacccttcta ggataggttc aaaggtcata cctagcatag cttcacttct    60
agaagggtaa ttattaaccg ggcatataaa acaggggcaa ggcacagact catagcagag    120
caatcaccac caggcctgga ataactgcag ccacc                               155
```

<210> SEQ ID NO 48
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
tgagtcactt ctagaagctg gactttggac tcatcctaga agtcacttcc tcttttttac    60
ctagaagagg ttcaaaggtc atacctagca tagcttcact tctagaaggg taattattaa    120
ccgggcatat aaaacagggg caaggcacag actcatagca gagcaatcac caccaggcct    180
ggaataactg cagccacc                                                  198
```

<210> SEQ ID NO 49
<211> LENGTH: 169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
ttaatattta acatcctagc acagcttcac ttccaggtat gacctttgaa cctcttctag    60
aagtgacctt cgaacctctt ctagaagtga agctgggcat ataaacaggg gcaaggcaca    120
gactcatagc agagcaatta ccaccaagcc tggaatagct gcagccacc                169
```

<210> SEQ ID NO 50

<211> LENGTH: 181
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
ggttaataat taccccttcta ggattgagtc acttctagaa gctggacttt ggactcatcc        60
tagaagtcac ttcctctttt ttacctagaa gggtaattat taaccgggca tataaacag        120 gggcaaggca cagactcata gcagagcaat caccaccagg cctggaataa ctgcagccac       180
c                                                                       181

<210> SEQ ID NO 51
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
ttaatattta acatcctagc acagcttcac ttccaggtat gacctttgaa cctcttctag        60
aagggtaatt attaacctag ctaggtaggg catataaaca ggggcaaggc acagactcat       120
agcagagcaa ttaccaccaa gcctggaata gctgcagcca cc                         162

<210> SEQ ID NO 52
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
ttaatattta acatcctagc acggtaatta ttaacctagc taggtagggc atataaacag        60
gggcaaggca cagactcata gcagagcaat taccaccaag cctggaatag ctgcagccac       120
c                                                                       121

<210> SEQ ID NO 53
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
aagcaaatat ttgtggttat ggattaactc gaactgtttg cccactctat ttgcccggcg        60 cccctttggac cttttgcaat cctggagcaa acagcaaaca cgaggctgct ggtgaatatt      120
aaccaaggtc accccagtta tcggaggagc aaacaggggc taagtccggg catataaaac      180
aggggcaagg cacagactca tagcagagca atcaccacca gcctggaat aactgcagcc       240 acc                                                                    243

<210> SEQ ID NO 54
<211> LENGTH: 243
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
ctgtttgccc actctatttg cccaagcaaa tatttgtggt tatggattaa ctcgaaggcg    60
ccctttggac cttttgcaat cctggagcaa acagcaaaca cggacttagc ccctgtttgc   120
tcctccgata actggggtga ccttggttaa tattcaccag cagcctcggg catataaaac   180
aggggcaagg cacagactca tagcagagca atcaccacca agcctggaat aactgcagcc   240
acc                                                                 243
```

<210> SEQ ID NO 55
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
agcaaacagc aaacacggac ttagcccctg tttgctcctc cgataactgg ggtgaccttg    60
gttaatattc accagcagcc tcaagcaaat atttgtggtt atggattaac tcgaactgtt   120
tgcccactct atttgcccgg cgcccttttgg accttttgca atcctggggg catataaaac   180
aggggcaagg cacagactca tagcagagca atcaccacca agcctggaat aactgcagcc   240
acc                                                                 243
```

<210> SEQ ID NO 56
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
ttcgagttaa tccataacca caaatatttg cttctgtttg cccactctat ttgcccggcg    60
ccctttggac cttttgcaat cctggagcaa acagcaaaca cggacttagc ccctgtttgc   120
tcctccgata actggggtga ccttggttaa tattcaccag cagcctcggg catataaaac   180
aggggcaagg cacagactca tagcagagca atcaccacca agcctggaat aactgcagcc   240
acc                                                                 243
```

<210> SEQ ID NO 57
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
ctgtttgccc actctatttg cccagcaaac agcaaacaca agcaaatatt tgtggttatg    60
gattaactcg aaggcgccct ttggaccttt tgcaatcctg ggacttagc ccctgtttgc   120 tcctccgata actggggtga ccttggttaa tattcaccag cagcctcggg catataaaac   180
aggggcaagg cacagactca tagcagagca atcaccacca agcctggaat aactgcagcc   240
acc                                                                 243
```

<210> SEQ ID NO 58

```
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
aagcaaatat tgtggttat ggattaactc gaactgtttg cccactctat ttgcccggcg        60 cccttttggac cttttgcaat cctgggtgtt tgctgtttgc tggacttagc ccctgtttgc     120
tcctccgata actggggtga ccttggttaa tattcaccag cagcctcggg catataaaac     180
aggggcaagg cacagactca tagcagagca atcaccacca gcctggaat  aactgcagcc     240 acc                                                                    243

<210> SEQ ID NO 59
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
ggttaataat tacctaccta gaagaggttc aaaggtcata cctagcatag cttcacttct        60
agaagggtaa ttattaaccc ttctaggatt gagtcacttc tagaagctgg actttggact     120
catcctagaa gtcacttcct ctttttgggc atataaaaca ggggcaaggc acagactcat     180
agcagagcaa tcaccaccag gcctggaata actgcagcca cc                          222

<210> SEQ ID NO 60
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
ggttaataat taccccttcta ggataaaaag aggaagtgac ttctaggatg agtccaaagt      60
ccagcttcta gaagtgactc atacctagaa gaggttcaaa ggtcatacct agcatagctt     120
cacttctaga agggtaatta ttaaccgggc atataaaaca ggggcaaggc acagactcat     180
agcagagcaa tcaccaccag gcctggaata actgcagcca cc                          222

<210> SEQ ID NO 61
<211> LENGTH: 193
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
ggttaataat taccccttcta gaagaggttc aaaggtcata cctggaagtg aagctgtgct      60
aggatgttaa atattaatag ctaggtatga ccttcgaacc tcttctagaa gtgaagctgg     120
gcatataaac aggggcaagg cacagactca tagcagagca attaccacca gcctggaat       180 agctgcagcc acc                                                          193

<210> SEQ ID NO 62
<211> LENGTH: 193
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
gggcatataa acaggggcaa ggcacagact catagcagag caattaccac caagcctgga      60
atagctgcat taatatttaa catcctagca cagcttcact tccaggtatg acctttgaac     120
ctcttctaga agggtaatta ttaacctagc taggtatgac cttcgaacct cttctagaag    180
tgaagctgcc acc                                                        193

<210> SEQ ID NO 63
<211> LENGTH: 193
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
ttaatattta acatcctagc acagcttcac ttccaggtat gacctttgaa ccttagctag     60
gtatgacctt cgaacctctt ctagaagtga agctcttcta gaagggtaat tattaaccgg    120
gcatataaac aggggcaagg cacagactca tagcagagca attaccacca gcctggaat    180 agctgcagcc acc                                                       193

<210> SEQ ID NO 64
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
ggttaataat taccccttcta ggattgagtc acttctagaa ggagtccaaa gtccagatcc     60
tagaagtcac ttcctctttt ttacctagaa gaggttcaaa ggtcacttct agaagtgaag    120
ctatgctagg taggtaatta ttaaccgggc atataaaaca ggggcaaggc acagactcat    180
agcagagcaa tcaccaccag gcctggaata actgcagcca cc                        222

<210> SEQ ID NO 65
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
ggttaataat taccccttcta ggattgagtc acttctagaa ggagtccaaa gtccagatcc     60
tagaagtcac ttcctctttt ttacctagaa gaggttcaaa ggtcatacct agcattgaag    120
ctcttctaga agggtaatta ttaaccgggc atataaaaca ggggcaaggc acagactcat    180
agcagagcaa tcaccaccag gcctggaata actgcagcca cc                        222

<210> SEQ ID NO 66
<211> LENGTH: 193
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 66
ggtaattatt aacctagcta ggtatgacct tcgaacctct tctagaagtt aatatttaac    60
atcctagcac agcttcactt ccaggtatga cctttgaacc tcttctagaa gtgaagctgg   120
gcatataaac aggggcaagg cacagactca tagcagagca attaccacca agcctggaat   180
agctgcagcc acc                                                      193

<210> SEQ ID NO 67
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
aagcaaatat ttgtggttat ggattaactc gaactgtttg cccactctat ttgcccggcg    60
ccctttggac cttttgcaat cctggagcaa acagcaaaca cggacttagc ccctgtttgc   120
tcctccgata actggggtga ccttggttaa tattcaccag cagcctcggg catataaaac   180
aggggcaagg cacagactca tagcagagca atcaccacca agcctggaat aactgcagcc   240
acagtgaatc cggactctaa ggtaaatata aattttttaa gtgtataatg tgttaaacta   300
ctgattctaa ttgtttctct cttttagatt ccaacctttg gaactgaatt ctagaccacc   360

<210> SEQ ID NO 68
<211> LENGTH: 419
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
taaagcaaat atttgtggtt atggattaac tcgaacttct agaagctgtt tgcccactct    60
atttgcccat cctaggtagg cgccctttgg acctttttgca atcctggctt ctagaagagc   120
aaacagcaaa cacatcctag gtaggactta gcccctgttt gctcctccga taactggggt   180
gaccttggtt aatattcacc agcagcctca tgctagcctc gaggatatca gatcttcatc   240
tatttcctgc ccacatctgg tataaaagga ggcagtggcc cacagaggag cacagctgtg   300
cagtgaatcc ggactctaag gtaaatataa aattttttaag tgtataatgt gttaaactac   360
tgattctaat tgtttctctc ttttagattc caacctttgg aactgaattc tagaccacc    419

<210> SEQ ID NO 69
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
aagcaaatat ttgtggttat ggattaactc gaactgtttg cccactctat ttgcccggcg    60 cccttggac cttttgcaat cctggagcaa acagcaaaca cgggcatata aacaggggc   120 aaggcacaga ctcatagcag agcaatcacc accaagcctg gaataactgc agccacagtg   180
aatccggact ctaaggtaaa tataaaattt ttaaggaggc tgctggtgaa tattaaccaa   240
ggtcacccca gttatcggag gagcaaacag gggctaagtc ctgtataatg tgttaaacta    300
ctgattctaa ttgtttctct cttttagatt ccaacctttg gaactgaatt ctagaccacc    360

<210> SEQ ID NO 70
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
ggttaataat tacccttcta ggattgagtc acttctagaa gctggacttt ggactcatcc    60
tagaagtcac ttcctctttt ttacctagaa gaggttcaaa ggtcatacct agcatagctt   120
cacttctaga agggtaatta ttaaccgggc atataaaaca ggggcaaggc acagactcat   180
agcagagcaa tcaccaccag gcctggaata actgcagcca cagtgaatcc ggactctaag   240
gtaaatataa aattttttaag tgtataatgt gttaaactac tgattctaat tgtttctctc   300
ttttagattc caacctttgg aactgaattc tagaccacc                          339

<210> SEQ ID NO 71
<211> LENGTH: 310
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
ttaatattta acatcctagc acagcttcac ttccaggtat gacctttgaa cctcttctag    60
aagggtaatt attaacctag ctaggtatga ccttcgaacc tcttctagaa gtgaagctgg   120
gcatataaac aggggcaagg cacagactca tagcagagca attaccacca agcctggaat   180
agctgcagcc acagtgaatc cggactctaa ggtaaatata aattttttaa gtgtataatg   240
tgttaaacta ctgattctaa ttgtttctct cttttagatt ccaacctttg gaactgaatt   300
ctagaccacc                                                          310

<210> SEQ ID NO 72
<211> LENGTH: 341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
ttaatattta acatcctagc acagcttcac ttccaggtat gacctttgaa cctcttctag    60
aagggtaatt attaacctag ctaggtatga ccttcgaacc tcttctagaa gtgaagctgg   120
gcatataaac aggggcaagg cacagactca tagcagagca attaccacca agcctggaat   180
agctgcagcc acagtgaatc cggactctaa ggtaaatata aattttttaa gtgaccttcg   240
aacctcttct agaagtgaag cttgtataat gtgttaaact actgattcta attgtttctc   300
tcttttagat tccaaccttt ggaactgaat tctagaccac c                       341

<210> SEQ ID NO 73
<211> LENGTH: 243
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 73
aagcaaatat ttgtggttat ggattaactc gaactgtttg cccactctat ttgcccggcg      60
ccctttggac cttttgcaat cctggagcaa acagcaaaca ctaacttagc ccctgtttgc     120
tcctccgatc cccatggtga ccttggttaa tattcaccag cagcctcggg catataaaac     180
aggggcaagg cacagactca tagcagagca atcaccacca agcctggaat aactgcagcc     240
acc                                                                   243

<210> SEQ ID NO 74
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
aagcaaatat ttgtggttat ggattaactc gaactgtttg cccactctat ttgcccggcg      60
ccctttggac cttttgcaat cctggagcaa acagcaaaca cagacttagc ccctgtttgc     120
tcctccgatg gctaaggtga ccttggttaa tattcaccag cagctagggg catataaaac     180
aggggcaagg cacagactca tagcagagca atcaccacca agcctggaat aactgcagcc     240
acc                                                                   243

<210> SEQ ID NO 75
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
aagcaaatat ttgtggttat ggattaactc gaactgtttg cccactctat ttgcccggcg      60
ccctttggac cttttgcaat cctggagcaa acagcaaaca ctaacttagc ccctgtttgc     120
tccttagatc cccatggtga ccttggttaa tattcaccag caatctcggg catataaaac     180
aggggcaagg cacagactca tagcagagca atcaccacca agcctggaat aactgcagcc     240
acc                                                                   243

<210> SEQ ID NO 76
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
aagcaaatat ttgtggttat ggattaactc gaactgtttg cccactctat ttgcccggcg      60
ccctttggac cttttgcaat cctggagcaa acagcaaaca cggacttagc ccctatttac     120
tcctccgatg actcaggtga ctttggttaa tattcaccag cagcctcggg catataaaac     180
aggggcaagg cacagactca tagcagagca atcaccacca agcctggaat aactgcagcc     240
acc                                                                   243
```

<210> SEQ ID NO 77
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
aagcaaatat ttgtggttat ggattaactc gaactgtttg cccactctat ttgcccggcg     60 cccttttggac cttttgcaat cctggagcaa acagcaaaca cggacttagc ccctgtttgc    120
tcctccgata acggtgtga ccttggttaa tattcaccat agagctcggg catataaaac     180
aggggcaagg cacagactca tagcagagca atcaccacca agcctggaat aactgcagcc    240
acc                                                                  243

<210> SEQ ID NO 78
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
aagcaaatat ttgtggttat ggattaactc gaactgtttg cccactctat ttgcccggcg     60 cccttttggac cttttgcaat cctggagcaa acagcaaaca ctaacttagc ccctatttac    120
tccttagatc cccatggtga ctttggttaa tattcaccag caatctcggg catataaaac    180
aggggcaagg cacagactca tagcagagca atcaccacca agcctggaat aactgcagcc    240
acc                                                                  243

<210> SEQ ID NO 79
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
aagcaaatat ttgtggttat ggattaactc gaactgtttg cccactctat ttgcccggcg     60 cccttttggac cttttgcaat cctggagcaa acagcaaaca ctcactttgc ccctatttac    120
tcctccgatg actcaggtga ctttggttaa tattcaccag cagctagggg catataaaac    180
aggggcaagg cacagactca tagcagagca atcaccacca agcctggaat aactgcagcc    240
acc                                                                  243

<210> SEQ ID NO 80
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
aagcaaatat ttgtggttat ggattaactc gaactgtttg cccactctat ttgcccggcg     60 cccttttggac cttttgcaat cctggagcaa acagcaaaca cgcggaggag caaacagggg    120
ctaagtcata actggggtga ccttggttaa tattcaccag cagcctcggg catataaaac    180

```
aggggcaagg cacagactca tagcagagca atcaccacca agcctggaat aactgcagcc    240
acc                                                                  243

<210> SEQ ID NO 81
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
aagcaaatat ttgtggttat ggattaactc gaactgtttg cccactctat ttgcccggcg    60 cccttttggac cttttgcaat cctggagcaa acagcaaaca cggacttagc ccctgtttgc   120
tcctccgata actgggggct gctggtgaat attaaccaag gtcactcggg catataaaac   180
aggggcaagg cacagactca tagcagagca atcaccacca agcctggaat aactgcagcc   240
acc                                                                  243

<210> SEQ ID NO 82
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
aagcaaatat ttgtggttat ggattaactc gaactgtttg cccactctat ttgcccggcg    60 cccttttggac cttttgcaat cctggagcaa acagcaaaca cggacttagc ggagcaaaca   120
gggtccgata actggggtga ccttggttaa tattcaccag cagcctcggg catataaaac   180
aggggcaagg cacagactca tagcagagca atcaccacca agcctggaat aactgcagcc   240
acc                                                                  243

<210> SEQ ID NO 83
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
aagcaaatat ttgtggttat ggattaactc gaactgtttg cccactctat ttgcccggcg    60 cccttttggac cttttgcaat cctggagcaa acagcaaaca cggacttagc ccctgtttgc   120
tcctccgata actggggtga cctgctggtg aatattaacc aagcctcggg catataaaac   180
aggggcaagg cacagactca tagcagagca atcaccacca agcctggaat aactgcagcc   240
acc                                                                  243

<210> SEQ ID NO 84
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
```

```
aagcaaatat ttgtggttat ggattaactc gaactgtttg cccactctat ttgcccggcg    60 cccctttggac cttttgcaat cctggagcaa acagcaaaca cggacttagc ccctgtttgc   120
tcctccgccc cagttattga ccttggttaa tattcaccag cagcctcggg catataaaac   180
aggggcaagg cacagactca tagcagagca atcaccacca agcctggaat aactgcagcc   240
acc                                                                  243
```

<210> SEQ ID NO 85
<211> LENGTH: 233
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
aagcaaatat ttgtggttat ggattaactc gaactgtttg cccactctat ttgcccggcg    60 cccctttggac cttttgcaat cctggagcaa acagcaaaca cggacttagc ccctgtttgc   120
tcctccgtga ccttggttaa tattcaccag cagcctcggg catataaaac aggggcaagg   180
cacagactca tagcagagca atcaccacca agcctggaat aactgcagcc acc           233
```

<210> SEQ ID NO 86
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

```
aagcaaatat ttgtggttat ggattaactc gaactgtttg cccactctat ttgcccggcg    60 cccctttggac cttttgcaat cctggagcaa acagcaaaca cgactcagat cccagccagt   120
ggacttagcc cctgtttgct cctccgataa ctggggtgac cttggttaat attcaccagc   180
agcctccccc gttgcccctc tggggcatat aaaacagggg caaggcacag actcatagca   240
gagcaatcac caccaagcct ggaataactg cagccacc                            278
```

<210> SEQ ID NO 87
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 15-17-18-19-14-12-15-10-SD/SA_SV40

<400> SEQUENCE: 87

```
taacttagcc cctgtttgct cctccgatcc ccatggtgac cttggttaat attcaccagc    60
agcctc                                                               66
```

<210> SEQ ID NO 88
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 11 mutations in spacer seqs and binding sites
      (NO HNF site mutations)

```
<400> SEQUENCE: 88
agacttagcc cctgtttgct cctccgatgg ctaaggtgac cttggttaat attcaccagc    60
agctag                                                              66

<210> SEQ ID NO 89
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
taacttagcc cctgtttgct ccttagatcc ccatggtgac cttggttaat attcaccagc    60
aatctc                                                              66

<210> SEQ ID NO 90
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ggacttagcc cctatttact cctccgatga ctcaggtgac tttggttaat attcaccagc    60
agcctc                                                              66

<210> SEQ ID NO 91
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ggacttagcc cctgtttgct cctccgatag acggtgtgac cttggttaat attcaccata    60
gagctc                                                              66

<210> SEQ ID NO 92
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
taacttagcc cctatttact ccttagatcc ccatggtgac tttggttaat attcaccagc    60
aatctc                                                              66

<210> SEQ ID NO 93
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tcactttgcc cctatttact cctccgatga ctcaggtgac tttggttaat attcaccagc    60
``` agctag                                                             66

<210> SEQ ID NO 94
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gcggaggagc aaacaggggc taagtcataa ctggggtgac cttggttaat attcaccagc    60
agcctc                                                             66

<210> SEQ ID NO 95
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ggacttagcc cctgtttgct cctccgataa ctgggggctg ctggtgaata ttaaccaagg    60
tcactc                                                             66

<210> SEQ ID NO 96
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ggacttagcg gagcaaacag ggtccgataa ctggggtgac cttggttaat attcaccagc    60
agcctc                                                             66

<210> SEQ ID NO 97
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ggacttagcc cctgtttgct cctccgataa ctggggtgac ctgctggtga atattaacca    60
agcctc                                                             66

<210> SEQ ID NO 98
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ggacttagcc cctgtttgct cctccgcccc agtattgac cttggttaat attcaccagc    60
agcctc                                                             66

<210> SEQ ID NO 99

```
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ggacttagcc cctgtttgct cctccgtgac cttggttaat attcaccagc agcctc          56

<210> SEQ ID NO 100
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gactcagatc ccagccagtg gacttagccc ctgtttgctc ctccgataac tggggtgacc      60
ttggttaata ttcaccagca gcctcccccg ttgcccctct g                         101

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
acttagcccc tgtttgctcc tccg                                             24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tgaccttggt taatattcac cagc                                             24

<210> SEQ ID NO 103
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ccctgtttgc tcctccg                                                     17

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tggttaatat tcaccagc                                                    18
```

```
<210> SEQ ID NO 105
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ccctgtttgc tcc                                                             13

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tgaccttggt taatattcac ca                                                   22

<210> SEQ ID NO 107
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ccctatttac tcc                                                             13

<210> SEQ ID NO 108
<211> LENGTH: 580
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
atagtaatca attacggggt cattagttca tagcccatat atggagttcc gcgttacata          60
acttacggta aatggcccgc ctggctgacc gcccaacgac ccccgcccat tgacgtcaat         120
aatgacgtat gttcccatag taacgccaat agggactttc cattgacgtc aatgggtgga        180
gtatttacgg taaactgccc acttggcagt acatcaagtg tatcatatgc caagtacgcc        240
ccctattgac gtcaatgacg gtaaatggcc cgcctggcat tatgcccagt acatgacctt        300
atgggacttt cctacttggc agtacatcta cgtattagtc atcgctatta ccatggtgat        360
gcggttttgg cagtacatca atgggcgtgg atagcggttt gactcacggg gatttccaag        420
tctccacccc attgacgtca atgggagttt gttttggcac caaaatcaac gggactttcc        480
aaaatgtcgt aacaactccg ccccattgac gcaaatgggc ggtaggcgtg tacggtggga        540
ggtctatata agcagagctg gtttagtgaa ccgtcagatc                              580
```

LIVER-SPECIFIC VIRAL PROMOTERS AND METHODS OF USING THE SAME

CROSS-REFERENCE TO RELATED APPLICATIONS

This application is a continuation of International Application No. PCT/EP2019/081743 filed Nov. 19, 2019, which claims the benefit of and priority to European Application No. 18207027.6, filed Nov. 19, 2018, both of which are hereby incorporated by reference herein in their entireties.

SEQUENCE LISTING

The instant application contains a Sequence Listing which has been submitted in ASCII format via EFS-WEB and is hereby incorporated by reference in its entirety. Said ASCII copy, created on Aug. 27, 2021, is named 069818-0645_SL.txt and is 48,081 bytes.

Studies on liver uptake of DNA molecules and vectors, such as viral vectors, used in gene therapy have shown that the liver has a high capacity to take these up from the circulation. Indeed, it is well established that many viral vectors used in gene therapy, including adeno associated virus (AAV) vectors, can be efficiently taken up in the liver, thus making this organ relatively easy to target compared to other organs.

Moreover, the liver has been a target organ for gene therapy due to its central role in metabolism and production of serum proteins. Much of the current enthusiasm for liver-directed AAV gene therapy product development stems from preclinical and clinical successes in the field of hemophilia B. Numerous studies in classic mouse and dog models of hemophilia A and B have demonstrated compelling results from administration of vectors, including AAV vectors, encoding relevant clotting factors, with the vector trafficking to the liver for gene expression. Recently success has also been shown in human clinical trials.

However, targeting the liver is still not absolutely precise, and off-target delivery and expression may lead to reduced efficacy or complications. Accordingly, there is a need in the art for development of robust liver-specific promoters that will adequately and specifically or preferentially express an encoded gene of interest in the liver. The present disclosure fulfills this need.

SUMMARY OF INVENTION

Described herein are liver-specific promoters, adeno-associated virus (AAV) gene therapy vectors comprising the promoter, and therapeutic agents, and methods and kits using the same.

Thus, in accordance with some embodiments, there are provided synthetic polynucleotides comprising at least three promoter-derived nucleic acids selected from the group consisting of: (a) HNF1/HNF3 (SEQ ID NO:1); (b) HNF3/HNF3 (SEQ ID NO:2); (c) c/EBP/HNF4 (SEQ ID NO:3); (d) HS_CRM2/HNF3 (SEQ ID NO:4); and (e) HS_CRM8 (SEQ ID NO:6) or a variant thereof. In some embodiments, the synthetic polynucleotides comprise at least SEQ ID NO:3 and SEQ ID NO:6 or variants or derivatives thereof.

In some embodiments, a variant of the HS_CRM8 sequence may be selected from the group consisting of SEQ ID NO:5, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, and SEQ ID NO:100.

In some embodiments, the synthetic polynucleotides may comprise at least four of the promoter-derived nucleic acids. In some embodiments, the synthetic polynucleotides comprise the five promoter-derived nucleic acids (a)-(e). In some embodiments, the synthetic polynucleotides have at least 90% identity with the synthetic polynucleotide comprising the five promoter-derived nucleic acids (a)-(e).

In accordance with some embodiments, there are provided synthetic polynucleotides having at least 90% identity with a synthetic polynucleotide comprising at least three promoter-derived nucleic acids selected from the group consisting of: HNF1/HNF3 (SEQ ID NO:1); HNF3/HNF3 (SEQ ID NO:2); c/EBP/HNF4 (SEQ ID NO:3); HS_CRM2/HNF3 (SEQ ID NO:4); and HS_CRM8 (SEQ ID NO:6) or a variant thereof.

In some embodiments, the synthetic polynucleotides comprise consecutively from the 5' to 3' SEQ ID NO:1, SEQ ID NO:2, SEQ ID NO:3, SEQ ID NO:4, and SEQ ID NO:6.

In some embodiments, the synthetic polynucleotides further comprise at least one minimal promoter nucleic acid. In some embodiments, the sequence of the minimal promoter nucleic acid is derived from SERPINE1 (SEQ ID NO:7), SERPINA1 (SEQ ID NO:8), APOC2 (SEQ ID NO:9), or G6PC (SEQ ID NO:10) or a minimal promoter nucleic acid having at least 90% sequence identity with SERPINE1 (SEQ ID NO:7), SERPINA1 (SEQ ID NO:8), APOC2 (SEQ ID NO:9), or G6PC (SEQ ID NO:10). In some embodiments, the minimal promoter nucleic acid comprises a sequence selected from the group consisting of: SEQ ID NOs:7, 8, 9 and 10.

In some embodiments, the orientation of at least one of the promoter-derived nucleic acids is inverted.

In some embodiments the synthetic polynucleotides is a reverse complement of any one of the aforementioned synthetic polynucleotides.

In some embodiments, the synthetic polynucleotides further comprise at least one spacer nucleic acid located between two of the promoter-derived nucleic acids. In some embodiments, the spacer may be 1-50 bp or 1-200 bp, such as 5-150 bp, 10-100 bp, 15-75 bp, or 20-50 bp, or any number of base pairs in between. In some embodiments, the synthetic polynucleotide does not comprise a spacer.

In some embodiments, the synthetic polynucleotides further comprise an operably linked nucleic acid sequence encoding an intron. In some embodiments, the intron is derived from SV40. In some embodiments the intron is derived from minute virus of mice (MVM). In some embodiments, the intron is a synthetic minimal intron. In some embodiments, the intronic sequence has a length of less than 100 nucleotides. In some embodiments, the intronic sequence may comprise one or more of the promoter derived nucleic acids.

In some embodiments, the synthetic polynucleotide is less than 250 base pairs in length. In some embodiments, the synthetic polynucleotide is less than 300 base pairs in length.

In some embodiments, the polynucleotide has a sequence selected from the group consisting of SEQ ID NOs:21, 22, 23, 24, 25, 26, 27, 28, 29, 30, 31. In some embodiments, the polynucleotide has a sequence selected from the group consisting of SEQ ID NOs:41-45; 53-58; 67-69; 73-86.

In some embodiments, the synthetic polynucleotide promotes transgene expression in the liver, preferably liver-specific transgene expression. In some embodiments, the synthetic polynucleotide is suitable for promoting liver-specific transgene expression at a level at least 1.5-fold greater than an LP1 promoter. In some embodiments, the synthetic polynucleotide is suitable for promoting liver-specific transgene expression at a level at least 2-fold greater than an LP1 promoter. In some embodiments, the synthetic polynucleotide has a reduced transgene expression at a level of at least 4-fold less than an CMV promoter in non-liver derived cells. In some embodiments, the non-liver derived cells are A549 cells. In some embodiments, the synthetic polynucleotide is suitable for promoting liver-specific transgene expression at a level at least 1.5-fold greater than a CMV promoter in liver-derived cells. In some embodiments, the synthetic polynucleotide is suitable for promoting liver-specific transgene expression at a level at least 2-fold greater than a CMV promoter in liver-derived cells. In some embodiments, the synthetic polynucleotide has reduced transgene expression at a level of at least 1.5-fold less than an LP1 promoter in non-liver derived cells. In some embodiments, the synthetic polynucleotide has reduced transgene expression at a level of at least 2 fold less than an LP1 promoter in non-liver derived cells.

In some embodiments, the synthetic polynucleotides further comprise an operably linked nucleic acid sequence encoding a post-transcriptional regulatory element.

In some embodiments, the synthetic polynucleotides further comprise an operably linked nucleic acid sequence encoding polyA element.

In some embodiments, the synthetic polynucleotides further comprise an operably linked transgene.

In some embodiments, the synthetic polynucleotides further comprise an operably linked transgene, wherein the transgene encodes AAT, AGXT, ARG, ASL, ASS, ATP7B, BCKDHA, BCKDHB, CFH, CFTF, CPS, DBT, FAH, FIX, FVIII, HAMP, HFE, JH, MUT, NAGS, OTC, PCCA, PCCB, PI, SLC40A1, TFR2, TTR, UGT1A1, Urokinase, PXBP or variants, derivatives or equivalents thereof.

In accordance with some embodiments, there are provided synthetic polynucleotides comprising at least three promoter-derived nucleic acids selected from the group consisting of: (a) Motif_44 (SEQ ID NO:12); (b) NRF2F1 (SEQ ID NO:14); (c) HNF1A (SEQ ID NO:15); (d) IA2 (SEQ ID NO:16); and (e) a biological equivalent of each thereof.

In some embodiments, the synthetic polynucleotides comprise the four promoter-derived nucleic acids (a)-(d) of the immediately foregoing embodiment. In some embodiments, the synthetic polynucleotides have at least 90% identity with the synthetic polynucleotide comprising the four promoter-derived nucleic acids (a)-(d).

In accordance with some embodiments, there are provided synthetic polynucleotides having at least 90% identity with a synthetic polynucleotide comprising at least three promoter-derived nucleic acids selected from the group consisting of: Motif_44 (SEQ ID NO:12); NRF2F1 (SEQ ID NO:14); HNF1A (SEQ ID NO:15); and IA2 (SEQ ID NO:16).

In some embodiments, the synthetic polynucleotides comprise consecutively from the 5' to 3' SEQ ID NO:12, SEQ ID NO:15, and SEQ ID NO:16. In some embodiments, SEQ ID NO:14 is 3' to SEQ ID NO:15. In some embodiments, SEQ ID NO:14 is 5' to SEQ ID NO:15.

In some embodiments, the synthetic polynucleotides further comprise one or more sequences selected from: (e) HNF1B (SEQ ID NO:11); (f) JUN/FOS (SEQ ID NO:17); (g) HNF4A (SEQ ID NO:18); (h) SPI1 (SEQ ID NO:19).

In some embodiments, the synthetic polynucleotides comprise consecutively from 5' to 3': SEQ ID NO:11, SEQ ID NO:12, SEQ ID NO:14, SEQ ID NO:15, SEQ ID NO:14, SEQ ID NO:12, and SEQ ID NO:16. In some embodiments, the synthetic polynucleotide has at least 90% identity with the synthetic polynucleotide comprising consecutively from 5' to 3': SEQ ID NO:11, SEQ ID NO:12, SEQ ID NO:14, SEQ ID NO:15, SEQ ID NO:14, SEQ ID NO:12, and SEQ ID NO:16.

In some embodiments, the synthetic polynucleotides comprise consecutively from 5' to 3': SEQ ID NO:15, SEQ ID NO:17, SEQ ID NO:18, SEQ ID NO:19, SEQ ID NO:14, SEQ ID NO:12, SEQ ID NO:15, and SEQ ID NO:16. In some embodiments, the synthetic polynucleotides has at least 90% identity with the synthetic polynucleotide comprising consecutively from 5' to 3': SEQ ID NO:15, SEQ ID NO:17, SEQ ID NO:18, SEQ ID NO:19, SEQ ID NO:14, SEQ ID NO:12, SEQ ID NO:15, and SEQ ID NO:16.

In some embodiments, the synthetic polynucleotides comprise SEQ ID NO:15 and/or SEQ ID NO:16; and SEQ ID NO:17, SEQ ID NO:18, and SEQ ID NO:19. In some embodiments, the synthetic polynucleotides comprise SEQ ID NO:15 and/or SEQ ID NO:16; and SEQ ID NO:14 and SEQ ID NO:12.

In some embodiments, the synthetic polynucleotides further comprise at least one minimal promoter nucleic acid. In some embodiments, the sequence of the minimal promoter nucleic acid is derived from SERPINE1 (SEQ ID NO:7), SERPINA1 (SEQ ID NO:8), APOC2 (SEQ ID NO:9), or G6PC (SEQ ID NO:10) or a minimal promoter nucleic acid having at least 90% sequence identity with SERPINE1 (SEQ ID NO:7), SERPINA1 (SEQ ID NO:8), APOC2 (SEQ ID NO:9), or G6PC (SEQ ID NO:10). In some embodiments, the minimal promoter nucleic acid comprises a sequence selected from the group consisting of: SEQ ID NOs:7, 8, 9 and 10.

In some embodiments, the orientation of at least one of the promoter-derived nucleic acids is inverted.

In some embodiments, the synthetic polynucleotides further comprise at least one spacer nucleic acid located between two of the promoter-derived nucleic acids.

In some embodiments, the synthetic polynucleotides further comprise an operably linked nucleic acid sequence encoding an intron. In some embodiments, the intron nucleic acid comprises a sequence derived from SV40. In some embodiments the intron is derived from minute virus of mice (MVM). In some embodiments, the intron is a synthetic minimal intron. In some embodiments, the intronic sequence has a length of less than 100 nucleotides. In some embodiments, the intronic sequence may comprise one or more of the promoter derived nucleic acids.

In some embodiments, the synthetic polynucleotide is less than 250 base pairs in length. In some embodiments, the synthetic polynucleotide is less than 300 base pairs in length.

In particular embodiments, the polynucleotide has a sequence selected from the group consisting of SEQ ID NOs:32, 33, 34, and 35 or a synthetic polynucleotide having at least 90% identity therewith. In some embodiments, the polynucleotide has a sequence selected from the group consisting of SEQ ID NO:32-25, SEQ ID NO:46-52, SEQ ID NO:59-66, and SEQ ID NO:70-72.

In some embodiments, the synthetic polynucleotide promotes liver-specific transgene expression. In some embodiments, the synthetic polynucleotide is suitable for promoting liver-specific transgene expression at a level at least 1.5-fold greater than an LP1 promoter. In some embodiments, the synthetic polynucleotide is suitable for promoting liver-specific transgene expression at a level at least 2-fold greater than an LP1 promoter.

In some embodiments, the synthetic polynucleotides further comprise an operably linked nucleic acid sequence encoding a posttranslational regulatory element.

In some embodiments, the synthetic polynucleotides further comprise an operably linked nucleic acid sequence encoding polyA element.

In some embodiments, the synthetic polynucleotides further comprise an operably linked transgene. In some embodiments, the transgene encodes AAT, AGXT, ARG, ASL, ASS, ATP7B, BCKDHA, BCKDHB, CFH, CFTF, CPS, DBT, FAH, FIX, FVIII, HAMP, HFE, JH, MUT, NAGS, OTC, PCCA, PCCB, PI, SLC40A1, TFR2, TTR, UGT1A1, Urokinase, PXBP, or variants, derivatives or equivalents thereof. In some embodiments, the transgene is a suicide gene.

In some embodiments, the polynucleotide has a sequence selected from the group consisting of SEQ ID Nos: 36, 37, 38, 39, and 40.

In accordance with some embodiments, there are provided expression cassettes comprising a synthetic polynucleotide according to any one of the embodiments described herein and an operably linked polynucleotide sequence encoding a transgene, wherein the transgene encodes a therapeutic polypeptide suitable for use in treating a disease or condition associated with the liver.

In some embodiments, the expression cassettes further comprise a nucleic acid encoding a posttranscriptional regulatory element.

In some embodiments, the expression cassettes further comprise a nucleic acid encoding a polyA element.

In accordance with some embodiments, there are provided gene therapy vectors comprising any one of the synthetic polynucleotides described herein and/or an expression cassette according to any one of the embodiments described herein.

In some embodiments, the vector is a retroviral vector, a lentiviral vector, an adenoviral vector, or an adeno-associated viral vector (AAV). In some embodiments, the vector is an AAV vector. In some embodiments, the AAV has a serotype suitable for liver transduction. In some embodiments, the AAV is selected from the group consisting of: AAV2, AAV5, AAV6, AAV7, AAV8, AAV9, AAV6.2, AAVrh.64R1, AAVhu.37, AAVrh.8, AAVrh.32.33, AAV3B, and LK03.

In accordance with some embodiments, there are provided recombinant viral particles comprising any one of the synthetic polynucleotides described herein, an expression cassette as described herein, or a vector as described herein.

In accordance with some embodiments, there are provided methods of treating a genetic disease or condition in a subject in need thereof, the method comprising administering an expression cassette comprising any one of the synthetic polynucleotides described herein or a vector comprising an expression cassette, thereby expressing a therapeutic peptide in the subject's liver.

In some embodiments, the genetic disease or condition associated with the liver is selected from the group comprising but not limited to genetic cholestasis, Wilson's disease, hereditary hemochromatosis, tyrosinemia type 1, alpha-1 antitrypsin deficiency, argininosuccinic aciduria, liver cancer, glycogen storage disease, urea cycle disorder, Crigler-Najjar syndrome, familial amyloid polyneuropathy, atypical hemolytic uremic syndrome-1, primary hyperoxaluria type 1, maple syrup urine disease, acute intermittent porphyria, coagulation defects, GSD type1A, homozygous familial hypercholesterolemia, organic acidurias, cystic fibrosis, erythropoietic protoporphyria, Gaucher disease, hemophilia A, hemophilia B, familial hypercholesterolemia, ornithine transcarbamylase deficiency, and phenylketonuria.

In some embodiments, the subject is a mammal. In some embodiments, the mammal is a human.

In accordance with some embodiments, there are provided methods of expressing a transgene in a liver cell, the method comprising contacting the liver cell with an expression cassette comprising any one of the synthetic polynucleotides described herein or a vector comprising an expression cassette.

In accordance with some embodiments, there are provided synthetic nucleic acid sequences according to any one the embodiments described herein, an expression cassette comprising a synthetic nucleic acid sequences according to any one the embodiments described herein, or a vector comprising an expression cassette, for use in a medical treatment of a genetic disease or condition. In some embodiments, the genetic disease or condition associated with the liver is selected from the group comprising but not limited to genetic cholestasis, Wilson's disease, hereditary hemochromatosis, tyrosinemia type 1, alpha-1 antitrypsin deficiency, argininosuccinic aciduria, liver cancer, glycogen storage disease, urea cycle disorder, Crigler-Najjar syndrome, familial amyloid polyneuropathy, atypical hemolytic uremic syndrome-1, primary hyperoxaluria type 1, maple syrup urine disease, acute intermittent porphyria, coagulation defects, GSD type1A, homozygous familial hypercholesterolemia, organic acidurias, cystic fibrosis, erythropoietic protoporphyria, Gaucher disease, hemophilia A, hemophilia B, familial hypercholesterolemia, ornithine transcarbamylase deficiency, and phenylketonuria. The foregoing general description and following detailed description are exemplary and explanatory and are intended to provide further explanation of the invention.

BRIEF DESCRIPTION OF THE DRAWINGS

FIG. 2 shows a selection of putative minimal promoter candidates namely APOC2 (SEQ ID NO: 9), SERPINE1 (SEQ ID NO: 7), G6PC (SEQ ID NO:10) and SERPINA1 (SEQ ID NO: 8). Putative TATA-box (shown in bold), initiator sequences (underlined) and TSS (shown in bold with double underling) elements are shown. SERPINA1 (SEQ ID NO: 8) minimal promoter sequence does not have a conventional TATA-box and the transcriptional start site derived from CAGE-seq experiments is marked by asterisks

FIG. 8A-B shows promoter activity in human primary hepatocytes. A. Shows relative light units (RLUs). B. Shows fold change over LP1.

FIG. 10A-B shows validation of activity of 5 identified promoters from secondary library screen. A. Shows RLUs. B. Shows fold change over LP1. Left bar HepG2 cells; right bar Huh7 cells.

FIG. 11A-B shows promoter activity of selected candidates in human primary hepatocytes. A. Shows RLUs. B. Shows fold change over LP1.

FIG. 13A-B shows confirmation of promoter activity in primary hepatocytes. A. Shows RLUs. B. Shows fold change over LP1.

FIG. 28 shows a diagram of #A2 (SEQ ID NO:36).
FIG. 31 shows a diagram of #C13 (SEQ ID NO:39).

DETAILED DESCRIPTION

Figure 1:
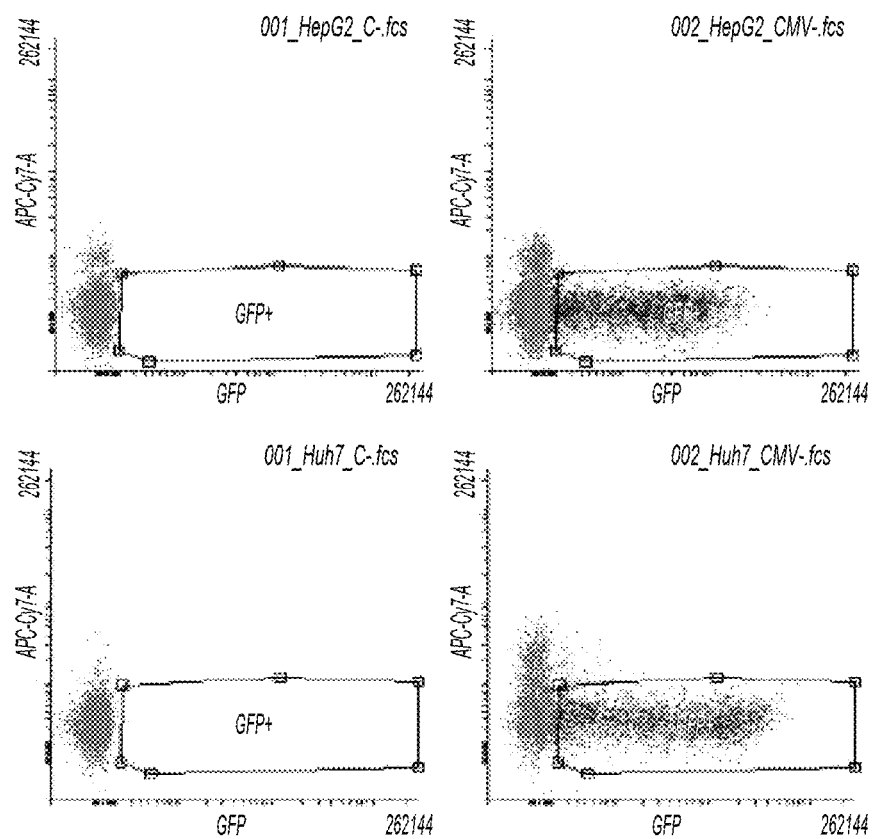
FIG. 1 shows an assessment of GFP expression in Huh7 and HepG2 cells by Fluorescence Activated Cell Sorting (FACS).

Described herein are liver-specific promoters, as well as AAV gene therapy vectors, therapeutic agents, and methods comprising the same.

The liver-specific promoters disclosed herein were derived one of two ways: (1) by rationally designing promoters, or (2) by screening a library of candidate promoters derived from randomized combinations of known liver associated promoter elements. As a result, the present inventors were able to develop novel promoters that are not only smaller than naturally-occurring promoter sequences, but also more active and specific for expression in the liver.

The disclosed compositions and methods may not be restricted to the treatment of the liver or liver diseases. Rather, the disclosed compositions and methods may provide a benefit in treating numerous types of disease in which a systemic protein (a protein present in the blood) is mutated or aberrantly expressed. By subjecting the patient to the methods of the invention, the availability of therapeutic molecules as expressed by the liver can be improved thereby allowing more efficient transduction and/or lower amounts of AAV administered.

As discussed in more detail below, the type of AAV gene therapy vector used in combination with the disclosed promoters is not particularly limited, and may include AAVs from various serotypes, as well as recombinant or chimeric AAVs.

The applications of the disclosed methods and promoters are far-reaching, and may be useful in improving the safety and efficacy of numerous gene therapy applications, as discussed in more detail below.

Throughout and within this application technical and patent literature are referenced by a citation. For certain of these references, the identifying citation is found at the end of this application immediately preceding the claims. All publications are incorporated by reference into the present disclosure to more fully describe the state of the art to which this disclosure pertains.

Definitions

As used in the description of the invention, clauses, and clauses appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the "administration" of an agent (e.g., a synthetic polynucleotide, expression cassette, viral particle, vector, polynucleotide, cell, population of cells, composition, or pharmaceutical composition) to a subject includes any route of introducing or delivering to a subject the agent to perform its intended function. Administration can be carried out by any suitable route, including orally, intranasally, intraocularly, ophthalmically, parenterally (intravenously, intramuscularly, intraperitoneally, or subcutaneously), or topically. Administration includes self-administration and the administration by another.

The term "cell" as used herein refers to a prokaryotic or eukaryotic cell. In some embodiments, the cell is a eukaryotic cell, optionally obtained from a subject or a commercially available source. In some embodiments, the cell is an isolated cell.

As used herein, the phrases "therapeutically effective amount" means a dose or plasma concentration in a subject that provides the specific pharmacological effect for which the disclosed AAV gene therapy vectors are administered, e.g. to express a therapeutic gene or gene of interest in a target cell/organ. It is emphasized that a therapeutically effective amount or therapeutic level of an AAV vector will not always be effective in treating the conditions described herein, even though such dosage is deemed to be a therapeutically effective amount by those of skill in the art. For convenience only, exemplary dosages, drug delivery amounts, and therapeutically effective amounts are provided below. Those skilled in the art can adjust such amounts in accordance with standard practices as needed to treat a specific subject and/or condition. The therapeutically effective amount may vary based on the route of administration and dosage form, the age and weight of the subject, and/or the disease or condition being treated.

As used herein, the terms "treatment" or "treating" refer to reducing, ameliorating or eliminating one or more signs, symptoms, or effects of a disease or condition (e.g., increasing expression of a coagulation factor in a subject with hemophilia, or decreasing expression of a gene is an associated with a disease, e.g. via inducing RNA interference etc.).

The terms "individual," "subject," and "patient" are used interchangeably herein, and refer to any individual subject with a disease or condition in need of treatment. For the purposes of the present disclosure, the subject may be a primate, such as a human primate, or another mammal, such as a dog, cat, horse, pig, goat, or bovine, and the like.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The terms also refer to both double- and single-stranded molecules. Unless otherwise specified or required, any embodiment of this invention that is a polynucleotide encompasses both the double-stranded form and each of two complementary single-stranded forms known or predicted to make up the double-stranded form.

"Homology" or "identity" or "similarity" refer to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+SwissProtein+SPupdate+ PIR. Details of these programs can be found at the following Internet address: ncbi.nlm.nih.gov/cgi-bin/BLAST.

An "equivalent" or "biological equivalent" nucleic acid, polynucleotide or oligonucleotide or peptide is one having at least 55% sequence identity, or alternatively at least 60% sequence identity, or alternatively at least 65% sequence identity, or alternatively at least 70% sequence identity, or alternatively at least 75% sequence identity, or alternatively at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to the reference nucleic acid, polynucleotide, oligonucleotide, promoter-derived nucleic acid, or peptide. In some embodiments, equivalents include a reverse complement of a reference nucleic acid, polynucleotide, oligonucleotide, or promoter-derived nucleic acid. In some embodiments, a biological equivalent of a reference element is a functional equivalent that comprises substantially the same function as the reference element.

For example, a biological equivalent of a particular promoter-derived nucleic acid that functions as a recognition or binding site for a particular effector molecule may comprise sequence variations but retains the ability to be recognized or bound by the same effector molecule. Equivalent function can be determined by any relevant means known in the art, including, but not limited to, electromobility shift assays (EMSA), binding assays, chromatin immunoprecipitation (ChIP), ChIP-sequencing (ChIP-seq), immunoprecipitation, and reporter gene expression systems. In a particular example, a biological equivalent of NRF2F1 is an element that is capable of being bound by the NRF2F1 protein, which can be determined by EMSA.

As used herein, the term "vector" refers to a non-chromosomal nucleic acid comprising an intact replicon such that the vector may be replicated when placed within a cell, for example by a process of transformation. Vectors may be viral or non-viral. Viral vectors include retroviruses, adenoviruses, herpesviruses, baculoviruses, modified baculoviruses, parvoviruses, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

A "viral vector" is defined as a recombinantly produced virus or viral particle that comprises a polynucleotide to be delivered into a host cell, either in vivo, ex vivo or in vitro. Examples of viral vectors include retroviral vectors, lentiviral vectors, adenovirus vectors, adeno-associated virus vectors (AAV), alphavirus vectors and the like. Viral vectors suitable for therapeutic use preferably do not express any viral vector proteins, i.e. the vector genome comprises all the genetic elements required for efficient replication and packaging of the vector genome in a viral capsid/envelope, but preferably do not contain genetic elements derived from the wild-type virus that produces viral proteins, as viral proteins may be associated with pathogenicity and/or can induce undesired immune responses. Alphavirus vectors, such as Semliki Forest virus-based vectors and Sindbis virus-based vectors, have also been developed for use in gene therapy and immunotherapy. See Schlesinger and Dubensky (1999) Curr. Opin. Biotechnol. 5:434-439; Ying, et al. (1999) Nat. Med. 5 (7): 823-827.

The term "promoter" refers to a regulatory region of a nucleic acid that initiates transcription. In some embodiments, a promoter can be constitutive or inducible. A constitutive promoter refers to one that is always active and/or constantly directs transcription of a gene above a basal level of transcription. An inducible promoter is one which is capable of being induced by a molecule or a factor added to the cell or expressed in the cell. An inducible promoter may still produce a basal level of transcription in the absence of induction, but induction typically leads to significantly more production of the protein. In some embodiments, promoters are tissue specific. A tissue specific promoter allows for transcription in a certain population of cells.

Synthetic Polynucleotides

The synthetic polynucleotides of the present disclosure comprise one or more promoter-derived nucleic acids. A "promoter-derived nucleic acid" is a nucleic acid comprising a nucleic acid sequence either (i) comprising all or part of the sequence of a known promoter; or (ii) demonstrated or known to have at least some promoter function.

In some embodiments, the synthetic polynucleotides comprise 3 or more promoter-derived nucleic acids. In some embodiments, the synthetic polynucleotides comprise 4 or more promoter-derived nucleic acids. In some embodiments, the synthetic polynucleotides comprise 5 or more promoter-derived nucleic acids. In some embodiments, the synthetic polynucleotides comprise 6 or more promoter-derived nucleic acids. In some embodiments, the synthetic polynucleotides comprise 7 or more promoter-derived nucleic acids. In some embodiments, the synthetic polynucleotides comprise 8 or more promoter-derived nucleic acids. In some embodiments, the synthetic polynucleotides comprise 9 or more promoter-derived nucleic acids. In some embodiments, the synthetic polynucleotides comprise 10 or more promoter-derived nucleic acids. Non-limiting, exemplary promoter elements are provided as SEQ ID NOs:1-19 and described in Table 1.

In some embodiments, the one or more promoter-derived nucleic acids are combined with a minimal promoter element, such as a "TATA box". The promoter elements do not necessarily require a transcription start site because the minimal promoter sequence provide for transcriptional start. An exemplary minimal promoter element may be selected from the group consisting of APOC2 (SEQ ID NO:9), SERPINA1_mp (SEQ ID NO:8), SERPINE1_mp (SEQ ID NO:7), G6PC (SEQ ID NO:10), and biological equivalents of each thereof.

In accordance with some embodiments, there are provided synthetic polynucleotides comprising at least three promoter-derived nucleic acids selected from the group consisting of: HNF1/HNF3 (SEQ ID NO:1); HNF3/HNF3 (SEQ ID NO:2); c/EBP/HNF4 (SEQ ID NO:3); HS_CRM2/HNF3 (SEQ ID NO:4); and HS_CRM8 (SEQ ID NO:6) or a variant thereof.

In accordance with some embodiments, there are provided synthetic polynucleotides comprising at least four promoter-derived nucleic acids selected from the group consisting of: HNF1/HNF3 (SEQ ID NO:1); HNF3/HNF3 (SEQ ID NO:2); c/EBP/HNF4 (SEQ ID NO:3); HS_CRM2/HNF3 (SEQ ID NO:4); and HS_CRM8 (SEQ ID NO:6) or a variant thereof.

In accordance with some embodiments, there are provided synthetic polynucleotides comprising HNF1/HNF3 (SEQ ID NO:1) and at least three promoter-derived nucleic acids selected from the group consisting of: HNF3/HNF3 (SEQ ID NO:2); c/EBP/HNF4 (SEQ ID NO:3); HS_CRM2/HNF3 (SEQ ID NO:4); and HS_CRM8 (SEQ ID NO:6) or a variant thereof.

In accordance with some embodiments, there are provided synthetic polynucleotides comprising c/EBP/HNF4 (SEQ ID NO:3) and at least three promoter-derived nucleic acids selected from the group consisting of: HNF1/HNF3

(SEQ ID NO:1); HNF3/HNF3 (SEQ ID NO:2); HS_CRM2/ HNF3 (SEQ ID NO:4); and HS_CRM8 (SEQ ID NO:6) or a variant thereof.

In accordance with some embodiments, there are provided synthetic polynucleotides comprising HNF1/HNF3 (SEQ ID NO:1) and c/EBP/HNF4 (SEQ ID NO:3); and at least two promoter-derived nucleic acids selected from the group consisting of: HNF3/HNF3 (SEQ ID NO:2); HS_CRM2/HNF3 (SEQ ID NO:4); and HS_CRM8 (SEQ ID NO:6) or a variant thereof.

In some embodiments, the synthetic polynucleotides comprise all five of the promoter-derived nucleic acids. In some embodiments, full exemplary promoter sequences may comprise one or more of SEQ ID NOs:21-31.

In some embodiments, a variant of the HS_CRM8 sequence is selected from the group consisting of SEQ ID NO:5, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, and equivalents of each thereof.

In some embodiments, a liver-specific promoter is provided comprising a variant of the HS_CRM8 sequence selected from the group consisting of SEQ ID NO:5, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, and equivalents of each thereof.

The HS_CRM8 sequence represents a composite element, as shown in the examples, and as listed above variants were made which were shown to have substantially the same activity when comprised in a liver specific promoter. Also, deleting this element strongly reduced liver gene expression. Hence, a liver specific promoter in accordance with the invention, instead of or in addition to comprising a variant of the HS_CRM8 sequence, may also be defined as comprising SEQ ID NO:101 (ACT-TAGCCCCTGTTTGCTCCTCCG), and/or SEQ ID NO:102 (TGACCTTGGTTAATATTCACCAGC), preferably SEQ ID NO:101 and SEQ ID NO:102. It is understood that such a liver specific promoter in accordance with the invention may also comprise variants of SEQ ID NO:101 and/or SEQ ID NO:102, or the reverse complement of one or both thereof. Hence, wherever in the description herein SEQ ID NO:5 is included in a liver specific promoter, alternatively to SEQ ID NO:5, said promoter can be defined to include SEQ ID NO:101 and/or SEQ ID NO:102, or a functional equivalent to SEQ ID NO:101 and/or SEQ ID NO:102, or the reverse complement of one or both thereof. As shown in the examples, many functional equivalents from the perspective of promoter activity could be made, i.e. having very similar activity, thereto. For example, SEQ ID NO:101 may have the sequence corresponding with SEQ ID NO:105 replaced with SEQ ID NO:107. Furthermore, SEQ ID NO:1 may have the sequence TCCG replaced with the sequence TTAG. It is also understood that functional equivalents may also have the sequence corresponding with SEQ ID NO:105 as a reverse complementary sequence instead, likewise, the same may apply to TCCG.

Furthermore, as also shown in the examples, many of the variants made of SEQ ID NO:5 resulted in promoters having very similar activity as compared to SEQ ID NO:5, albeit slightly reduced, while still retaining substantial improvement of activity as compared with LP1. Hence, a variant of the HS_CRM8 may also be defined as being a composite element comprising SEQ ID NO:101 and a sequence selected from the group consisting of SEQ ID NO:102, SEQ ID NO:104 (TGGTTAATATTCACCAGC), SEQ ID NO:106 (TGACCTTGGTTAATATTCACCA); or a composite element comprising SEQ ID NO:103 (CCCTGTTTGCTCCTCCG) and a sequence selected from the group consisting of SEQ ID NO:102, SEQ ID NO:104 (TGGTTAATATTCACCAGC), SEQ ID NO:106 (TGACCTTGGTTAATATTCACCA); or a composite element comprising SEQ ID NO:105 (CCCTGTTTGCTCC) and sequence TCCG, and a sequence selected from the group consisting of SEQ ID NO:102, SEQ ID NO:104 (TGGTTAATATTCACCAGC), SEQ ID NO:106 (TGACCTTGGTTAATATTCACCA); or a composite element comprising SEQ ID NO:105 and sequence TTAG, and a sequence selected from the group consisting of SEQ ID NO:102, SEQ ID NO:104 (TGGTTAATATTCACCAGC), SEQ ID NO:106 (TGACCTTGGTTAATATTCACCA); or a composite element comprising SEQ ID NO:107 (CCCTAT-TTACTCC) and sequence TCCG, and a sequence selected from the group consisting of SEQ ID NO:102, SEQ ID NO:104 (TGGTTAATATTCACCAGC), SEQ ID NO:106 (TGACCTTGGTTAATATTCACCA); or a composite element comprising SEQ ID NO:107 and sequence TTAG, and a sequence selected from the group consisting of SEQ ID NO:102, SEQ ID NO:104 (TGGTTAATATTCACCAGC), SEQ ID NO:106 (TGACCTTGGTTAATATTCACCA). It is understood that said variants of HS_CRM8 preferably have a sequence length which is less than 60 nucleotides. It is understood that the components comprised in the composite elements as defined herein may also be replaced with a reverse complementary sequence of SEQ ID NOs:101, 102, 103, 104, 105, 106, 107, TTAG, and TCCG.

In accordance with some embodiments, there are provided synthetic polynucleotides comprising at least a portion of a sequence comprising at least 75%, at least 80%, at least 85%, at least 90%, at least 95%, at least 97%, at least 98%, or at least 99% identity with HS_CRM8 or wild-type CRM8.

Use of HS_CRM8 variants as disclosed herein is not restricted to synthetic polynucleotides such as described, e.g., in the example section, but may also be useful for novel liver-specific promoters and/or liver-specific promoters as described in the prior art that comprise a CRM8 sequence. In the latter case, the HS_CRM8 variant sequences as described herein (e.g. SEQ ID NOs:5 and 87-99, or the recited variants comprising various combinations of SEQ ID NOs:101 to 107) suitably serve to replace some or all of the CRM8 sequence present in the prior art promoter. This way, size reduction and/or increase in liver-specific gene expression and/or liver selectivity may be achieved as compared with a wild-type CRM8 sequence (SEQ ID NO:6 or SEQ ID NO:100).

Accordingly, in accordance with some embodiments of the invention there is provided a synthetic liver-specific promoter comprising HS_CRM8 variant as set out above (e.g. SEQ ID NOs:5 and 87-99, or the recited variants comprising various combinations of SEQ ID NOs:101 to 107), or a sequence which is at least 75%, at least 80%, at least 85%, at least 90%, at least 95%, at least 97%, at least 98%, or at least 99% identity with any of the recited HS_CRM8 variants.

There is further provided an expression cassette, vector (e.g. gene therapy vector, such as an AAV vector), recombinant viral particle, or pharmaceutical composition comprising a synthetic liver-specific promoter comprising such an HS_CRM8 variant.

There are also provided methods of treating a genetic disease or condition in a subject in need thereof, the method comprising administering an expression cassette comprising a synthetic liver-specific promoter comprising such an HS_CRM8 variant, or a vector comprising such an expression cassette, thereby expressing a therapeutic peptide in the subject's liver. Further optional or preferred details of such a method are set out elsewhere in the disclosure.

There are also provided methods of expressing a transgene in a liver cell, the method comprising contacting the liver cell with an expression cassette comprising a synthetic liver-specific promoter comprising such an HS_CRM8 variant, or a vector comprising such an expression cassette. Further optional or preferred details of such a method are set out elsewhere in the disclosure.

There are also provided such an HS_CRM8 variant, expression cassette, vector (e.g. gene therapy vector, such as an AAV vector), recombinant viral particle, pharmaceutical composition comprising a synthetic liver-specific promoter comprising such a CRM8 variant for use in a medical treatment of a genetic disease or condition. Various specific diseases and optional and preferred details of such a use are discussed elsewhere in the application.

In accordance with some embodiments, there are provided synthetic polynucleotides having at least 75%, at least 80%, at least 85%, at least 90%, at least 95%, at least 97%, at least 98%, or at least 99% identity with a synthetic polynucleotide comprising at least three promoter-derived nucleic acids selected from the group consisting of: HNF1/HNF3 (SEQ ID NO:1); HNF3/HNF3 (SEQ ID NO:2); c/EBP/HNF4 (SEQ ID NO:3); HS_CRM2/HNF3 (SEQ ID NO:4); and HS_CRM8 (SEQ ID NO:6) or a variant thereof. In some embodiments, there are provided synthetic polynucleotides that are biological equivalents of synthetic polynucleotides comprising at least three promoter-derived nucleic acids selected from the group consisting of: HNF1/HNF3 (SEQ ID NO:1); HNF3/HNF3 (SEQ ID NO:2); c/EBP/HNF4 (SEQ ID NO:3); HS_CRM2/HNF3 (SEQ ID NO:4); and HS_CRM8 (SEQ ID NO:6) or a variant thereof.

In some embodiments, the synthetic polynucleotides comprise consecutively from the 5' end to 3' end SEQ ID NO:1, SEQ ID NO:2, SEQ ID NO:3, SEQ ID NO:4, and SEQ ID NO:6, or an equivalent of each thereof.

In some embodiments, the promoter derived nucleic acids are operably linked.

In some embodiments, the synthetic polynucleotides further comprise at least one minimal promoter nucleic acid. Non-limiting examples of a suitable minimal promoter nucleic acid include SERPINE1 (SEQ ID NO:7), SERPINA1 (SEQ ID NO:8), APOC2 (SEQ ID NO:9), or G6PC (SEQ ID NO:10), or an equivalent of each thereof. In some embodiments, the equivalent minimal promoter nucleic acid is a minimal promoter nucleic acid having at least 75%, at least 80%, at least 85%, at least 90%, at least 95%, at least 97%, at least 98%, or at least 99% identity sequence identity with SERPINE1 (SEQ ID NO:7), SERPINA1 (SEQ ID NO:8), APOC2 (SEQ ID NO:9), or G6PC (SEQ ID NO:10). In some embodiments, the equivalent minimal promoter nucleic acid is a biological equivalent of SERPINE1 (SEQ ID NO:7), SERPINA1 (SEQ ID NO:8), APOC2 (SEQ ID NO:9), or G6PC (SEQ ID NO:10). In some embodiments, the minimal promoter nucleic acid comprises a sequence selected from the group consisting of: SEQ ID NOs:7, 8, 9 and 10.

In accordance with some embodiments, there are provided synthetic polynucleotides having at least 75%, at least 80%, at least 85%, at least 90%, at least 95%, at least 97%, at least 98%, or at least 99% identity with a synthetic polynucleotide comprising four or five different promoter-derived nucleic acids selected from the group consisting of: HNF1/HNF3 (SEQ ID NO:1); HNF3/HNF3 (SEQ ID NO:2); c/EBP/HNF4 (SEQ ID NO:3); HS_CRM2/HNF3 (SEQ ID NO:4); and HS_CRM8 (SEQ ID NO:6) or a variant thereof, and a suitable minimal promoter nucleic acid include SERPINE1 (SEQ ID NO:7), SERPINA1 (SEQ ID NO:8), APOC2 (SEQ ID NO:9), or G6PC (SEQ ID NO:10). In some embodiments, there are provided synthetic polynucleotides that are biological equivalents of synthetic polynucleotides comprising four or five different promoter-derived nucleic acids selected from the group consisting of: HNF1/HNF3 (SEQ ID NO:1); HNF3/HNF3 (SEQ ID NO:2); c/EBP/HNF4 (SEQ ID NO:3); HS_CRM2/HNF3 (SEQ ID NO:4); and HS_CRM8 (SEQ ID NO:6) or a variant thereof, and a suitable minimal promoter nucleic acid include SERPINE1 (SEQ ID NO:7), SERPINA1 (SEQ ID NO:8), APOC2 (SEQ ID NO:9), or G6PC (SEQ ID NO:10).

In some embodiments, the orientation of at least one of the promoter-derived nucleic acids (not including the minimal promoter element, as this element relates to transcription initiation) is inverted. In some embodiments, the synthetic polynucleotides comprise a reverse complement of at least one of the promoter-derived nucleic acids described herein (not including the minimal promoter element, as this element relates to transcription initiation).

In some embodiments, the synthetic polynucleotides further comprise at least one spacer nucleic acid located between two of the promoter-derived nucleic acids or between a promoter-derived nucleic acid and an ITR. Such a spacer nucleic acid may not code for a transcription factor binding sequence and may be merely random sequences and/or sequences that do not affect the DNA structure but allow the two promoter-derived nucleic acids to exert their function, i.e. both binding their respective transcription factor. Such a spacer nucleic acid may be one, two, three, four or more nucleotides or base pairs. In some embodiments, the spacer nucleic acid is 1-20, 1-10, 1-5, 1-4, 1-3, or 1-2 nucleotides or base pairs in length. In some embodiments, the space may be 1-200, 1-150, 1-100, 1-50, 5-150, 10-100, 15-75, or 20-50 nucleotides or base pairs in length or any number of nucleotides or base pairs in between. For instance, a space may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more nucleotides or base pairs. Such spacer sequences are excluded from sequence identity calculations, i.e. when a synthetic polynucleotide according to the invention contains the promoter elements and minimal promoter sequence as defined herein, sequence identity is preferably calculated with respect to the defined promoter elements and minimal promoter sequences alone, and does not include the spacer element(s).

A non-limiting example of a synthetic polynucleotide comprising a spacer is found in SEQ ID NO:26. The spacer nucleotides are underlined in SEQ ID NO:26. In some embodiments, a biological equivalent of SEQ ID NO:26 is a synthetic polynucleotide comprising SEQ ID NO:26 with one or more of the spacer nucleotides removed.

In some embodiments, the synthetic polynucleotides further comprise an operably linked nucleic acid sequence encoding an intron. In some embodiments, the intron is derived from SV40. In some embodiments the intron is derived from MVM. In some embodiments the intron is a synthetic intron sequence. In some embodiments, the intronic sequence has a length of less than 1000, less than 900 nucleotides, less than 800 nucleotides, less than 700 nucleotides, less than 600 nucleotides, less than 500 nucleotides, less than 400 nucleotides, less than 300 nucleotides, less than 200 nucleotides, less than 100 nucleotides, less than 90 nucleotides, less than 80 nucleotides, less than 70 nucleotides, less than 60 nucleotides, less than 50 nucleotides, less than 40 nucleotides, less than 30 nucleotides, less than 20 nucleotides, less than 10 nucleotides, or less than 5 nucleotides. In some embodiments, the intronic sequence is between 5 nucleotides and 200 nucleotides, between 5 nucleotides and 150 nucleotides, between 10 nucleotides and 125 nucleotides, or between 10 nucleotides and 100 nucleotides. In some embodiments, the intronic sequence may comprise one or more of the promoter-derived nucleic acids.

In some embodiments, the polynucleotide has a sequence selected from the group consisting of SEQ ID NOs:21, 22, 23, 24, 25, 26, 27, 28, 29, 30, 31, 42, and equivalents of each thereof. In some embodiments, the polynucleotide has a sequence selected from the group consisting of SEQ ID NOs:42-46; 54-59; 68-70; 74-86, and equivalents of each thereof.

In some embodiments, the synthetic polynucleotide promotes transgene expression in the liver, preferably liver-specific transgene expression. In some embodiments, the synthetic polynucleotide is suitable for promoting liver-specific transgene expression at a level at least 1.5 fold greater than an LP1 promoter. In some embodiments, the synthetic polynucleotide is suitable for promoting liver-specific transgene expression at a level at least 2 fold greater than an LP1 promoter. In some embodiments, the synthetic polynucleotide is suitable for promoting liver-specific transgene expression at a level at least 3 fold, 4 fold, 5 fold, 6 fold, 7 fold, 8 fold, 9 fold, 10 fold, 15 fold, 20 fold, 25 fold, 30 fold, 40 fold or 50 fold greater than an LP1 promoter, e.g. such as shown in the example section in Huh7 transfection and/or AAV transduction of Huh7 cells, or as determined by transgene expression in an animal when comparing LP1 with a synthetic polynucleotide of the invention. In some embodiments, the synthetic polynucleotide has reduced transgene expression at a level of at least 1.5 fold, 2 fold, 3 fold, 4 fold, 5 fold, 6 fold, 7 fold, 8 fold, 9 fold, 10 fold, 15 fold, 20 fold, 25 fold, 30 fold, 40 fold or 50 fold less than an LP1 promoter in non-liver derived cells. A non-limiting example of non-liver derived cells are A549 cells.

In some embodiments, the synthetic polynucleotide is suitable for promoting liver-specific transgene expression at a level at least 4 fold greater than a CMV promoter. In some embodiments, the synthetic polynucleotide is suitable for promoting liver-specific transgene expression at a level at least 2 fold, 3 fold, 4 fold, 5 fold, 6 fold, 7 fold, 8 fold, 9 fold, 10 fold, 15 fold, 20 fold, 25 fold, 30 fold, 40 fold or 50 fold greater than a CMV promoter in liver-derived cells. In some embodiments, the synthetic polynucleotide has reduced transgene expression at a level of at least 1.5 fold, 2 fold, 3 fold, 4 fold, 5 fold, 6 fold, 7 fold, 8 fold, 9 fold, 10 fold, 15 fold, 20 fold, 25 fold, 30 fold, 40 fold or 50 fold less than a CMV promoter in non-liver derived cells. A non-limiting example of non-liver derived cells are A549 cells.

In some embodiments, the synthetic polynucleotides further comprise an operably linked transgene. In some embodiments, the transgene encodes AAT, AGXT, ARG, ASL, ASS, ATP7B, BCKDHA, BCKDHB, CFH, CFTF, CPS, DBT, FAH, FIX, FVIII, HAMP, HFE, JH, MUT, NAGS, OTC, PCCA, PCCB, PI, SLC40A1, TFR2, TTR, UGT1A1, Urikinase, PXBP, or variants, derivatives or equivalents thereof.

In accordance with some embodiments, there are provided synthetic polynucleotides comprising at least three promoter-derived nucleic acids selected from the group consisting of: Motif_44 (SEQ ID NO:12); NRF2F1 (SEQ ID NO:14); HNF1A (SEQ ID NO:15); IA2 (SEQ ID NO:16); and a biological equivalent of each thereof.

In accordance with some embodiments, there are provided synthetic polynucleotides comprising at least three promoter-derived nucleic acids selected from the group consisting of: Motif_44 (SEQ ID NO:12); NRF2F1 (SEQ ID NO:14); HNF1A (SEQ ID NO:15); and IA2 (SEQ ID NO:16); SEQ ID NO:33; SEQ ID NO:35; and biological equivalents of each thereof. In accordance with some embodiments, there are provided synthetic polynucleotides having at least 75%, at least 80%, at least 85%, at least 90%, at least 95%, at least 97%, at least 98%, or at least 99% identity with a synthetic polynucleotide comprising at least three promoter-derived nucleic acids selected from the group consisting of: Motif_44 (SEQ ID NO:12); NRF2F1 (SEQ ID NO:14); HNF1A (SEQ ID NO:15); and IA2 (SEQ ID NO:16); SEQ ID NO:33; and SEQ ID NO:35.

In some embodiments, the synthetic polynucleotides comprise consecutively from the 5' to 3' SEQ ID NO:12, SEQ ID NO:15, and SEQ ID NO:16. In some embodiments, SEQ ID NO:14 is 3' to SEQ ID NO:15. In some embodiments, SEQ ID NO:14 is 5' to SEQ ID NO:15.

In some embodiments, the synthetic polynucleotides further comprise one or more sequences selected from: (e) HNF1B (SEQ ID NO:11); (f) JUN/FOS (SEQ ID NO:17); (g) HNF4A (SEQ ID NO:18); (h) SPI1 (SEQ ID NO:19), or a biological equivalent of each thereof.

In some embodiments, the synthetic polynucleotides comprise consecutively from 5' to 3': SEQ ID NO:11, SEQ ID NO:12, SEQ ID NO:14, SEQ ID NO:15, SEQ ID NO:14, SEQ ID NO:12, and SEQ ID NO:16. In some embodiments, the synthetic polynucleotides comprise consecutively from 5' to 3': SEQ ID NO:15, SEQ ID NO:17, SEQ ID NO:18, SEQ ID NO:19, SEQ ID NO:14, SEQ ID NO:12, SEQ ID NO:15, and SEQ ID NO:16.

In some embodiments, the synthetic polynucleotides further comprise at least one minimal promoter nucleic acid. In some embodiments, the sequence of the minimal promoter nucleic acid is derived from SERPINE1 (SEQ ID NO:7), SERPINA1 (SEQ ID NO:8), APOC2 (SEQ ID NO:9), G6PC (SEQ ID NO:10), or a biological equivalent of each thereof, or a minimal promoter nucleic acid having at least 75%, at least 80%, at least 85%, at least 90%, at least 95%, at least 97%, at least 98%, or at least 99% identity sequence identity with SERPINE1 (SEQ ID NO:7), SERPINA1 (SEQ ID NO:8), APOC2 (SEQ ID NO:9), or G6PC (SEQ ID NO:10). In some embodiments, the minimal promoter nucleic acid comprises a sequence selected from the group consisting of: SEQ ID NOs:7, 8, 9 and 10.

In some embodiments, the synthetic polynucleotides comprise consecutively from 5' to 3': SEQ ID NO:11, SEQ ID NO:12, SEQ ID NO:14, SEQ ID NO:15, SEQ ID NO:14, SEQ ID NO:12, and SEQ ID NO:16, or the synthetic polynucleotides comprise consecutively from 5' to 3': SEQ ID NO:15, SEQ ID NO:17, SEQ ID NO:18, SEQ ID NO:19, SEQ ID NO:14, SEQ ID NO:12, SEQ ID NO:15, and SEQ ID NO:16; followed by a minimal promoter nucleic acid derived from SERPINE1 (SEQ ID NO:7), SERPINA1 (SEQ ID NO:8), APOC2 (SEQ ID NO:9), G6PC (SEQ ID NO:10), or a biological equivalent of each thereof, or a synthetic polynucleotide having at least 75%, at least 80%, at least 85%, at least 90%, at least 95%, at least 97%, at least 98%, or at least 99% sequence identity therewith.

In some embodiments, the synthetic polynucleotides further comprise an operably linked nucleic acid sequence encoding an intron. Non-limiting examples of introns include hCMV intron A, adenovirus tripartite leader sequence intron, SV40 intron, an MVM intron, Chinese hamster EF-1alpha gene intron 1 and intervening sequence intron. In some embodiments, the intron nucleic acid comprises a sequence derived from SV40. See, e.g. Xu et al. *J Cell Mol Med.* 2018 April; 22 (4): 2231-2239, for additional methods and descriptions of suitable intron sequences.

In some embodiments, the synthetic polynucleotide is about 20 to about 800 bp, about 40 to about 100 bp, about 50 to about 150 bp, about 60 to about 200 bp, about 80 to about 250 bp, about 90 to about 275 bp, about 100 to about 300 bp, about 50 to about 300 bp, about 100 to about 400 bp, about 100 to about 500 bp, about 100 to about 600 bp, about 100 to about 700 bp, about 200 to about 800 bp, or about 50 to about 1000 bp in length. In some embodiments, the length of the synthetic polynucleotide is less than about 1000, less than about 900, less than about 800, less than about 700, less than about 600, less than about 500, less than about 400, less than about 300, less than about 250, less than about 200 base pairs, or less than about 150 base pairs in length. In particular embodiments, the synthetic polynucleotide is less than 250 base pairs in length or less than 300 base pairs in length.

In particular embodiments, the polynucleotide has a sequence selected from the group consisting of SEQ ID NOs:21-31, 41-45, 53-58, 67-69 and 73-86, or a biological equivalent of each thereof, or a synthetic polynucleotide having at least 75%, at least 80%, at least 85%, at least 90%, at least 95%, at least 97%, at least 98%, or at least 99% sequence identity therewith.

In particular embodiments, the polynucleotide has a sequence selected from the group consisting of SEQ ID NOs:32-35, 46-52, 59-66, 70-72, or a biological equivalent of each thereof, or a synthetic polynucleotide having at least 75%, at least 80%, at least 85%, at least 90%, at least 95%, at least 97%, at least 98%, or at least 99% sequence identity therewith.

In some embodiments, the synthetic polynucleotides further comprise an operably linked nucleic acid sequence encoding a posttranslational regulatory element. Non-limiting examples of post translational regulatory elements include 5'UTRs, 3'UTRs, and polyA elements. In some embodiments, the synthetic polynucleotides further comprise an operably linked nucleic acid sequence encoding polyA element.

In some embodiments, the synthetic polynucleotides further comprise an operably linked transgene. In some embodiments, the transgene encodes AAT, AGXT, ARG, ASL, ASS, ATP7B, BCKDHA, BCKDHB, CFH, CFTF, CPS, DBT, FAH, FIX, FVIII, HAMP, HFE, JH, MUT, NAGS, OTC, PCCA, PCCB, PI, SLC40A1, TFR2, TTR, UGT1A1, Urikinase, PXBP or variants, derivatives or equivalents thereof.

In some embodiments, the transgene is a suicide gene. In some embodiments, the transgene is inducible. In some embodiments, the suicide gene is herpes simplex virus thymidine kinase ("HSV-tk") (GenBank Accession NO: AB45318.1 (nucleotides 3331-4458)). Other non-limiting examples of suicide genes include codon optimized TK or tk30, tk75 and sr39tk, described in Pantuck et al. (2004) Human Gene Therapy, Vol. 13 (7): 777-789; Black et al. (2001) Cancer Res. 61:3022-3026; and Ardiani, et al. (2010) Cancer Gene Therapy 17:86-96.

In some embodiments, the synthetic polynucleotides are encoded by DNA. In some embodiments, the synthetic polynucleotides are encoded by RNA, optionally viral RNA. The synthetic polynucleotides can be single stranded or double stranded. In some embodiments, the structural format of the synthetic polynucleotide (i.e., DNA or RNA, single stranded or double stranded) is determined by the applicable gene therapy vehicle used. For example, a lentiviral vector comprises a single stranded RNA genome. An AAV vector comprises either a single stranded DNA vector genome or a duplex DNA vector genome, which may depend on the size of the vector genome and/or vector genome design. When a lentiviral vector genome is reverse transcribed during transduction, the RNA sequence is converted into the corresponding DNA sequence.

In some embodiments, the synthetic polynucleotide has a sequence selected from the group consisting of SEQ ID Nos: 36, 37, 38, 39, 40, and a biological equivalent of each thereof, or a synthetic polynucleotide having at least 75%, at least 80%, at least 85%, at least 90%, at least 95%, at least 97%, at least 98%, or at least 99% sequence identity therewith.

In some embodiments, inclusion of the disclosed liver-specific promoters can increase expression of a therapeutic gene or gene of interest in the liver by at least 10%, at least 20%, at least 30%, at least 40%, at least 50%, at least 55%, at least 60%, at least 65%, at least 70%, at least 75%, at least 80%, at least 85%, at least 90%, or at least 95% or more compared to known non-specific promoters (e.g., wild-type CRM8). In some embodiments, the synthetic polynucleotides increase expression at least 1.2 fold-1.8 fold, 1.5 fold-2.5 fold, 2 fold-5 fold, 4 fold-10 fold, 5 fold-20 fold, or 10 fold-100 fold compared to the known promoter.

In some embodiments, inclusion of the disclosed liver-specific promoters can increase expression of a therapeutic gene or gene of interest in the liver by at least 10%, at least 20%, at least 30%, at least 40%, at least 50%, at least 55%, at least 60%, at least 65%, at least 70%, at least 75%, at least 80%, at least 85%, at least 90%, or at least 95% or more compared to a known liver-specific promoter (e.g., the LP-1 promoter). In some embodiments, the synthetic polynucleotides increase expression at least 1.2 fold-1.8 fold, 1.5 fold-2.5 fold, 2 fold-5 fold, 4 fold-10 fold, 5 fold-20 fold, or 10 fold-100 fold compared to a known liver-specific promoter.

Non-limiting examples of nucleic acid sequences suitable for use in the synthetic polynucleotides and synthetic polynucleotides of the present disclosure are provided in Tables 1, 2 and 3 below.

TABLE 1

SEQ ID NOs: 1-40

| SEQ ID NO: | Identity | Sequence |
| --- | --- | --- |
| 1 | HNF1/HNF3 at PROC | AAGCAAATATTTGTGGTTATGGATTAACTCGAA |
| 2 | HNF3/HNF3 at APOA1 | CTGTTTGCCCACTCTATTTGCCC |
| 3 | c/EBP/HNF4 at APOB | GGCGCCCTTTGGACCTTTTGCAATCCTGG |

TABLE 1-continued

SEQ ID NOs: 1-40

| SEQ ID NO: | Identity | Sequence |
|---|---|---|
| 4 | HS_CRM2 2x HNF3 | AGCAAACAGCAAACAC |
| 5 | HS_CRM8_full | GGACTTAGCCCCTGTTTGCTCCTCCGATAACTG GGGTGACCTTGGTTAATATTCACCAGCAGCCTC |
| 6 | HS_CRM8 | GCCCCTGTTTGCTCCTCCGATAACTGGGGTGAC CTTGGTTAATATTCACCA |
| 7 | SERPINE1_mp | TCATCTATTTCCTGCCCACATCTGGTATAAAAG GAGGCAGTGGCCCACAGAGGAGCACAGCTGTG |
| 8 | SERPINA1_mp (includes HS_CRM8_full) | GGGCGACTCAGATCCCAGCCAGTGGACTTAGC CCCTGTTTGCTCCTCCGATAACTGGGGTGACCT TGGTTAATATTCACCAGCAGCCTCCCCCGTTGC CCCTCTGGATCCACTGCTTAAATACGGACGAGG ACAGGGCCCTGTCTCCTCAGCTTCAGGCACCAC CACTGACCTGGGACAGTGAATC |
| 9 | APOC2 mp | GAGCGGAAGTGGGTCTCAACCACTATAAATCCT CTCTGTGCCCGTCCGGAGCTGGTGAGGACA |
| 10 | G6PC mp | GGGCATATAAAACAGGGGCAAGGCACAGACTC ATAGCAGAGCAATCACCACCAAGCCTGGAATA ACTGCAGCCACC |
| 11 | HNF1B | TTAATATTTAAC |
| 12 | Motif_44 | AGCTTCA |
| 13 | VSLEF1_Q5_01 | CCTTTGA |
| 14 | NRF2F1 | TGACCTTTGAACCT |
| 15 | HNF1A | GGTAATTATTAACC |
| 16 | IA2 | CTAGTAGCAAGGCTGACTACACGAGCACATAT CA |
| 17 | JUN/FOS | TGAGTCA |
| 18 | HNF4A | CTGGACTTTGGACTC |
| 19 | SPI1 | TCACTTCCTCTTTTT |
| 20 | LP1** | CCCTAAAATGGGCAAACATTGCAAGCAGCAAA CAGCAAACACACAGCCCTCCCTGCCTGCTGACC TTGGAGCTGGGGCAGAGGTCAGAGACCTCTCT GGGCCCATGCCACCTCCAACATCCACTCGACCC CTTGGAATTTCGGTGGAGAGGAGCAGAGGTTG TCCTGGCGTGGTTTAGGTAGTGTGAGAGGGGA ATGACTCCTTTCGGTAAGTGCAGTGGAAGCTGT ACACTGCCCAGGCAAAGCGTCCGGGCAGCGTA GGCGGGCGACTCAGATCCCAGCCAGTGGACTT AGCCCCTGTTTGCTCCTCCGATAACTGGGGTGA CCTTGGTTAATATTCACCAGCAGCCTCCCCCGT TGCCCCTCTGGATCCACTGCTTAAATACGGACG AGGACAGGGCCCTGTCTCCTCAGCTTCAGGCAC CACCACTGACCTGGGACAGTGAATCCGGACTCT AAGGTAAATATAAAATTTTAAGTGTATAATGT GTTAAACTACTGATTCTAATTGTTTCTCTCTTTT AGATTCCAACCTTTGGAACTGAATTCTAGACCA CC |
| 21 | APOC2_COMP_D | TAAAGCAAATATTTGTGGTTATGGATTAACTCG AACTTCTAGAAGCTGTTTGCCCACTCTATTTGC CCATCCAGGTAGGCGCCCTTTGGACCTTTTGC AATCCTGGCTTCTAGAAGAGCAAACAGCAAAC ACATCCTAGGTAGGACTTAGCCCCTGTTTGCTC CTCCGATAACTGGGGTGACCTTGGTTAATATTC ACCAGCAGCCTCATGCTAGCCTCGAGGATATCA GATCTGAGCGGAAGTGGGTCTCAACCACTATA AATCCTCTCTGTGCCCGTCCGGAGCTGGTGAGG ACAGCCACC |

TABLE 1-continued

| SEQ ID NO: | Identity | Sequence |
|---|---|---|
| 22 | APOC2_COMP_D_v1 | AAGCAAATATTTGTGGTTATGGATTAACTCGAA CTGTTTGCCCACTCTATTTGCCCGGCGCCCTTTG GACCTTTTGCAATCCTGGAGCAAACAGCAAAC ACGGACTTAGCCCCTGTTTGCTCCTCCGATAAC TGGGGTGACCTTGGTTAATATTCACCAGCAGCC TCATGAGCGGAAGTGGGTCTCAACCACTATAA ATCCTCTCTGTGCCCGTCCGGAGCTGGTGAGGA CAGCCACC |
| 23 | COMP_Synthetic_promoter_D | TAAAGCAAATATTTGTGGTTATGGATTAACTCG AACTTCTAGAAGCTGTTTGCCCACTCTATTTGC CCATCCTAGGTAGGCGCCCTTTGGACCTTTTGC AATCCTGGCTTCTAGAAGAGCAAACAGCAAAC ACATCCTAGGTAGGACTTAGCCCCTGTTTGCTC CTCCGATAACTGGGGTGACCTTGGTTAATATTC ACCAGCAGCCTCAT |
| 24 | COMP_Synthetic_promoter_D_V1 | TAAAGCAAATATTTGTGGTTATGGATTAACTCG AACTGTTTGCCCACTCTATTTGCCCGGCGCCCTT TGGACCTTTTGCAATCCTGGAGCAAACAGCAAA CACGGACTTAGCCCCTGTTTGCTCCTCCGATAA CTGGGGTGACCTTGGTTAATATTCACCAGCAGC CTCATGCCACC |
| 25 | G6PC_COMP_D | TAAAGCAAATATTTGTGGTTATGGATTAACTCG AACTTCTAGAAGCTGTTTGCCCACTCTATTTGC CCATCCTAGGTAGGCGCCCTTTGGACCTTTTGC AATCCTGGCTTCTAGAAGAGCAAACAGCAAAC ACATCCTAGGTAGGACTTAGCCCCTGTTTGCTC CTCCGATAACTGGGGTGACCTTGGTTAATATTC ACCAGCAGCCTCATGCTAGCCTCGAGGATATCA GATCTGGGCATATAAAACAGGGGCAAGGCACA GACTCATAGCAGAGCAATCACCACCAAGCCTG GAATAACTGCAGCCACC |
| 26 | G6PC_COMP_v1_D | AAGCAAATATTTGTGGTTATGGATTAACTCGAA CTGTTTGCCCACTCTATTTGCCCGGCGCCCTTTG GACCTTTTGCAATCCTGGAGCAAACAGCAAAC ACGGACTTAGCCCCTGTTTGCTCCTCCGATAAC TGGGGTGACCTTGGTTAATATTCACCAGCAGCC TCGGGCATATAAAACAGGGGCAAGGCACAGAC TCATAGCAGAGCAATCACCACCAAGCCTGGAA TAACTGCAGCCACC |
| 27 | G6PC_COMP_v1_D_v2 | AAGCAAATATTTGTGGTTATGGATTAACTCGAA GGCGCCCTTTGGACCTTTTGCAATCCTGGAGCA AACAGCAAACACGGCCCCTGTTTGCTCCTCCGA TAACTGGGGTGACCTTGGTTAATATTCACCAGC AGCCTCGGGCATATAAAACAGGGGCAAGGCAC AGACTCATAGCAGAGCAATCACCACCAAGCCT GGAATAACTGCAGCCACC |
| 28 | G6PC_COMP_v3 | AAGCAAATATTTGTGGTTATGGATTAACTCGAA CTGTTTGCCCACTCTATTTGCCCGGCGCCCTTTG GACCTTTTGCAATCCTGGAGCAAACAGCAAAC ACGCCCCTGTTTGCTCCTCCGATAACTGGGGTG ACCTTGGTTAATATTCACCAGGGCATATAAAAC AGGGGCAAGGCACAGACTCATAGCAGAGCAAT CACCACCAAGCCTGGAATAACTGCAGCCACC |
| 29 | SERPINA1_COMP_D | TAAAGCAAATATTTGTGGTTATGGATTAACTCG AACTTCTAGAAGCTGTTTGCCCACTCTATTTGC CCATCCTAGGTAGGCGCCCTTTGGACCTTTTGC AATCCTGGCTTCTAGAAGAGCAAACAGCAAAC ACATCCTAGGTAGGACTTAGCCCCTGTTTGCTC CTCCGATAACTGGGGTGACCTTGGTTAATATTC ACCAGCAGCCTCATGCTAGCCTCGAGGATATCA GATCTGGGCGACTCAGATCCCAGCCAGTGGACT TAGCCCCTGTTTGCTCCTCCGATAACTGGGGTG ACCTTGGTTAATATTCACCAGCAGCCTCCCCCG TTGCCCCTCTGGATCCACTGCTTAAATACGGAC GAGGACAGGGCCCTGTCTCCTCAGCTTCAGGCA CCACCACTGACCTGGGACAGTGAATCGCCACC |

TABLE 1-continued

SEQ ID NOs: 1-40

| SEQ ID NO: | Identity | Sequence |
|---|---|---|
| 30 | SERPINE1_mp | TAAAGCAAATATTTGTGGTTATGGATTAACTCG AACTTCTAGAAGCTGTTTGCCCACTCTATTTGC CCATCCTAGGTAGGCGCCCTTTGGACCTTTTGC AATCCTGGCTTCTAGAAGAGCAAACAGCAAAC ACATCCTAGGTAGGACTTAGCCCCTGTTTGCTC CTCCGATAACTGGGGTGACCTTGGTTAATATTC ACCAGCAGCCTCATGCTAGCCTCGAGGATATCA GATCTTCATCTATTTCCTGCCCACATCTGGTATA AAAGGAGGCAGTGGCCCACAGAGGAGCACAGC TGTGCCACC |
| 31 | SERPINE1_COMP_D_v1: | AAGCAAATATTTGTGGTTATGGATTAACTCGAA CTGTTTGCCCACTCTATTTGCCCGGCGCCCTTTG GACCTTTTGCAATCCTGGAGCAAACAGCAAAC ACGGACTTAGCCCCTGTTTGCTCCTCCGATAAC TGGGGTGACCTTGGTTAATATTCACCAGCAGCC TCATTCATCTATTTCCTGCCCACATCTGGTATAA AAGGAGGCAGTGGCCCACAGAGGAGCACAGCT GTGCCACC |
| 32 | #B4 | AAGTTAATATTTAACATCCTAGCACAGCTTCAC TTCCAGGTATGACCTTTGAACCTCTTCTAGAAG GGTAATTATTAACCTAGCTAGGTATGACCTTCG AACCTCTTCTAGAAGTGAAGCTATGCTAGTAGC AAGGCTGACTACACGAGCACATATCAACGCGT CGACGATATCAGATCTGGGCATATAAACAGGG GCAAGGCACAGACTCATAGCAGAGCAATTACC ACCAAGCCTGGAATAGCTGCAGCCACC |
| 33 | #B4_v1 | TTAATATTTAACATCCTAGCACAGCTTCACTTC CAGGTATGACCTTTGAACCTCTTCTAGAAGGGT AATTATTAACCTAGCTAGGTATGACCTTCGAAC CTCTTCTAGAAGTGAAGCTGGGCATATAAACAG GGGCAAGGCACAGACTCATAGCAGAGCAATTA CCACCAAGCCTGGAATAGCTGCAGCCACC |
| 34 | #C14 | TAGGTTAATAATTACCCTTCTAGGATTGAGTCA CTTCTAGAAGCTGGACTTTGGACTCATCCTAGA AGTCACTTCCTCTTTTTTACCTAGAAGAGGTTC AAAGGTCATACCTAGCATAGCTTCACTTCTAGA AGGGTAATTATTAACCTAGCTAGTAGCAAGGCT GACTACACGAGCACATATCAACGCGTCGACGA TATCAGATCTGGGCATATAAAACAGGGGCAAG GCACAGACTCATAGCAGAGCAATCACCACCAG GCCTGGAATAACTGCAGCCACC |
| 35 | #C14_v1 | GGTTAATAATTACCCTTCTAGGATTGAGTCACT TCTAGAAGCTGGACTTTGGACTCATCCTAGAAG TCACTTCCTCTTTTTTACCTAGAAGAGGTTCAA AGGTCATACCTAGCATAGCTTCACTTCTAGAAG GGTAATTATTAACCGGGCATATAAACAGGGG CAAGGCACAGACTCATAGCAGAGCAATCACCA CCAGGCCTGGAATAACTGCAGCCACC |
| 36 | #A2 | CATAGCTTCACTTCTAGAAGAGGTCAGGGTGAC CTGGGCCTACCTAGCTAGGTTAATAATTACCCT TCTAGAAGTGACTCAATCCTAGAAGCCGGAAG TGGCATCCTAGAAGAGGTTCAAAGGTCATACCT AGGTAAAAAAGAGGAAGTGACTTCTAGGATAA GGAAGTACTTCTAGAAGTACTTCCTTATCCTAG CATAGCTTCACTTCTAGAAGAGGTTCAAAGGTC ATACCTAGGTATGACCTTTGAACCTCTTCTANA AGTTAATATTTAACATCCTAGAAGGGTAATTAT TAACCTAGCAAGGCTGACTACACGAGCACATA TCAGCGCGTCGACGATATCAGACCTGGGCATAT AAAACAGGGGCAAGGCACAGACTCATAGCAGA GCAATCACCACCAAGCCTGGAATAACTGCAGC CACCATGG |
| 37 | #A4 | GTAAAAAAGAGGAAGTGACTTCTAGAAGAGGT TCAAAGGTCATACCTAGCTAGGTTAATAATTAC CCTTCTAGAAGTACTTCCTTATCCTAGTAGCAA GGCTGACTACACGAGCACATATCAACGCGTCG ACGATATCAGATCTGGGCATATAAACAGGGG |

TABLE 1-continued

SEQ ID NOs: 1-40

| SEQ ID NO: | Identity | Sequence |
|---|---|---|
| | | CAAGGCACAGACCCATAGCAGAGCAATCACCA CCAAGCCTGGAATAACTGCAGCCACCATGG |
| 38 | #A11 | AAGAGGTCAGGGTGACCTGGGCCTACCTAGGA TAAGGAAGTACTTCTAGAAGTGACTCAATCCTA GAAGGGTAATTATTAACCTAGCTAGGATGAGTC CAAAGTCCAGCTTCTAGGTAGTAGGGCAAAGG TCACTTCTAGGATTGAGTCACTTCTAGGATGAG TCCAAAGTCCAGCTTCTAGAAGAGGTTCAAAG GTCATACCTAGGTAAAAAGAGGAAGTGACTT CTAGAAGTTAATATTTAACATCCTAGGAGTCAC TTCCTCTTTTTTACCTAGTAGCAAGGCTGACTAC ACGAGCACATATCAACGCGTCAACGATATCAG ATCTGGGCATATAAAACAGGGGCAAGGCACAG ACTCATAGCAGAGCAATCACCACCAAGCCTGG AATAACTGCAGCCACCATGG |
| 39 | #C13 | TTTCTCTGGCCTAACTGGCCGGTACCGTCGACT GTGCTCGGACCTGTAGATGCTAGTCTAGAAGAG GTTCAAAGGTCATACCTAGGATAAGGAAGTAC TTCTAGGTAGGCCCAGGTCACCCTGACCTCTTC TAGGATAAGGAAGTACTTCTAGAAGAGGTCAG GGTGACCTGGGCCTACCTAGAAGTACTTCCTTA TCCTAGGTATGACCTTTGAACCTCTTCTAGACT AGCATCTACAGGTCCGAGCACAGTCGACGGTA CCGGCCAGTTAGGCCAGAGAAATGTTCTGNCA CCTG |
| 40 | #C81 | TAGTAGGGCAAAGGTCACTTCTAGAAGCCGGA AGTGGCATCCTAGAAGTGACTCAATCCTAGAA GAGGTCAGGGTGACCTGGGCCTACCTAGAAGT GACTCAATCCTAGGATGTTAAATATTAACTTCT AGTAGCAAGGCTGACTACACGAGCACATATCA ACGCGTCGACGATATCAGATCTGGGCATATAA AACAGGGGCAAGGCACAGACTCATAGCAGAGC AATCACCACCAAGCCTGGAATAACTGCAGCCA CCATGG |

TABLE 2

SEQ ID NOs: 41-90

| SEQ ID NO: | Groups of promoter variants | bp | Description | Sequence |
|---|---|---|---|---|
| 41 | Deletion of 1 promoter part (derivatives of SEQ ID NO: 26) | 177 | 1-2-3-4-10 | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACGGGCATAT AAAACAGGGGCAAGGCACAGACTCAT AGCAGAGCAATCACCACCAAGCCTGGA ATAACTGCAGCCACC |
| 42 | | 227 | 1-2-3-5-10 | AAGCAAATATTTGTGGTTATGGATTAA CTCGAACTGTTTGCCCACTCTATTTGCC CGGCGCCCTTTGGACCTTTTGCAATCCT GGGGACTTAGCCCCTGTTTGCTCCTCCG ATAACTGGGGTGACCTTGGTTAATATT CACCAGCAGCCTCGGGCATATAAAACA GGGGCAAGGCACAGACTCATAGCAGA GCAATCACCACCAAGCCTGGAATAACT GCAGCCACC |
| 43 | | 214 | 1-2-4-5-10 | AAGCAAATATTTGTGGTTATGGATTAA CTCGAACTGTTTGCCCACTCTATTTGCC CAGCAAACAGCAAACACGGACTTAGCC CCTGTTTGCTCCTCCGATAACTGGGGTG ACCTTGGTTAATATTCACCAGCAGCCTC GGGCATATAAAACAGGGGCAAGGCAC AGACTCATAGCAGAGCAATCACCACCA AGCCTGGAATAACTGCAGCCACC |

TABLE 2-continued

SEQ ID NOs: 41-90

| SEQ ID NO: | Groups of promoter variants | bp | Description | Sequence |
|---|---|---|---|---|
| 44 | | 210 | 2-3-4-5-10 | CTGTTTGCCCACTCTATTTGCCCGGCGC CCTTTGGACCTTTTGCAATCCTGGAGCA AACAGCAAACACGGACTTAGCCCCTGT TTGCTCCTCCGATAACTGGGGTGACCTT GGTTAATATTCACCAGCAGCCTCGGGC ATATAAAACAGGGGCAAGGCACAGAC TCATAGCAGAGCAATCACCACCAAGCC TGGAATAACTGCAGCCACC |
| 45 | | 220 | 1-3-4-5-10 | AAGCAAATATTTGTGGTTATGGATTAA CTCGAAGGCGCCCTTTGGACCTTTTGCA ATCCTGGAGCAAACAGCAAACACGGAC TTAGCCCCTGTTTGCTCCTCCGATAACT GGGGTGACCTTGGTTAATATTCACCAG CAGCCTCGGGCATATAAAACAGGGGCA AGGCACAGACTCATAGCAGAGCAATCA CCACCAAGCCTGGAATAACTGCAGCCA CC |
| 46 | Deletion of 1 promoter part (derivatives of SEQ ID NO: 33 and SEQ ID NO: 35) | 171 | 12-14-15-14-12-10 (deletion 11) | AGCTTCACTTCCAGGTATGACCTTTGAA CCTCTTCTAGAAGGGTAATTATTAACCT AGCTAGGTATGACCTTCGAACCTCTTCT AGAAGTGAAGCTGGGCATATAAACAG GGGCAAGGCACAGACTCATAGCAGAG CAATTACCACCAAGCCTGGAATAGCTG CAGCCACC |
| 47 | | 155 | 15-14-12-15-10 (deletion 17-18-19) | GGTTAATAATTACCCTTCTAGGATAGG TTCAAAGGTCATACCTAGCATAGCTTC ACTTCTAGAAGGGTAATTATTAACCGG GCATATAAAACAGGGGCAAGGCACAG ACTCATAGCAGAGCAATCACCACCAGG CCTGGAATAACTGCAGCCACC |
| 48 | | 198 | 17-18-19-14-12-15-10 (deletion 15) | TGAGTCACTTCTAGAAGCTGGACTTTG GACTCATCCTAGAAGTCACTTCCTCTTT TTTACCTAGAAGAGGTTCAAAGGTCAT ACCTAGCATAGCTTCACTTCTAGAAGG GTAATTATTAACCGGGCATATAAAACA GGGGCAAGGCACAGACTCATAGCAGA GCAATCACCACCAGGCCTGGAATAACT GCAGCCACC |
| 49 | | 169 | 11-12-14-14-12-10 (deletion 15) | TTAATATTTAACATCCTAGCACAGCTTC ACTTCCAGGTATGACCTTTGAACCTCTT CTAGAAGTGACCTTCGAACCTCTTCTA GAAGTGAAGCTGGGCATATAAACAGG GGCAAGGCACAGACTCATAGCAGAGC AATTACCACCAAGCCTGGAATAGCTGC AGCCACC |
| 50 | | 181 | 15-17-18-19-15-10 (deletion 14-12) | GGTTAATAATTACCCTTCTAGGATTGA GTCACTTCTAGAAGCTGGACTTTGGAC TCATCCTAGAAGTCACTTCCTCTTTTTT ACCTAGAAGGGTAATTATTAACCGGGC ATATAAAACAGGGGCAAGGCACAGAC TCATAGCAGAGCAATCACCACCAGGCC TGGAATAACTGCAGCCACC |
| 51 | | 162 | 11-12-14-15-10 (deletion 14-12) | TTAATATTTAACATCCTAGCACAGCTTC ACTTCCAGGTATGACCTTTGAACCTCTT CTAGAAGGGTAATTATTAACCTAGCTA GGTAGGGCATATAAACAGGGGCAAGG CACAGACTCATAGCAGAGCAATTACCA CCAAGCCTGGAATAGCTGCAGCCACC |
| 52 | | 121 | 11-15-10 (deletion 12-14 and 14-12) | TTAATATTTAACATCCTAGCACGGTAAT TATTAACCTAGCTAGGTAGGGCATATA AACAGGGGCAAGGCACAGACTCATAG CAGAGCAATTACCACCAAGCCTGGAAT AGCTGCAGCCACC |
| 53 | Shuffling promoter parts (derivatives of SEQ ID NO: 26) | 243 | 1-2-3-4-5R-10 | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACGAGGCTGC TGGTGAATATTAACCAAGGTCACCCCA GTTATCGGAGGAGCAAACAGGGGCTAA GTCCGGGCATATAAAACAGGGGCAAG GCACAGACTCATAGCAGAGCAATCACC ACCAAGCCTGGAATAACTGCAGCCACC |

TABLE 2-continued

SEQ ID NOs: 41-90

| SEQ ID NO: | Groups of promoter variants | bp | Description | Sequence |
|---|---|---|---|---|
| 54 | | 243 | 2-1-3-4-5-10 | CTGTTTGCCCACTCTATTTGCCCAAGCAAATATTTGTGGTTATGGATTAACTCGAAGGCGCCCTTTGGACCTTTTGCAATCCTGGAGCAAACAGCAAACACGGACTTAGCCCCTGTTTGCTCCTCCGATAACTGGGGTGACCTTGGTTAATATTCACCAGCAGCCTCGGGCATATAAAACAGGGGCAAGGCACAGACTCATAGCAGAGCAATCACCACCAAGCCTGGAATAACTGCAGCCACC |
| 55 | | 243 | 4-5-1-2-3-10 | AGCAAACAGCAAACACGGACTTAGCCCCTGTTTGCTCCTCCGATAACTGGGGTGACCTTGGTTAATATTCACCAGCAGCCTCAAGCAAATATTTGTGGTTATGGATTAACTCGAACTGTTTGCCCACTCTATTTGCCCGGCGCCCTTTGGACCTTTTGCAATCCTGGGGCATATAAAACAGGGGCAAGGCACAGACTCATAGCAGAGCAATCACCACCAAGCCTGGAATAACTGCAGCCACC |
| 56 | | 243 | 1R-2-3-4-5-10 | TTCGAGTTAATCCATAACCACAAATATTTGCTTCTGTTTGCCCACTCTATTTGCCCGGCGCCCTTTGGACCTTTTGCAATCCTGGAGCAAACAGCAAACACGGACTTAGCCCCTGTTTGCTCCTCCGATAACTGGGGTGACCTTGGTTAATATTCACCAGCAGCCTCGGGCATATAAAACAGGGGCAAGGCACAGACTCATAGCAGAGCAATCACCACCAAGCCTGGAATAACTGCAGCCACC |
| 57 | | 243 | 2-4-1-3-5-10 | CTGTTTGCCCACTCTATTTGCCCAGCAAACAGCAAACACAAGCAAATATTTGTGGTTATGGATTAACTCGAAGGCGCCCTTTGGACCTTTTGCAATCCTGGGGACTTAGCCCCTGTTTGCTCCTCCGATAACTGGGGTGACCTTGGTTAATATTCACCAGCAGCCTCGGGCATATAAAACAGGGGCAAGGCACAGACTCATAGCAGAGCAATCACCACCAAGCCTGGAATAACTGCAGCCACC |
| 58 | | 243 | 1-2-3-4R-5-10 | AAGCAAATATTTGTGGTTATGGATTAACTCGAACTGTTTGCCCACTCTATTTGCCCGGCGCCCTTTGGACCTTTTGCAATCCTGGGTGTTTGCTGTTTGCTGGACTTAGCCCCTGTTTGCTCCTCCGATAACTGGGGTGACCTTGGTTAATATTCACCAGCAGCCTCGGGCATATAAAACAGGGGCAAGGCACAGACTCATAGCAGAGCAATCACCACCAAGCCTGGAATAACTGCAGCCACC |
| 59 | Shuffling promoter parts (derivatives of SEQ ID NO: 33 and SEQ ID NO: 35) | 222 | 15-14-12-15-17-18-19-10 | GGTTAATAATTACCTACCTAGAAGAGGTTCAAAGGTCATACCTAGCATAGCTTCACTTCTAGAAGGGTAATTATTAACCCTTCTAGGATTGAGTCACTTCTAGAAGCTGGACTTTGGACTCATCCTAGAAGTCACTTCCTCTTTTTGGGCATATAAAACAGGGGCAAGGCACAGACTCATAGCAGAGCAATCACCACCAGGCCTGGAATAACTGCAGCCACC |
| 60 | | 222 | 15-(17-18-19R)-14-12-15-10 | GGTTAATAATTACCCTTCTAGGATAAAAAGAGGAAGTGACTTCTAGGATGAGTCCAAAGTCCAGCTTCTAGAAGTGACTCATACCTAGAAGAGGTTCAAAGGTCATACCTAGCATAGCTTCACTTCTAGAAGGGTAATTATTAACCGGGCATATAAAACAGGGGCAAGGCACAGACTCATAGCAGAGCAATCACCACCAGGCCTGGAATAACTGCAGCCACC |
| 61 | | 193 | (11-12-14-15R)14-12-10 | GGTTAATAATTACCCTTCTAGAAGAGGTTCAAAGGTCATACCTGGAAGTGAAGCTGTGCTAGGATGTTAAATATTAATAGCTAGGTATGACCTTCGAACCTCTTCTAGAAGTGAAGCTGGGCATATAAAACAGGGGCAAGGCACAGACTCATAGCAGAGCAATTACCACCAAGCCTGGAATAGCTGCAGCCACC |
| 62 | | 193 | 10-11-12-14-15-14-12 | GGGCATATAAAACAGGGGCAAGGCACAGACTCATAGCAGAGCAATTACCACCAA |

TABLE 2-continued

SEQ ID NOs: 41-90

| SEQ ID NO: | Groups of promoter variants | bp | Description | Sequence |
|---|---|---|---|---|
| | | | | GCCTGGAATAGCTGCATTAATATTTAA CATCCTAGCACAGCTTCACTTCCAGGT ATGACCTTTGAACCTCTTCTAGAAGGG TAATTATTAACCTAGCTAGGTATGACCT TCGAACCTCTTCTAGAAGTGAAGCTGC CACC |
| 63 | | 193 | 11-12-14-14-12-15-10 | TTAATATTTAACATCCTAGCACAGCTTC ACTTCCAGGTATGACCTTTGAACCTTAG CTAGGTATGACCTTCGAACCTCTTCTAG AAGTGAAGCTCTTCTAGAAGGGTAATT ATTAACCGGGCATATAAACAGGGGCAA GGCACAGACTCATAGCAGAGCAATTAC CACCAAGCCTGGAATAGCTGCAGCCAC C |
| 64 | | 222 | 15-17-(18R)-19-14-(12R)-15-10 | GGTTAATAATTACCCTTCTAGGATTGA GTCACTTCTAGAAGGAGTCCAAAGTCC AGATCCTAGAAGTCACTTCCTCTTTTTT ACCTAGAAGAGGTTCAAAGGTCACTTC TAGAAGTGAAGCTATGCTAGGTAGGTA ATTATTAACCGGGCATATAAAACAGGG GCAAGGCACAGACTCATAGCAGAGCA ATCACCACCAGGCCTGGAATAACTGCA GCCACC |
| 65 | | 222 | 15-17-(18R)-19-14-(12Rshort)-15-10 | GGTTAATAATTACCCTTCTAGGATTGA GTCACTTCTAGAAGGAGTCCAAAGTCC AGATCCTAGAAGTCACTTCCTCTTTTTT ACCTAGAAGAGGTTCAAAGGTCATACC TAGCATTGAAGCTCTTCTAGAAGGGTA ATTATTAACCGGGCATATAAAACAGGG GCAAGGCACAGACTCATAGCAGAGCA ATCACCACCAGGCCTGGAATAACTGCA GCCACC |
| 66 | | 193 | 15-14-11-12-14-12-10 | GGTAATTATTAACCTAGCTAGGTATGA CCTTCGAACCTCTTCTAGAAGTTAATAT TTAACATCCTAGCACAGCTTCACTTCCA GGTATGACCTTTGAACCTCTTCTAGAA GTGAAGCTGGGCATATAAACAGGGGCA AGGCACAGACTCATAGCAGAGCAATTA CCACCAAGCCTGGAATAGCTGCAGCCA CC |
| 67 | Intron addition (derivatives of SEQ ID NO: 26) | 360 | 1-2-3-4-5-10-SD/SA_SV40 | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACGGACTTAG CCCCTGTTTGCTCCTCCGATAACTGGGG TGACCTTGGTTAATATTCACCAGCAGC CTCGGGCATATAAACAGGGGCAAGGC ACAGACTCATAGCAGAGCAATCACCAC CAAGCCTGGAATAACTGCAGCCACAGT GAATCCGGACTCTAAGGTAAATATAAA ATTTTTAAGTGTATAATGTGTTAAACTA CTGATTCTAATTGTTTCTCTCTTTTAGA TTCCAACCTTTGGAACTGAATTCTAGAC CACC |
| 68 | | 419 | 1-2-3-4-5-7-SD/SA_SV40 | TAAAGCAAATATTTGTGGTTATGGATT AACTCGAACTTCTAGAAGCTGTTTGCC CACTCTATTTGCCCATCCTAGGTAGGCG CCCTTTGGACCTTTTGCAATCCTGGCTT CTAGAAGAGCAAACAGCAAACACATCC TAGGTAGGACTTAGCCCCTGTTTGCTCC TCCGATAACTGGGGTGACCTTGGTTAA TATTCACCAGCAGCCTCATGCTAGCCTC GAGGATATCAGATCTTCATCTATTTCCT GCCCACATCTGGTATAAAAGGAGGCAG TGGCCCACAGAGGAGCACAGCTGTGCA GTGAATCCGGACTCTAAGGTAAATATA AAATTTTTAAGTGTATAATGTGTTAAAC TACTGATTCTAATTGTTTCTCTCTTTTA GATTCCAACCTTTGGAACTGAATTCTA GACCACC |
| 69 | | 360 | 1-2-3-4-10-SD-5-SA | AAGCAAATATTTGTGGTTATGGATTAA CTCGAACTGTTTGCCCACTCTATTTGCC CGGCGCCCTTTGGACCTTTTGCAATCCT |

TABLE 2-continued

SEQ ID NOs: 41-90

| SEQ ID NO: | Groups of promoter variants | bp | Description | Sequence |
|---|---|---|---|---|
| | | | | GGAGCAAACAGCAAACACGGGCATAT AAAACAGGGGCAAGGCACAGACTCAT AGCAGAGCAATCACCACCAAGCCTGGA ATAACTGCAGCCACAGTGAATCCGGAC TCTAAGGTAAATATAAAATTTTTAAGG AGGCTGCTGGTGAATATTAACCAAGGT CACCCCAGTTATCGGAGGAGCAAACAG GGGCTAAGTCCTGTATAATGTGTTAAA CTACTGATTCTAATTGTTTCTCTCTTTTA GATTCCAACCTTTGGAACTGAATTCTA GACCACC |
| 70 | Intron addition (derivatives of SEQ ID NO: 33 and SEQ ID NO: 35) | 339 | 15-17-18-19-14-12-15-10-SD/SA_SV40 | GGTTAATAATTACCCTTCTAGGATTGA GTCACTTCTAGAAGCTGGACTTTGGAC TCATCCTAGAAGTCACTTCCTCTTTTTT ACCTAGAAGAGGTTCAAAGGTCATACC TAGCATAGCTTCACTTCTAGAAGGGTA ATTATTAACCGGGCATATAAAACAGGG GCAAGGCACAGACTCATAGCAGAGCA ATCACCACCAGGCCTGGAATAACTGCA GCCACAGTGAATCCGGACTCTAAGGTA AATATAAAATTTTTAAGTGTATAATGT GTTAAACTACTGATTCTAATTGTTTCTC TCTTTTAGATTCCAACCTTTGGAACTGA ATTCTAGACCACC |
| 71 | | 310 | 11-12-14-15-14-12-10-SD/SA_SV40 | TTAATATTTAACATCCTAGCACAGCTTC ACTTCCAGGTATGACCTTTGAACCTCTT CTAGAAGGGTAATTATTAACCTAGCTA GGTATGACCTTCGAACCTCTTCTAGAA GTGAAGCTGGGCATATAAACAGGGGCA AGGCACAGACTCATAGCAGAGCAATTA CCACCAAGCCTGGAATAGCTGCAGCCA CAGTGAATCCGGACTCTAAGGTAAATA TAAAATTTTTAAGTGTATAATGTGTTAA ACTACTGATTCTAATTGTTTCTCTCTTTT AGATTCCAACCTTTGGAACTGAATTCT AGACCACC |
| 72 | | 341 | 11-12-14-15-10-SD-14-12-SA | TTAATATTTAACATCCTAGCACAGCTTC ACTTCCAGGTATGACCTTTGAACCTCTT CTAGAAGGGTAATTATTAACCTAGCTA GGTATGACCTTCGAACCTCTTCTAGAA GTGAAGCTGGGCATATAAACAGGGGCA AGGCACAGACTCATAGCAGAGCAATTA CCACCAAGCCTGGAATAGCTGCAGCCA CAGTGAATCCGGACTCTAAGGTAAATA TAAAATTTTTAAGTGACCTTCGAACCTC TTCTAGAAGTGAAGCTTGTATAATGTG TTAAACTACTGATTCTAATTGTTTCTCT CTTTTAGATTCCAACCTTTGGAACTGAA TTCTAGACCACC |
| 73 | Constructs in which the "space" around the certain elements is mutated in steps; mutating 7, | 243 | 7 mutations in spacer seqs | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACTAACTTAGC CCCTGTTTGCTCCTCCGATCCCCATGGT GACCTTGGTTAATATTCACCAGCAGCC TCGGGCATATAAAACAGGGGCAAGGC ACAGACTCATAGCAGAGCAATCACCAC CAAGCCTGGAATAACTGCAGCCACC |
| 74 | 10, 13, 16, 19, 22 and 25 nucleic acid positions homology to CRM8 by taking into account/ maintaining | 243 | 8 mutations in sp

TABLE 2-continued

SEQ ID NOs: 41-90

| SEQ ID NO: | Groups of promoter variants | bp | Description | Sequence |
|---|---|---|---|---|
| | 71 NA of SEQ ID NO: 3 which appear to be highly conserved. | | | GACCTTGGTTAATATTCACCAGCAATCT CGGGCATATAAAACAGGGGCAAGGCA CAGACTCATAGCAGAGCAATCACCACC AAGCCTGGAATAACTGCAGCCACC |
| 76 | | 243 | 6 mutations; neutral HNF3, spacer, optimization 3' LEF1 site | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACGGACTTAG CCCCTATTTACTCCTCCGATGACTCAGG TGACTTTGGTTAATATTCACCAGCAGCC TCGGGCATATAAAACAGGGGCAAGGC ACAGACTCATAGCAGAGCAATCACCAC CAAGCCTGGAATAACTGCAGCCACC |
| 77 | | 243 | 9 mutations; spacer, MYOD/CEBP site mutation | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACGGACTTAG CCCCTGTTTGCTCCTCCGATAGACGGTG TGACCTTGGTTAATATTCACCATAGAG CTCGGGCATATAAAACAGGGGCAAGGC ACAGACTCATAGCAGAGCAATCACCAC CAAGCCTGGAATAACTGCAGCCACC |
| 78 | | 243 | 14 mutations in spacer seqs, neutral HNF3, optimization 3' LEF1 site and mutation MYOD/CEBP site | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACTAACTTAGC CCCTATTTACTCCTTAGATCCCCATGGT GACTTTGGTTAATATTCACCAGCAATCT CGGGCATATAAAACAGGGGCAAGGCA CAGACTCATAGCAGAGCAATCACCACC AAGCCTGGAATAACTGCAGCCACC |
| 79 | | 243 | 12 mutations; neutral HNF3, spacer, optimization 5' and 3' LEF1 sites, MYOD mutation | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACTCACTTTGC CCCTATTTACTCCTCCGATGACTCAGGT GACTTTGGTTAATATTCACCAGCAGCT AGGGGCATATAAAACAGGGGCAAGGC ACAGACTCATAGCAGAGCAATCACCAC CAAGCCTGGAATAACTGCAGCCACC |
| 80 | Constructs in which certain CRM8 elements are inverted, and/or swapped: HNF1 (REV), FOXA1 | 243 | Cluster 5' reversed | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACGCGGAGGA GCAAACAGGGGCTAAGTCATAACTGGG GTGACCTTGGTTAATATTCACCAGCAG CCTCGGGCATATAAAACAGGGGCAAGG CACAGACTCATAGCAGAGCAATCACCA CCAAGCCTGGAATAACTGCAGCCACC |
| 81 | (REV), HNF1 (REV) AND FOXA1 (REV), and HNF1 swapped with FOXA1, minimal constructs | 243 | Cluster 3' reversed | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACGGACTTAG CCCCTGTTTGCTCCTCCGATAACTGGGG GCTGCTGGTGAATATTAACCAAGGTCA CTCGGGCATATAAAACAGGGGCAAGGC ACAGACTCATAGCAGAGCAATCACCAC CAAGCCTGGAATAACTGCAGCCACC |
| 82 | (non-element sequence removed). | 243 | HNF3 reversed | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACGGACTTAG CGGAGCAAACAGGGTCCGATAACTGGG GTGACCTTGGTTAATATTCACCAGCAG CCTCGGGCATATAAAACAGGGGCAAGG CACAGACTCATAGCAGAGCAATCACCA CCAAGCCTGGAATAACTGCAGCCACC |
| 83 | | 243 | HNF1 reversed | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACGGACTTAG CCCCTGTTTGCTCCTCCGATAACTGGGG TGACCTGCTGGTGAATATTAACCAAGC |

TABLE 2-continued

SEQ ID NOs: 41-90

| SEQ ID NO: | Groups of promoter variants | bp | Description | Sequence |
|---|---|---|---|---|
| 84 | | 243 | Spacer reversed | CTCGGGCATATAAAACAGGGGCAAGGC ACAGACTCATAGCAGAGCAATCACCAC CAAGCCTGGAATAACTGCAGCCACC AAGCAAATATTTGTGGTTATGGATTAA CTCGAACTGTTTGCCCACTCTATTTGCC CGGCGCCCTTTGGACCTTTTGCAATCCT GGAGCAAACAGCAAACACGGACTTAG CCCCTGTTTGCTCCTCCGCCCCAGTTAT TGACCTTGGTTAATATTCACCAGCAGC |
| 85 | | 233 | Deleted spacer | CTCGGGCATATAAAACAGGGGCAAGGC ACAGACTCATAGCAGAGCAATCACCAC CAAGCCTGGAATAACTGCAGCCACC AAGCAAATATTTGTGGTTATGGATTAA CTCGAACTGTTTGCCCACTCTATTTGCC CGGCGCCCTTTGGACCTTTTGCAATCCT GGAGCAAACAGCAAACACGGACTTAG CCCCTGTTTGCTCCTCCGTGACCTTGGT TAATATTCACCAGCAGCCTCGGGCATA TAAAACAGGGGCAAGGCACAGACTCAT AGCAGAGCAATCACCACCAAGCCTGGA ATAACTGCAGCCACC |
| 86 | derivative of SEQ ID NO: 26 | 278 | SEQ ID NO: 26 but with (-137/-37) fragment from antitrypsin promoter replacing full CRM8 sequence | AAGCAAATATTTGTGGTTATGGATTAA CTCGAACTGTTTGCCCACTCTATTTGCC CGGCGCCCTTTGGACCTTTTGCAATCCT GGAGCAAACAGCAAACACGACTCAGA TCCCAGCCAGTGGACTTAGCCCCTGTTT GCTCCTCCGATAACTGGGGTGACCTTG GTTAATATTCACCAGCAGCCTCCCCCGT TGCCCCTCTGGGGCATATAAAACAGGG GCAAGGCACAGACTCATAGCAGAGCA ATCACCACCAAGCCTGGAATAACTGCA GCCACC |

TABLE 3

SEQ ID NOs: 87-100

| SEQ ID NO: | Groups of promoter variants | Description | Sequence |
|---|---|---|---|
| 87 | CRM8 variant sequences (from SEQ ID NOs: 73-86, respectively) | 7 mutations in spacer seqs | TAACTTAGCCCCTGTTTGCTCCTCCGATCCCCA TGGTGACCTTGGTTAATATTCACCAGCAGCCTC |
| 88 | | 8 mutations in spacer seqs | AGACTTAGCCCCTGTTTGCTCCTCCGATGGCTA AGGTGACCTTGGTTAATATTCACCAGCAGCTAG |
| 89 | | 11 mutations in spacer seqs and binding sites (NO HNF site mutations) | TAACTTAGCCCCTGTTTGCTCCTTAGATCCCCA TGGTGACCTTGGTTAATATTCACCAGCAATCTC |
| 90 | | 6 mutations; neutral HNF3, spacer, optimization 3' LEF1 site | GGACTTAGCCCCTATTTACTCCTCCGATGACTC AGGTGACTTTGGTTAATATTCACCAGCAGCCTC |
| 91 | | 9 mutations; spacer, MYOD/CEBP site mutation | GGACTTAGCCCCTGTTTGCTCCTCCGATAGACG GTGTGACCTTGGTTAATATTCACCATAGAGCTC |
| 92 | | 14 mutations in spacer seqs, neutral HNF3, optimization 3' LEF1 site and mutation MYOD/CEBP site | TAACTTAGCCCCTATTTACTCCTTAGATCCCCA TGGTGACTTTGGTTAATATTCACCAGCAATCTC |
| 93 | | 12 mutations; neutral HNF3, | TCACTTTGCCCCTATTTACTCCTCCGATGACTC AGGTGACTTTGGTTAATATTCACCAGCAGCTA |

TABLE 3-continued

| | | |
|---|---|---|
| | spacer, optimization 5' and 3' LEF1 sites, MYOD mutation | G |
| 94 | Cluster 5' reversed | GCGGAGGAGCAAACAGGGGCTAAGTCATAAC TGGGGTGACCTTGGTTAATATTCACCAGCAGC CTC |
| 95 | Cluster 3' reversed | GGACTTAGCCCCTGTTTGCTCCTCCGATAACTG GGGGCTGCTGGTGAATATTAACCAAGGTCACT C |
| 96 | HNF3 reversed | GGACTTAGCGGAGCAAACAGGGTCCGATAACT GGGGTGACCTTGGTTAATATTCACCAGCAGCC TC |
| 97 | HNF1 reversed | GGACTTAGCCCCTGTTTGCTCCTCCGATAACTG GGGTGACCTGCTGGTGAATATTAACCAAGCCT C |
| 98 | Spacer reversed | GGACTTAGCCCCTGTTTGCTCCTCCGCCCCAGT TATTGACCTTGGTTAATATTCACCAGCAGCCTC |
| 99 | Deleted spacer | GGACTTAGCCCCTGTTTGCTCCTCCG---------- TGACCTTGGTTAATATTCACCAGCAG CCTC |
| 100 | (-137/-37) fragment from antitrypsin promoter | GACTCAGATCCCAGCCAGTGGACTTAGCCCCT GTTTGCTCCTCCGATAACTGGGGTGACCTTGGT TAATATTCACCAGCAGCCTCCCCCGTTGCCCCT CTG |

| SEQ ID NO: | Other promoters | Sequence |
|---|---|---|
| 108 | CMVIE | ATAGTAATCAATTACGGGGTCATTAGTTCATAGCCCATATATG GAGTTCCGCGTTACATAACTTACGGTAAATGGCCCGCCTGGCT GACCGCCCAACGACCCCCGCCCATTGACGTCAATAATGACGT ATGTTCCCATAGTAACGCCAATAGGGACTTTCCATTGACGTCA ATGGGTGGAGTATTTACGGTAAACTGCCCACTTGGCAGTACAT CAAGTGTATCATATGCCAAGTACGCCCCCTATTGACGTCAATG ACGGTAAATGGCCCGCCTGGCATTATGCCCAGTACATGACCTT ATGGGACTTTCCTACTTGGCAGTACATCTACGTATTAGTCATC GCTATTACCATGGTGATGCGGTTTTGGCAGTACATCAATGGGC GTGGATAGCGGTTTGACTCACGGGGATTTCCAAGTCTCCACCC CATTGACGTCAATGGGAGTTTGTTTTGGCACCAAAATCAACGG GACTTTCCAAAATGTCGTAACAACTCCGCCCCATTGACGCAAA TGGGCGGTAGGCGTGTACGGTGGGAGGTCTATATAAGCAGAG CTGGTTTAGTGAACCGTCAGATC |

40

Expression Cassettes

In accordance with some embodiments, there are provided expression cassettes comprising a synthetic polynucleotide according to any one of the embodiments described herein and an operably linked polynucleotide sequence encoding a transgene, wherein the transgene encodes a therapeutic polypeptide suitable for use in treating a disease or condition associated with the liver.

In some embodiments, the expression cassettes further comprise a nucleic acid encoding a posttranscriptional regulatory element. In some embodiments, the expression cassettes further comprise a nucleic acid encoding a polyA element.

Gene Therapy Vectors

In accordance with some embodiments, there are provided vectors comprising any one of the synthetic polynucleotides described herein or an expression cassette as described herein.

In some embodiments, the vector is naked DNA, a retroviral vector, a lentiviral vector, an adenoviral vector, or an adeno-associated viral vector (AAV). In some embodiments, the vector is an AAV vector. In some embodiments, the AAV has a serotype suitable for liver transduction. In some embodiments, the AAV is selected from the group consisting of: AAV2, AAV5, AAV6, AAV7, AAV8, AAV9, AAV6.2, AAVrh.64R1, AAVhu.37, AAVrh.8, AAVrh.32.33, AAV3B, and LK03.

In some embodiments, the disclosed liver-specific promoters are incorporated into an AAV gene therapy vector. AAV gene therapy vector may encode multiple components (e.g., capsid proteins, ITRs, etc.), which may be the same or different serotypes, and the vectors may encode one or more therapeutic genes or genes of interest.

AAV gene therapy vectors may comprise an AAV capsid and a polynucleotide. The polynucleotide may encode a therapeutic protein; however, not all polynucleotides encode therapeutic proteins. In some embodiments, a polynucleotide within an AAV gene therapy vector may encode a gene of interest (e.g., a gene that is mutated in a subject), a protein of interest (e.g., a protein that is under-expressed or mutated in a subject), or a therapeutic RNA (e.g., a siRNA, miRNA, or shRNA that targets a gene that is mutated or overexpressed). Hence, the transgene or therapeutic gene may comprise a polynucleotide sequence that encodes a therapeutic protein or a therapeutic RNA or fragments thereof.

The serotype of the AAV gene therapy vector is not particularly limited and may include, but is not limited to, AAV serotype 1 (AAV1), AAV2, AAV3, AAV4, AAV5, AAV6, AAV7, AAV8, AAV9, AAV10, or AAV11. In some embodiments, the AAV is chimeric, meaning it comprises components from at least two AAV serotypes, such as the ITRs of an AAV2 and the capsid protein of an AAV5. In some embodiments, gene therapy may comprise administration of a plurality of AAV gene therapy vectors, and the vectors may be the same or different serotypes.

In some embodiments, the AAV was discovered in human cells or in non-human primate cells, such as rhesus cells or cynomolgus cells.

In some embodiments, the AAV capsid is not a wild-type capsid but is a recombinant AAV (rAAV), such as a rAAV2/5, which comprises at least a portion of AAV2 and AAV5. For example, the VP1 capsid protein may consist of a hybrid amino acid sequence between AAV2 and AAV5, whereas the VP2 and VP3 capsids may be derived from the AAV5 serotype (e.g., Urabe et al. *Scalable generation of high-titer recombinant adeno-associated virus type 5 in insect cells*. J Virol. 2006 February; 80 (4): 1874-85). In some embodiments, the AAV is a chimeric AAV (AAV$^{ch}$), such as a chimeric AAV serotype 5 (AAV5$^{ch}$).

When a plurality of AAV gene therapy vectors are administered to a subject, at least two of the plurality of AAV gene therapy vectors may be the same type of AAVs, while in some embodiments, at least two of the plurality of AAV gene therapy vectors may be different types of AAVs.

Therapeutic Genes

In some embodiments, the AAV gene therapy vectors comprise a transgene or therapeutic gene. The transgene or therapeutic gene comprises a polynucleotide sequence that encodes a therapeutic protein, a therapeutic RNA, or fragments thereof.

The therapeutic protein may be a primate protein, a non-primate protein, or a human protein. In some embodiments, the therapeutic protein may include, but is not limited to, factor IX (FIX), factor VIII (FVIII) and modified forms thereof, including variants, derivatives or equivalents. In some embodiments, the therapeutic gene may include, but is not limited to, alpha-1 antitrypsin (AAT), aromatic amino acid decarboxylase (AADC), ATPase Sarcoplasmic/Endoplasmic Reticulum Ca2+ Transporting 2 (ATP2A2), cystic fibrosis transmembrane conductance regulator (CTFR), glutamic acid decarboxylase 65 kDa protein (GAD65), glutamic acid decarboxylase 67 kDa protein (GAD67), lipoprotein lipase (LPL), nerve growth factor (NGF), neurturin (NTN), porphobilinogen deaminase (PBGD), sarcoglycan alpha (SGCA), soluble fms-like tyrosine kinase-1 (sFLT-1), S100 calcium binding protein A1 (S100A1), survival of motor neuron 1 (SMN1), tripeptidyl peptidase 1 (TPP1), tumor necrosis factor receptor (TNFR)-immunoglobulin (IgG1) Fc fusion (TNFR:Fc), interferon beta (IFN-β), neuropeptide Y receptor Y2, alpha glucosidase, C9orf72, superoxide dismutase (SOD), CFTR, alpha-galactosidase, alpha-N-acetylgalactosaminidase, uricase, chondroitinase, HexA, HexB and modified forms thereof.

The transgenes and/or therapeutic genes may also relate to gene editing. Gene editing is a type of genetic engineering in which DNA is inserted, deleted or replaced in the genome of a living organism using engineered nucleases, or "molecular scissors". Currently four classes of gene editing may be utilized, which involves meganucleases, zinc finger nucleases (ZFNs), transcription activator-like effector-based nucleases (TALEN), and the clustered regularly interspaced short palindromic repeats CRISPR-Cas system. The AAV vectors utilized may be engineered such that the gene editing capabilities are transient to allow the endogenous gene to be edited. The nucleases create site-specific double-strand breaks (DSBs) at desired locations in the genome. The induced double-strand breaks are subsequently repaired through nonhomologous end-joining (NHEJ) or homologous recombination (HR), resulting in targeted mutations. For example, one or more AAV gene therapy vectors may encode a gene targeting a specific gene sequence. A targeted gene may be a diseased gene with the aim of the therapy being to disrupt expression of the diseased gene. Another approach may be with the aim to repair a diseased gene, e.g. with X-linked associated diseases or dominant disease associated genes. One or more AAV gene therapy vectors may encode for a gene editing sequence and a DNA sequence which is to be inserted/replace and/or to repair the gene associated with a disease via e.g. homologous recombination.

In some embodiments of the foregoing aspects, the AAV gene therapy vectors may comprise a polynucleotide that encode interfering RNA (siRNA); a microRNA (miRNA); or a short hairpin RNA (shRNA). In some embodiments, the siRNA, miRNA, or shRNA targets and silences or down-regulates a gene associated with a disease. For example, target genes for silencing may include the Htt gene, the C9orf72 gene or the like, i.e. genes associated with repeat disorders (e.g. trinucleotide (i.e. polyglutamine or non-polyglutamine diseases) or hexanucleotide repeat disorders). In some embodiments, the therapeutic RNA interferes with the expression a gene that encodes a protein involved in a disease.

Therapeutic Agents

In some embodiments, the disclosed methods may comprise one or more therapeutic agents that can be administers before, concurrently, or after administration of the AAV gene therapy vector.

Those of skill in the art will understand that additional therapeutic agents that are suitable for the disclosed methods and kits can include conventional therapies for the diseases and conditions disclosed herein.

Methods of Administration

In accordance with some embodiments, there are provided methods of treating a genetic disease or condition in a subject in need thereof, the methods comprising administering an expression cassette comprising any one of the synthetic polynucleotides described herein, a vector comprising an expression cassette, and/or a recombinant viral particle, thereby expressing a therapeutic peptide in the subject's liver.

In some embodiments, the subject is a mammal. In some embodiments, the mammal is a human.

In accordance with some embodiments, there are provided methods of expressing a transgene in a liver cell, the method comprising contacting the liver cell with an expression cassette comprising any one of the synthetic polynucleotides described herein or a vector comprising an expression cassette.

In accordance with some embodiments, there are provided synthetic nucleic acid sequences according to any one the embodiments described herein, an expression cassette comprising a synthetic nucleic acid sequences according to any one the embodiments described herein, or a vector comprising an expression cassette, for use in a medical treatment of a genetic disease or condition.

The disclosed methods comprise administering an AAV gene therapy vector comprising at least one of the disclosed liver-specific promoters. In some embodiments, the AAV gene therapy vector may be administered concurrently or sequentially with one or more additional therapeutic agents or with one or more saturating agents designed to prevent clearance of the vectors by the reticular endothelial system.

For example, a saturating agent may be administered prior to the AAV gene therapy vector. In some embodiments, the saturating agent is administered at least 5, 10, 15, 20, 25, 30, 35, 40, 45, 50, 55, 60, 65, 70, 75, 80, 85, 90, 95, 100, 110, 120, 130, 140, or 150 or more minutes or 1, 2, 3, 4, 5, 6, 7, 8, 9, 10, 11, 12, 13, 14, 15, 16, 17, 18, 19, 20, 21, 22, 23, or 24 or more hours prior to administration of the AAV gene therapy vector.

Similarly, in some embodiments, the AAV gene therapy vector may be administered at least 5, 10, 15, 20, 25, 30, 35, 40, 45, 50, 55, 60, 65, 70, 75, 80, 85, 90, 95, 100, 110, 120, 130, 140, or 150 or more minutes 1, 2, 3, 4, 5, 6, 7, 8, 9, 10, 11, 12, 13, 14, 15, 16, 17, 18, 19, 20, 21, 22, 23, or 24 or more hours prior to administration of the one or more therapeutic agents. Alternatively, in some embodiments, the AAV gene therapy vector may be administered at least 5, 10, 15, 20, 25, 30, 35, 40, 45, 50, 55, 60, 65, 70, 75, 80, 85, 90, 95, 100, 110, 120, 130, 140, or 150 or more minutes 1, 2, 3, 4, 5, 6, 7, 8, 9, 10, 11, 12, 13, 14, 15, 16, 17, 18, 19, 20, 21, 22, 23, or 24 or more hours after to administration of the one or more therapeutic agents.

The duration of the administration of the components of the disclosed methods may also vary. For instance, an AAV gene therapy vector comprising at least one of the disclosed liver-specific promoters may be administered via a continuous infusion. Accordingly, in some embodiments, administration of the AAV gene therapy vector may extend for at least 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130, 140, or 150 or more minutes. Similarly, when the disclosed methods further comprise administering an additional saturating agent or one or more therapeutic agents, administration of these components may extend for at least 1, 2, 3, 4, 5, 10, 15, 20, 25, 30, 35, 40, 45, 50, 55, 60, 65, 70, 75, 80, 85, 90, 95, 100, 110, 120, 130, 140, or 150 or more minutes.

In some embodiments, the methods disclosed herein comprise administering the AAV gene therapy vector is administered systemically. Systemic administration may be enteral or parenteral. Suitable routes of enteral administration may include, but are not limited to, oral, sublingual, and rectal administration. Suitable routes of enteral administration may include, but are not limited to, inhalation, injection, and transdermal administration. For the purposes of the present disclosure, preferred routes of injection include intravenous, intramuscular, subcutaneous, intra-arterial, intra-articular, intrathecal, and intradermal injections.

In some embodiments, performance of the methods described herein results in increase of expression of a therapeutic gene or gene of interest in the liver by at least 10%, at least 20%, at least 30%, at least 40%, at least 50%, at least 55%, at least 60%, at least 65%, at least 70%, at least 75%, at least 80%, at least 85%, at least 90%, or at least 95% or more compared to known non-specific promoters. In some embodiments, the synthetic polynucleotides increase expression at least 1.2 fold-1.8 fold, 1.5 fold-2.5 fold, 2 fold-5 fold, 4 fold-10 fold, 5 fold-20 fold, or 10 fold-100 fold compared to the known promoter.

In some embodiments, performance of the methods described herein results in increase of a therapeutic gene or gene of interest in the liver by at least 10%, at least 20%, at least 30%, at least 40%, at least 50%, at least 55%, at least 60%, at least 65%, at least 70%, at least 75%, at least 80%, at least 85%, at least 90%, or at least 95% or more compared to a known liver-specific promoter (e.g., the LP-1 promoter). In some embodiments, the synthetic polynucleotides increase expression at least 1.2 fold-1.8 fold, 1.5 fold-2.5 fold, 2 fold-5 fold, 4 fold-10 fold, 5 fold-20 fold, or 10 fold-100 fold compared to a known liver-specific promoter, such as e.g. an LP-1 promoter.

Doses and Dosage Forms

In some embodiments, the disclosed methods comprise a specific dosage of an AAV gene therapy vector comprising at least one of the disclosed liver-specific promoters. The dosage of the AAV gene therapy vector may be, for example, $1\times10^{10}$ gc/kg, $5\times10^{10}$ gc/kg, $1\times10^{11}$ gc/kg, $5\times10^{11}$ gc/kg, $1\times10^{12}$ gc/kg, $2\times10^{12}$ gc/kg, $3\times10^{12}$ gc/kg, $4\times10^{12}$ gc/kg, $5\times10^{12}$ gc/kg, $6\times10^{12}$ gc/kg, $7\times10^{12}$ gc/kg, $8\times10^{12}$ gc/kg, $9\times10^{12}$ gc/kg, $1\times10^{13}$ gc/kg, $5\times10^{13}$ gc/kg, $1\times10^{14}$ gc/kg, $5\times10^{14}$ gc/kg, or $1\times10^{15}$ gc/kg or more. In some embodiments, the dosage of the AAV gene therapy vector is less than $1\times10^{13}$ gc/kg, $5\times10^{13}$ gc/kg, $1\times10^{14}$ gc/kg, $5\times10^{14}$ gc/kg, or $1\times10^{15}$ gc/kg. In some embodiments, the dosage of the AAV gene therapy vector is between $1\times10^{12}$ gc/kg and $1\times10^{14}$ gc/kg. In some embodiments, the dosage of the AAV gene therapy vector is between $5\times10^{12}$ gc/kg and $5\times10^{13}$ gc/kg. In some embodiments, the dosage of the AAV gene therapy vector is $4\times10^{12}$ gc/kg, $4.5\times10^{12}$ gc/kg, $5\times10^{12}$ gc/kg, $5.5\times10^{12}$ gc/kg, $6\times10^{12}$ gc/kg, $6.5\times10^{12}$ gc/kg, $7\times10^{12}$ gc/kg, $7.5\times10^{12}$ gc/kg, $8\times10^{12}$ gc/kg, $8.5\times10^{12}$ gc/kg, $8.6\times10^{12}$ gc/kg, $8.7\times10^{12}$ gc/kg, $8.8\times10^{12}$ gc/kg, $8.9\times10^{12}$ gc/kg, $9\times10^{12}$ gc/kg, $9.1\times10^{12}$ gc/kg, $9.2\times10^{12}$ gc/kg, $9.3\times10^{12}$ gc/kg, $9.4\times10^{12}$ gc/kg, $9.5\times10^{12}$ gc/kg, $9.6\times10^{12}$ gc/kg, $9.7\times10^{12}$ gc/kg, $9.8\times10^{12}$ gc/kg, $9.9\times10^{12}$ gc/kg, $1\times10^{13}$ gc/kg, $1.5\times10^{13}$ gc/kg, $2\times10^{13}$ gc/kg, $2.5\times10^{13}$ gc/kg, $3\times10^{13}$ gc/kg, $3.5\times10^{13}$ gc/kg, $4\times10^{13}$ gc/kg, $4.5\times10^{13}$ gc/kg, $5\times10^{13}$ gc/kg, $5.5\times10^{13}$ gc/kg, or $6\times10^{13}$ gc/kg or more. In some embodiments, the dosage of the AAV gene therapy vector is about $9.7\times10^{12}$ gc/kg or about $5\times10^{13}$ gc/kg. When more than one AAV gene therapy vector is administered to a subject, the respective dosages may be the same or different.

In some embodiments, the dose of an AAV gene therapy vector is less when co-administered with a saturating agent compared to the dose of the same AAV gene therapy vector when administered without the saturating agent. In some embodiments, co-administration with the saturating agent results in at least about a 5%, 10%, 15%, 20%, 25%, 30%, 35%, 40%, 45%, 50%, 55%, 60%, 65%, 70%, or 75% reduction in the dose of the AAV gene therapy vector as compared to the dose of the AAV gene therapy vector without co-administration of the saturating agent.

Indications

The disclosed methods of treatment can be used for treating various genetic disorders and diseases. Genetic diseases and disorders that may be treated with the disclosed methods include, but are not limited to genetic cholestasis, Wilson's disease, hereditary hemochromatosis, tyrosinemia type 1, alpha-1 antitrypsin deficiency, argininosuccinic aciduria, liver cancer, glycogen storage disease, urea cycle disorder, Crigler-Najjar syndrome, familial amyloid polyneuropathy, atypical hemolytic uremic syndrome-1, primary hyperoxaluria type 1, maple syrup urine disease, acute intermittent porphyria, coagulation defects, GSD type1A, homozygous familial hypercholesterolemia, organic acidurias, cystic fibrosis, erythropoietic protoporphyria, Gaucher disease, hemophilia A, hemophilia B, familial hypercholesterolemia, ornithine transcarbamylase deficiency (OTC), phenylketonuria (PKU), acute intermittent porphyria (AIP), age-related macular degeneration, amyotrophic lateral sclerosis (ALS), cystic fibrosis, paralysis, Alzheimer's disease, Parkinson's disease, Huntington's disease (HD), arthritis, Batten disease, Canavan disease, Citrullinemia type 1, rheumatoid arthritis, epilepsy, congestive heart failure, cystic fibrosis, Duchene muscular dystrophy, dyslipidemia, glycogen storage disease type I (GSD-I), hereditary emphysema, homozygous familial hypercholesterolemia (HoFH), Leber's congenital amaurosis, methylmalonic academia, spinal muscular atrophy, paralysis, epilepsy, Pompe disease, Tay-Sachs disease, hyperoxaluria (PH-1), spinocerebellar ataxia type 1 (SCA-1), SCA-3, u-dystrophin, Gaucher's types II or III, arrhythmogenic right ventricular cardiomyopathy (ARVC), Fabry disease, familial Mediterranean fever (FMF), proprionic acidemia, fragile X syndrome, Rett syndrome, Niemann-Pick, and Krabbe disease.

In some embodiments, the AAV gene therapy vectors may be for the treatment of lysosomal storage disorders, metabolic disorders and clotting disorders.

Lysosomal storage disorders may result from a lack of specific enzymes that break down certain lipids (fats) or carbohydrates (sugars) in the body cells. Because the body cannot break down the fat or carbohydrate targeted by enzymes for recycling, these may accumulate in cell lysosomes disrupting normal function resulting in lysosomal storage disorders. Lysosomal disorders may include may include Farber disease, Krabbe disease (Infantile or late onset), Galactosialidosis, Fabry disease (alpha-galactosidase A), Schindler disease (alpha-galactosidase B), Beta-galactosidase/GM1 gangliosidosis, GM2 gangliosidosis, Gaucher disease Type I, II and III, Sphingomyelinase, Lysosomal acid lipase deficiency, Niemann-Pick disease Type A and B, Sulfatidosis, Saposin B deficiency, Multiple sulfatase deficiency, Mucopolysaccharidoses Types I (Hurler/Scheie), II (Hunter), III (Sanfilippo), IV (Morquio), VI (Maroteaux), VII (Sly) and IX (Hyaluronidase deficiency), Mucolipidosis Types I, II, III and IV, Niemann-Pick disease, Neuronal ceroid lipofuscinoses Type 1, 2, 3, 4, 5, 6, 7, 8, 9, and 10, Wolman disease, Alpha-mannosidosis, Beta-mannosidosis, Aspartylglucosaminuria, Fucosidosis, Lysosomal transport diseases, Cystinosis, Pycnodysostosis, Salla disease, Infantile free sialic acid storage disease, Glycogen storage diseases such as Pompe disease and Danon disease, Cholesteryl ester storage disease.

Metabolic disorders may include ornithine transcarbamylase deficiency, phenylketonuria, propionic acidemia, methylmalonic acidemia, primary hyperoxaluria.

Clotting disorders may include deficiencies in coagulation Factors, VII, VIII, IX and X, XI, V, XII, II, von Willebrand factor, combined FV/FVIII deficiency, thalassemia.

For example, in some embodiments, hemophilia A or B can be treated using the disclosed methods by administering to a subject an AAV gene therapy vector that encodes FIX, or a variant thereof. In some embodiments, the AAV gene therapy vector may be an AAV5 serotype and the therapeutic gene (i.e., a gene encoding FIX) may be under the control of one of the disclosed liver-specific promoters. Moreover, in some embodiments, the therapeutic FIX protein may comprise one or more insertions, deletions, or substitutions.

EXAMPLES

The following examples are given to illustrate the present disclosure. It should be understood, however, that the invention is not to be limited to the specific conditions or details described in the examples.

Example 1—Identification of Constituent Promoter Elements

A meta-analysis of liver cell datasets to identify candidate genes for cis-element selection was performed. Microarray and NGS datasets and scientific literature were reviewed to identify genes expressed to very high levels in the target cell type.

Example 2—Selection of Cis-Regulatory Elements for Inclusion in Liver Cell Synthetic Promoter Library Having identified a suitable liver-associated gene set, the promoter regions of selected genes were next analyzed to identify cis-regulatory elements (CREs) and other features responsible for transcriptional regulation in selected promoters. Three methods were used to identify the cis-elements to be incorporated into the construction of synthetic promoter libraries resulting in the selection of at least SEQ ID NOs:1-19.

The cis-elements identified were each used to create distinct libraries. Relevant composite elements for the regulation of liver specific genes were identified through the Liver Specific Gene Promoter Database (LSGPD) and literature searches. These composite elements were then used to design novel synthetic promoters.

Example 3—Creation of Liver-Specific Synthetic Promoter Library Screening Vector Screening vectors were based on the pUC19 backbone (synthetic promoter library+core promoter elements+GFP). The synthetic promoter library is cloned upstream of a minimal promoter sequence. This sequence comprises the necessary elements to recruit the RNA polymerase II complex and includes the transcriptional start site. Minimal promoter sequences show basal transcriptional activity and library sequences cloned upstream are designed to enhance its activity and specificity.

Example 4—Determining Transfection Efficiency in Target Cell Types

Prior to examining the activity of the different screening vectors, the conditions required for optimal transfection of the two chosen liver cell lines (HepG2 and Huh7) were established. The efficiency of gene expression of firefly luciferase from the CMV immediate early (CMVIE) promoter (SEQ ID NO:108) was measured in HepG2 and Huh7 cells. All cell lines were grown and maintained according to the cell banks' recommendations.

Transfections of cells with pCMVIE_Luc were performed with different transfection reagents, including FugeneHID Transfection Reagent (Promega #E2311) at a DNA:FuGene HD ratio of 1:1.1. Luciferase activity was measured 24 hours after transfection. Cells were washed with phosphate buffered saline (PBS), lysed in 100 µl Passive Lysis Buffer (Promega #E194A) and stored at −80° C. overnight. Luciferase activity was quantified using the Luciferase Reporter 1000 assay system (Promega #E4550) following manufacturer's guidelines in 10 µl of lysate using 96 well flat bottom solid white Microplate FluoroNunc plates (ThermoFisher #236105) and luminescence quantified in a FLUOstar Omega plate reader (BMG Labtech) machine. It was demonstrated that FugeneHD mediated the optimal transfection efficiency in the chosen liver cell lines, and was consequently chosen as the transfection reagent of choice for all future experiments.

Next, all promoter libraries were screened in different liver cell types in order to identify liver specific promoters with maximum activity in all cell types in vitro. Screening was performed by Fluorescent Activated Cell Sorting (FACS) in a selection of liver cell types. Promoters were operably linked to green fluorescent protein (GFP) and expression of GFP in Huh7 and HepG2 cells was assessed using FACS analysis. FIG. 1 is an example related to constructs expressing GFP under an CMV promoter (FIG. 1). This data shows that both Huh7 and HepG2 cells were efficiently transfected with constructs expressing GFP and assess activity using FACS. The efficiency of expression was measured after 24 hours' transfection and it was found that over 15% of cells expressed GFP.

Example 5—Testing of Minimal Promoter Activity and Selection of Screening Vectors for Use in Library Screen Based on a detailed analysis of a variety of natural promoters driving expression of known liver-specific genes, the minimal promoter sequences were selected for insertion into synthetic promoter screening vectors (FIG. 2). Putative TATA-box (shown in bold), initiator sequences (underlined) and TSS (shown in bold with double underling) elements are shown. Screening vectors were to be designed so that combinations of the cis-regulatory elements could be cloned in random combinations upstream of the selected minimal promoter sequence.

Figure 3:
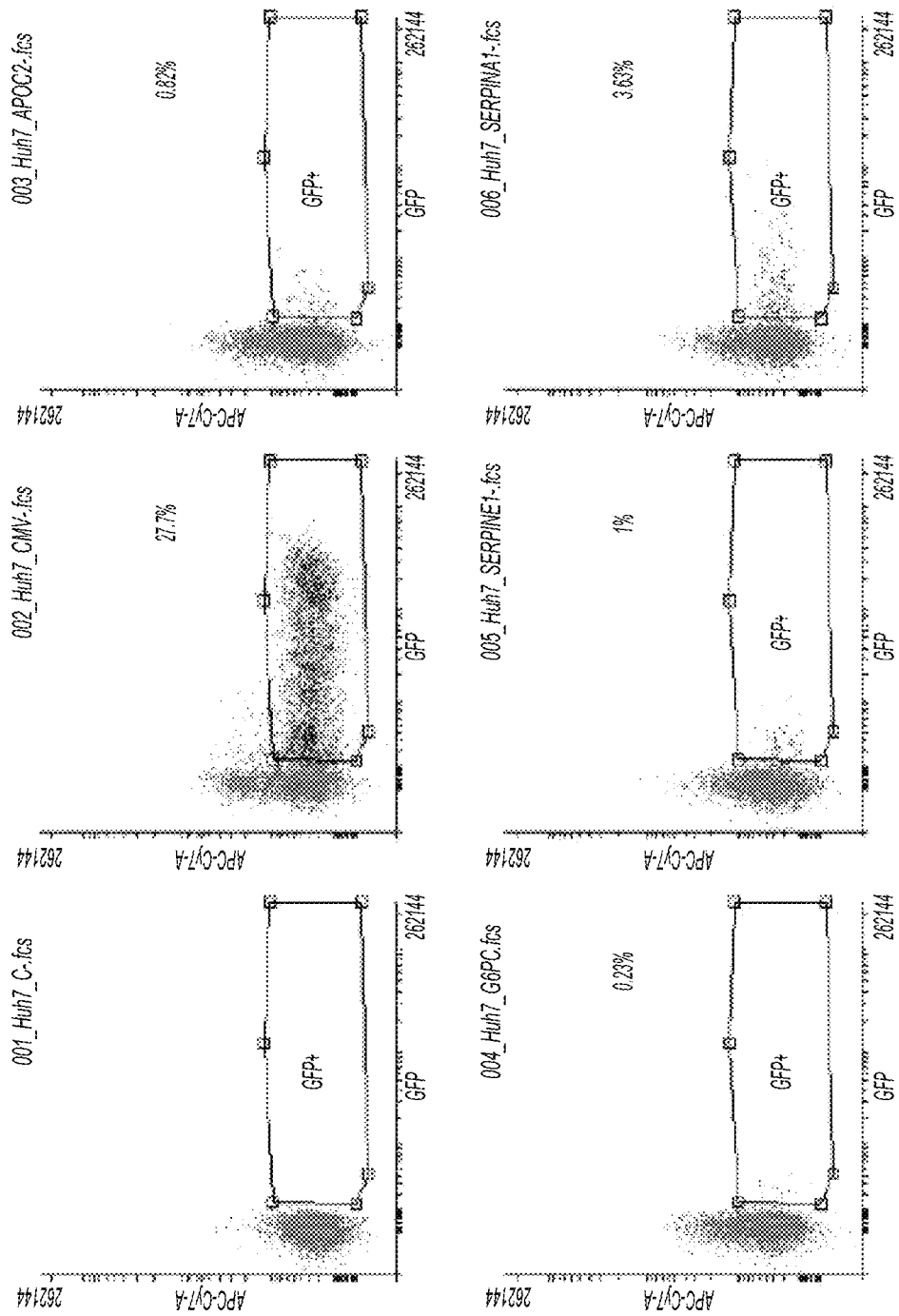
FIG. 3 shows an assessment of activity of minimal promoters in Huh7 cells.

Next, the transcriptional activity of each individual minimal promoter sequence with a view to select the optimal minimal promoter for use in the library screen was assessed (FIG. 3). Each minimal promoter showed basal levels of transcriptional activity in Huh7 cells and as such were suitable candidates for inclusion in the synthetic promoter library screening vector.

Figure 4:
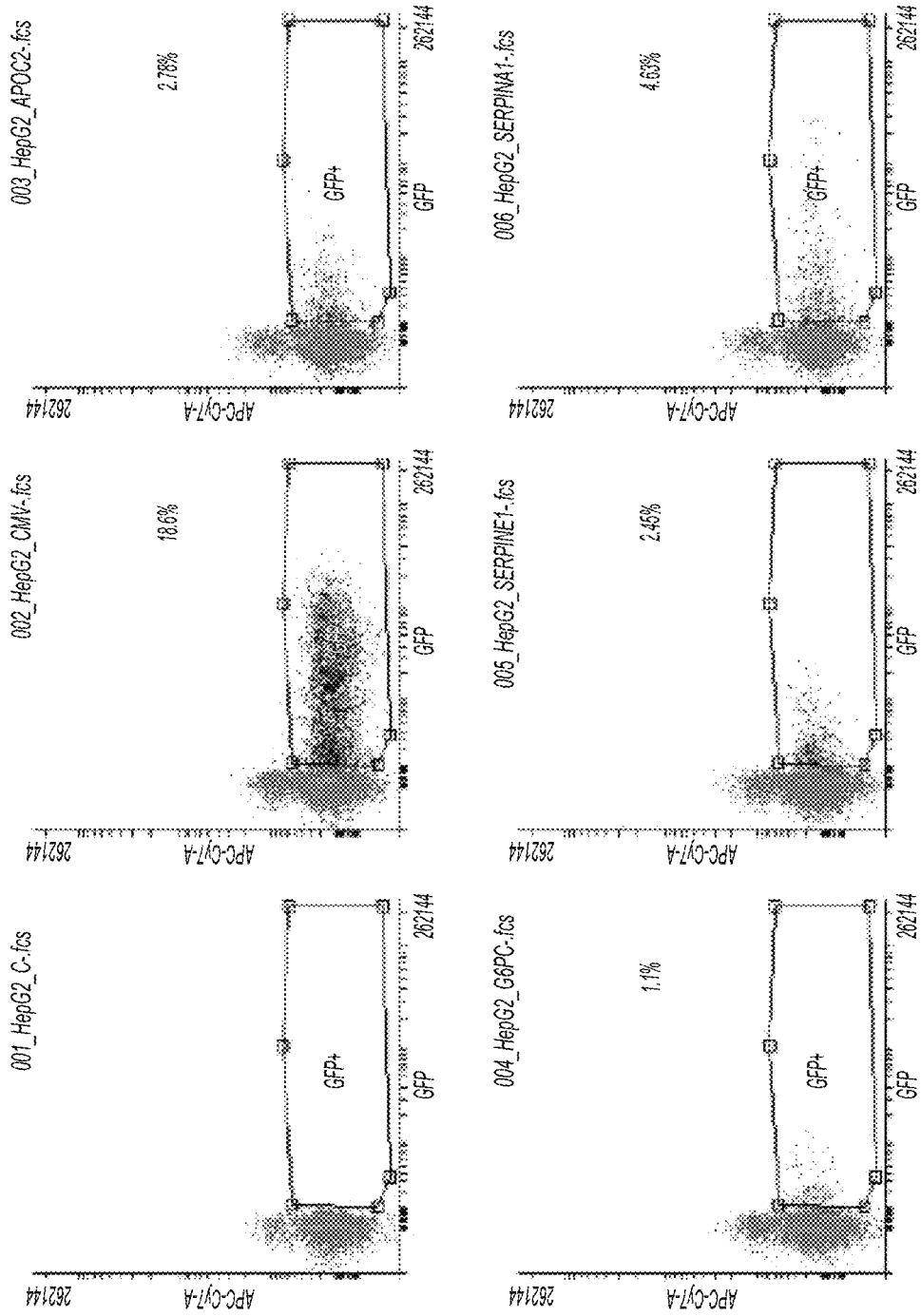
FIG. 4 shows an assessment of activity of minimal promoters in HepG2 cells.

Transcriptional activity was monitored in HepG2 cells (FIG. 4). Transcriptional activity was somewhat higher in HepG2 cells compared to Huh7 cells. G6PC and SERPINE1 were identified as having the lowest basal activity and consequently the optimal candidates for minimal promoters to be included in the screening vector.

Example 6—Construction of Screening Libraries and Screening Vectors for Transfection into Liver Cells Three distinct sets of liver-specific transcription factor binding sites (or cis-elements) were used to create 3 distinct synthetic libraries.

Each of the three synthetic promoter libraries was then cloned into the screening vector immediately upstream of the G6PC minimal promoter. Downstream of the minimal promoter, GFP is present in the screening vectors. The complexity of each resultant synthetic promoter library is shown in Table 4.

TABLE 4

| Library ID | Estimated complexity |
| --- | --- |
| SYN_L1_UNQ | 100,000 |
| SYN_L2_UNQ | 55,000 |
| SYN_L3_UNQ | 115,000 |

To create promoters of a size less than 250 bp, derivative libraries were made from each meta-analysis and each library was size fractionated so that each potential promoter candidate was less than 300 bp in size. The complexity of those size fractionated libraries is shown in Table 5.

TABLE 5

| Library ID | Estimated complexity |
| --- | --- |
| SYN_L1_UNQS | 82,000 |
| SYN_L2_UNQS | 46,000 |
| SYN_L3_UNQs | 40,000 |

Exemplary library SYN_L1_UNQ, based on meta-analysis, was selected for additional screening in different liver cells.

Figure 5:
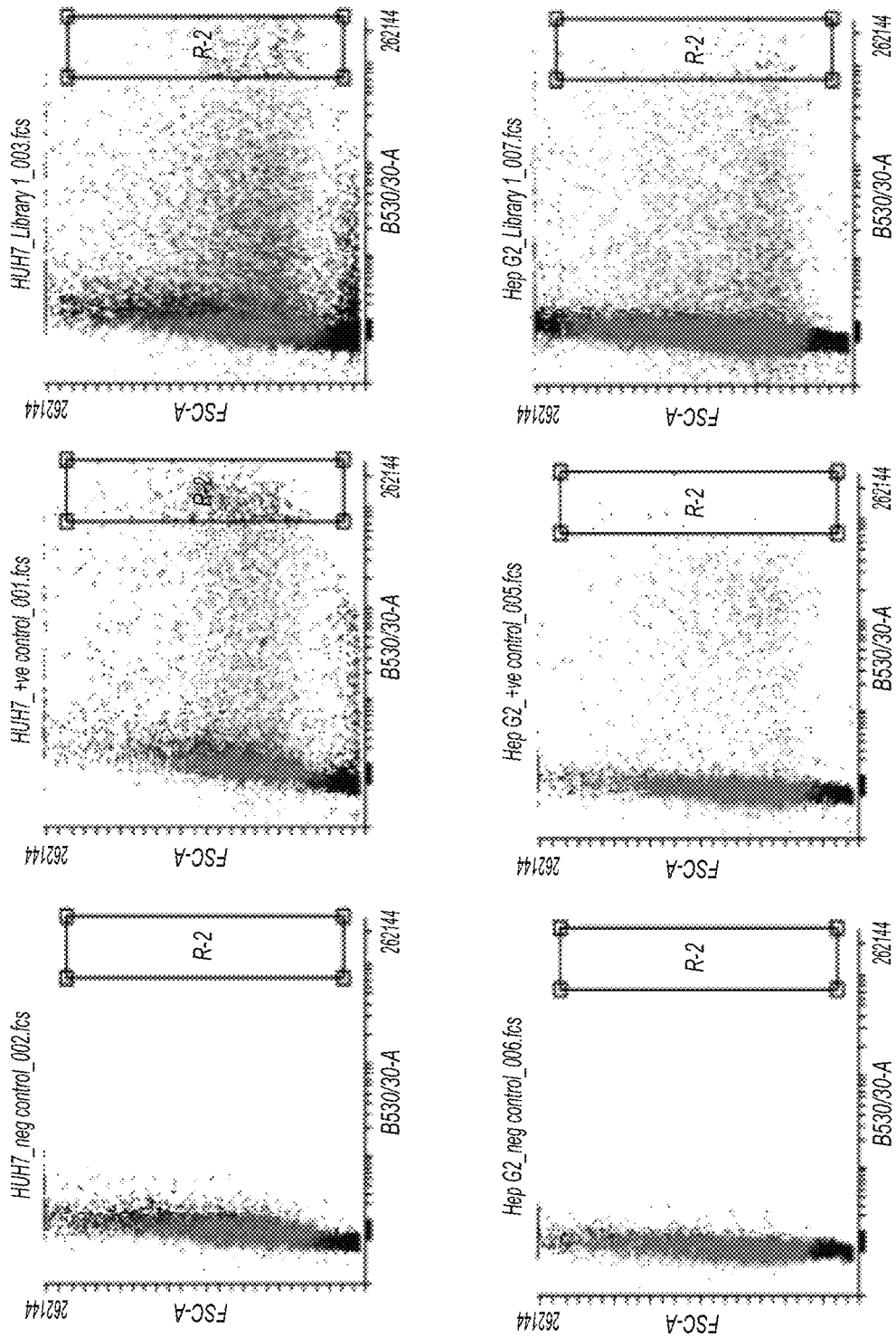
FIG. 5 shows FACS screening of promoter libraries in Huh7 and HepG2 cells.
Figure 6B:
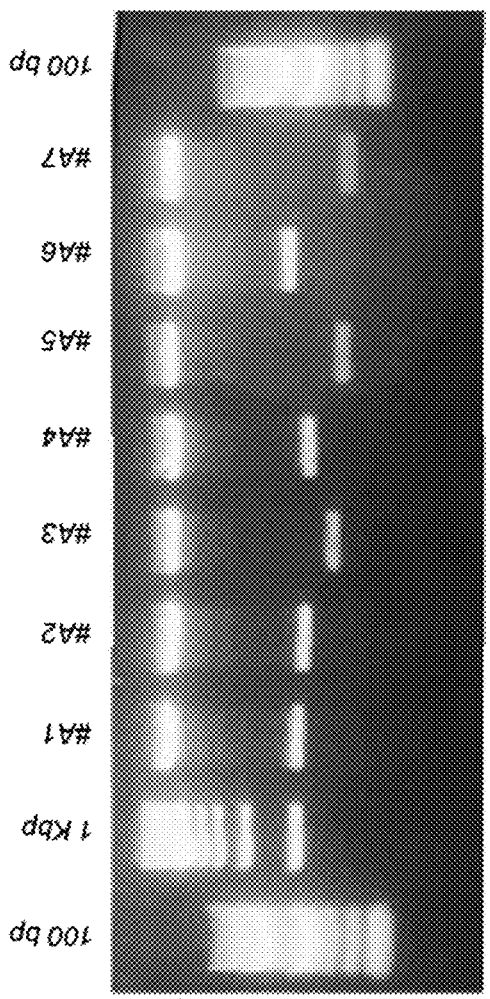
FIG. 6A-C shows PCR rescue of individual promoter candidates. A. Shows data from HepG2 and Huh7 cells. B. Shows data from A1-A7. C. Shows data from A8-A11.
Figure 6C:
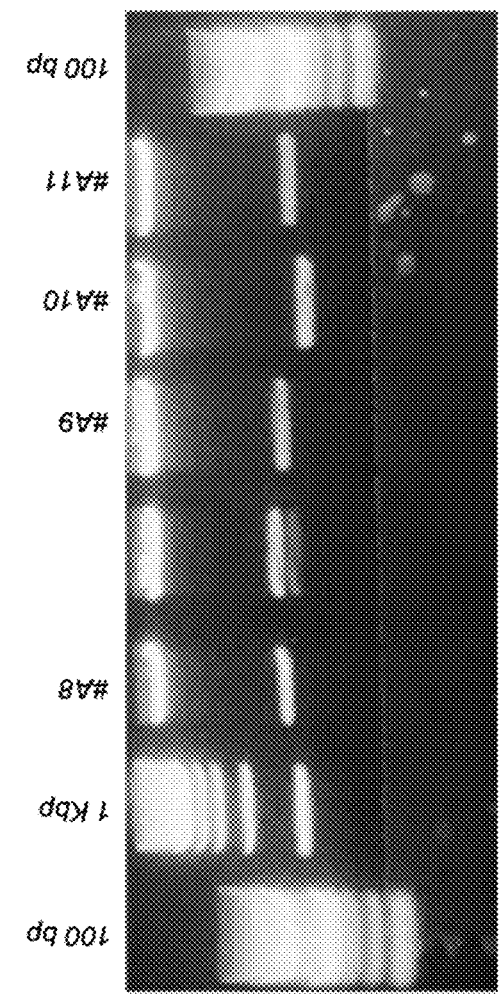
Figure 6A:
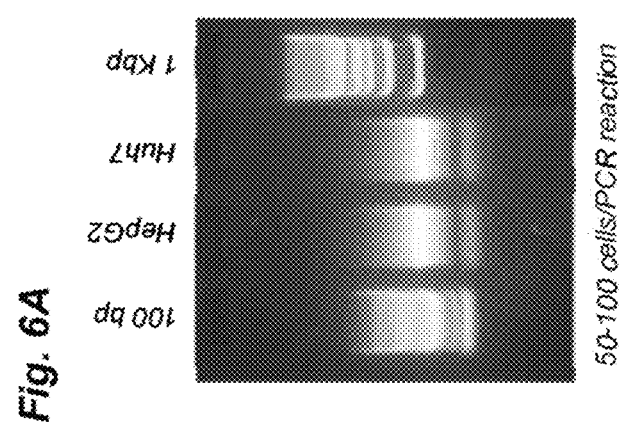

Example 7—Assessment of Promoter Candidate Activity from Liver Cell Library Using FACS Analysis The liver-specific synthetic promoter library was then transfected into both Huh7 and HepG2 cells using the FugeneHD reagent. After 24 hours, GFP expression was assessed by FACS and cells were sorted if they displayed a fluorescence intensity greater than 104 units (FIG. 5). Sorted cells were then lysed and promoter candidates rescued by PCR. FIG. 6 illustrates the promoters rescued from HepG2 cells (A1 to A7, Panel B) and promoters rescued from Huh7 cells (A8 to A11; Panel C). The promoter sizes ranged from 200 to 700 bp.

Figure 7:
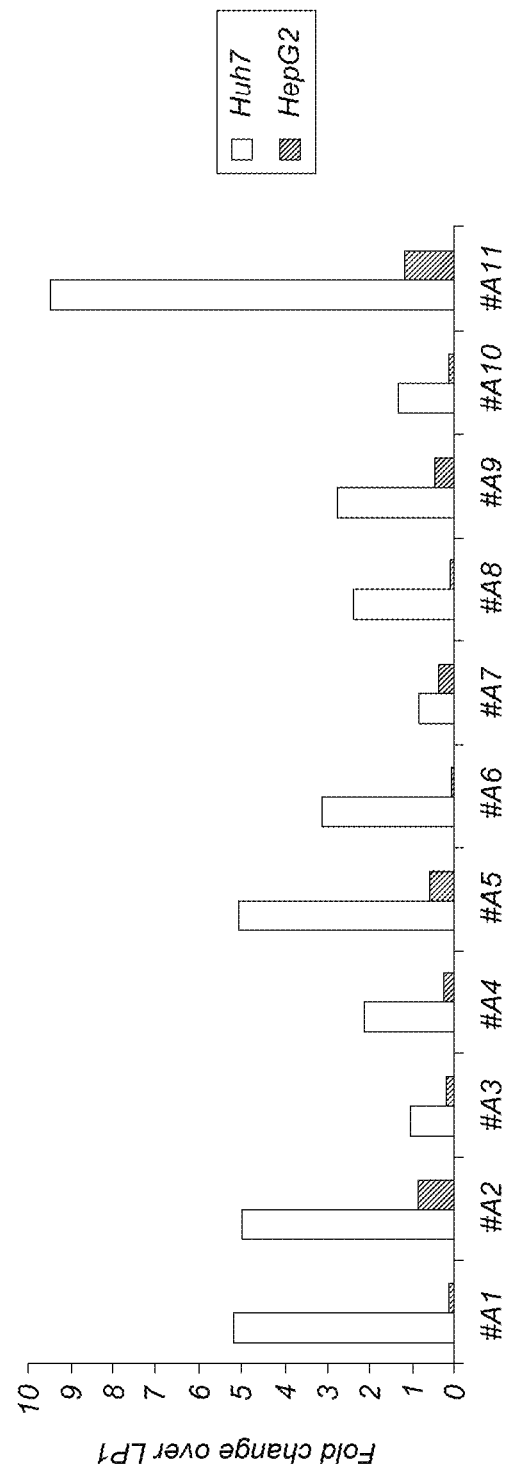
FIG. 7 shows validation of activity of 11 identified promoters from the library screen in HepG2 and Huh7 cells. Left bar Huh7 cells; right bar HepG2 cells.

The 11 promoter candidates (A1-A11) rescued from the FACS screening of transfected HepG2 and Huh7 cells were sub-cloned into pGL4.10 upstream of the firefly luciferase gene and their activity was then validated by luciferase assay (FIG. 7). In this example, the best isolated promoter candidates were always consistently more active in Huh7 cells, no matter which cell type the promoters were screened in (i.e. derived from HepG2 versus Huh7).

Figure 28:
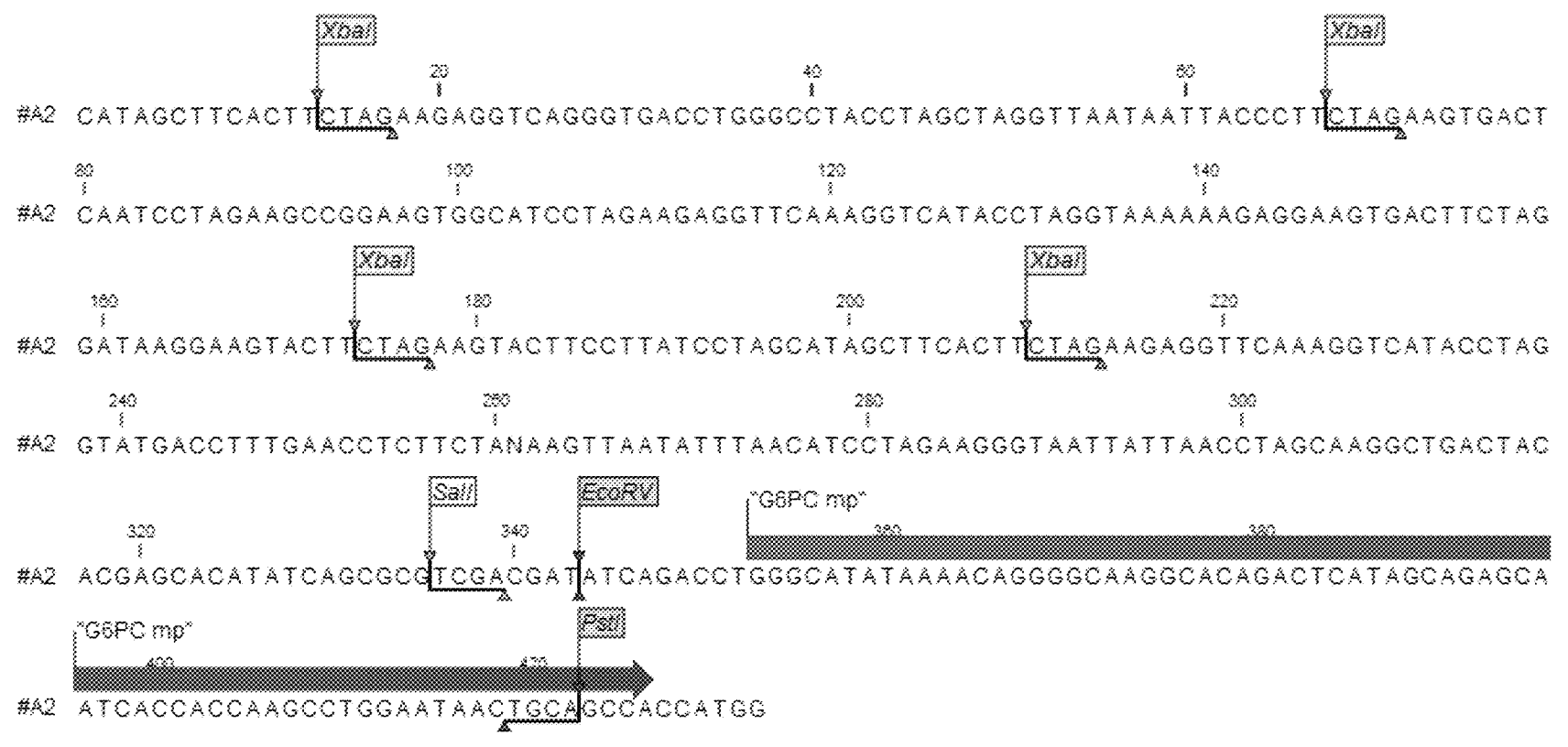
Figure 29:
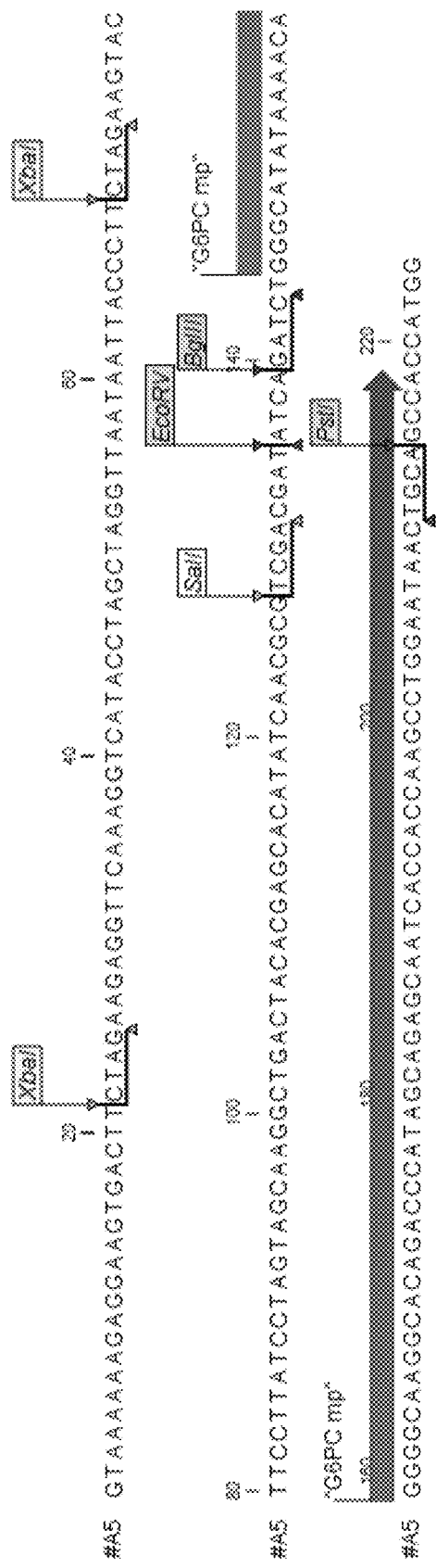
FIG. 29 shows a diagram of #A4 (SEQ ID NO:37).
Figure 30:
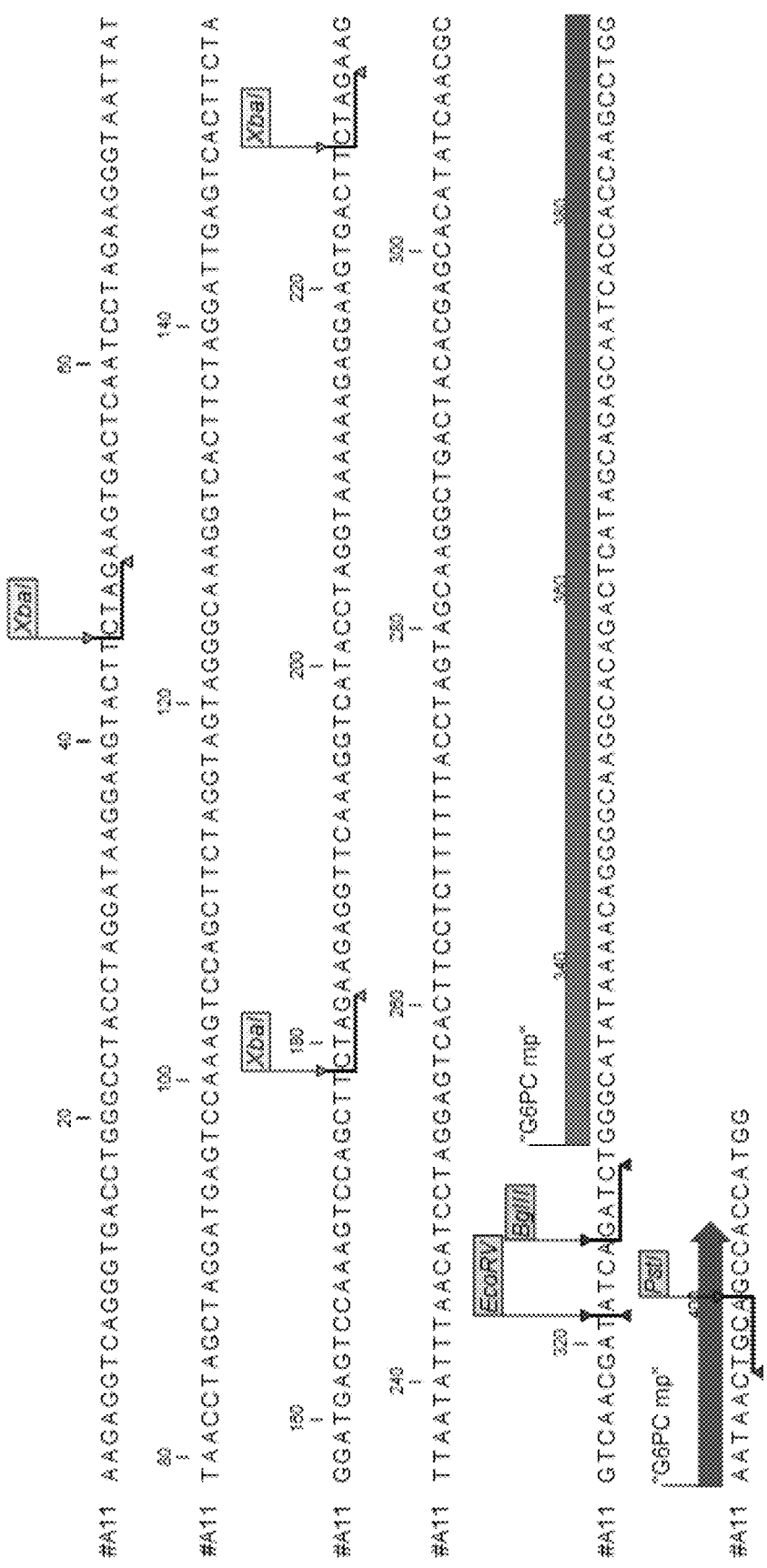
FIG. 30 shows a diagram of #A11 (SEQ ID NO:38).

The activity of promoter candidates in primary human hepatocytes was assessed. After determining the optimal transfection conditions for these cells, we transfected the primary hepatocytes with promoter candidates #A2, #A4, and #A11 and monitored expression using the luciferase reporter system (FIG. 8). The LP-1 promoter had limited activity in primary hepatocytes and synthetic promoters #A2 and #A4 were up to five-fold more active in this cell type. Diagrams of #A2, #A5, and #A11 are shown in FIGS. 28-30.

Figure 9:
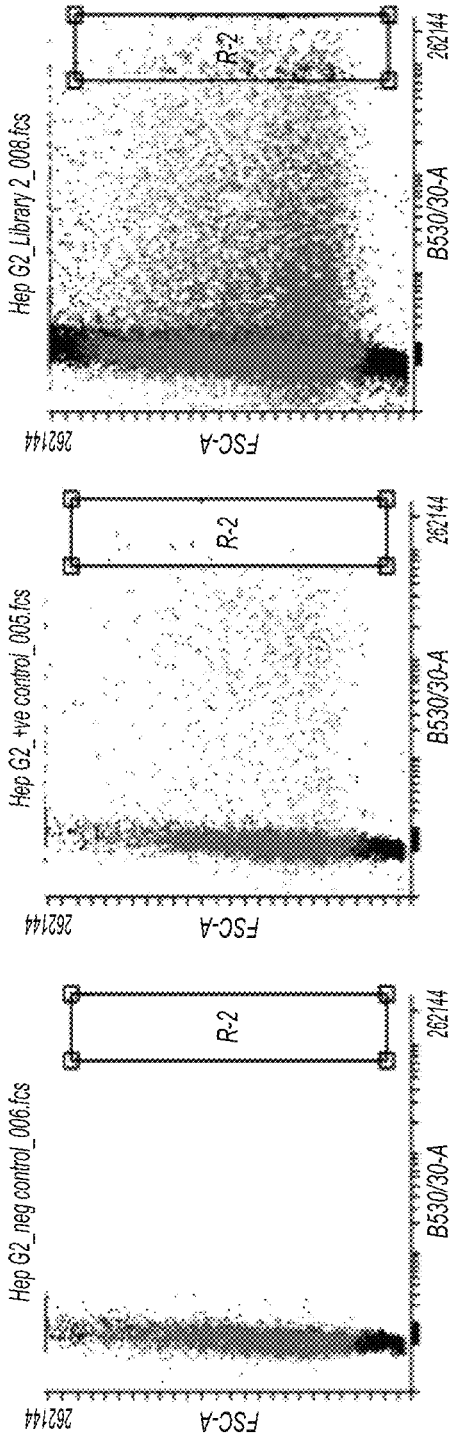
FIG. 9 shows an example of secondary FACS screening in HepG2 cells.

The results from the PCR rescue (FIG. 6A) illustrate that the inventors were able to rescue a broad range of promoters from the preliminary screen. Rather than attempt to isolate individual clones from this range of promoters, a secondary screen was conducted, whereby all fragments from the PCR rescue were re-cloned into the screening vector and re-screened in both Huh7 and HepG2 cells (FIG. 9).

Individual promoter candidates rescued from the secondary screen were then inserted upstream of the firefly luciferase gene in pGL4.10 and the levels of expression mediated by each individual promoter were determined by luciferase assay (FIG. 10). Promoter B1 was isolated from both a primary and secondary screen in HepG2 cells, promoters B2, B3 and B4 were isolated from a primary screen in Huh7 cells and a secondary screen in HepG2 cells, whereas promoter B5 was isolated from both a primary and secondary screen in Huh7 cells. From this secondary screen, only promoter B4 was more active than the LP-1 promoter and was 3-fold more active in HepG2 cells and 7-fold more active in Huh7 cells.

The activity of promoter B4 was compared to the LP-1 promoter in human primary hepatocytes (FIG. 11). It was determined that promoter candidate B4 was 2.5-fold more active. When compared B4 to the other promoter candidates, B4 is as active as A5, but shows half the activity of A2 in the human primary hepatocytes.

Figure 12:
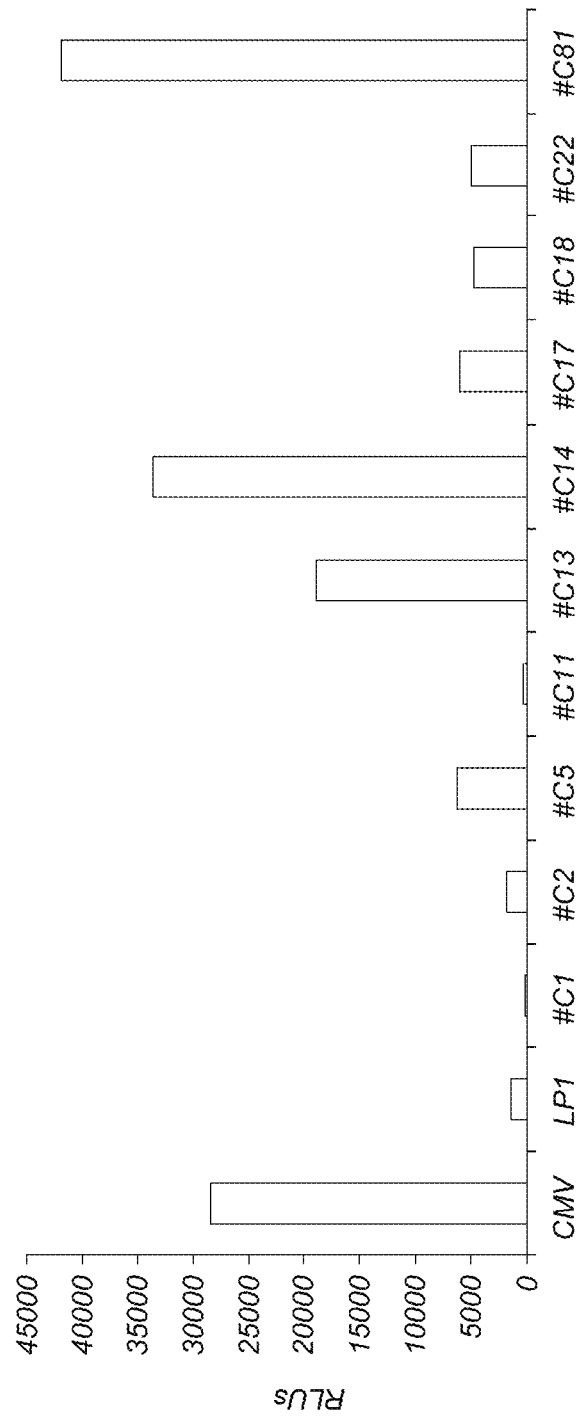
FIG. 12 shows validation of activity of 10 identified promoters from the library screen in primary hepatocytes.

The original liver-specific synthetic promoter library was screened in human primary hepatocytes using the FACS-based screen and PCR-rescue approach described above. Hepatocytes were transfected with the library using FugeneHD, gated according to an identical gating strategy as used in the liver cell lines and sorted cells were lysed and promoters rescued as previously described. Individual promoters were then cloned into pGL4.10 and the expression of luciferase monitored (FIG. 12). The results from the screen in primary hepatocytes revealed than promoters #C13, #C14 and #C81 were much more active than the LP-1 promoter (FIG. 12). This transfection was repeated in order to confirm this observation and found that promoter #C14 was consistently more active than LP-1, where it was 12-fold more active (FIG. 13).

Figure 14A:
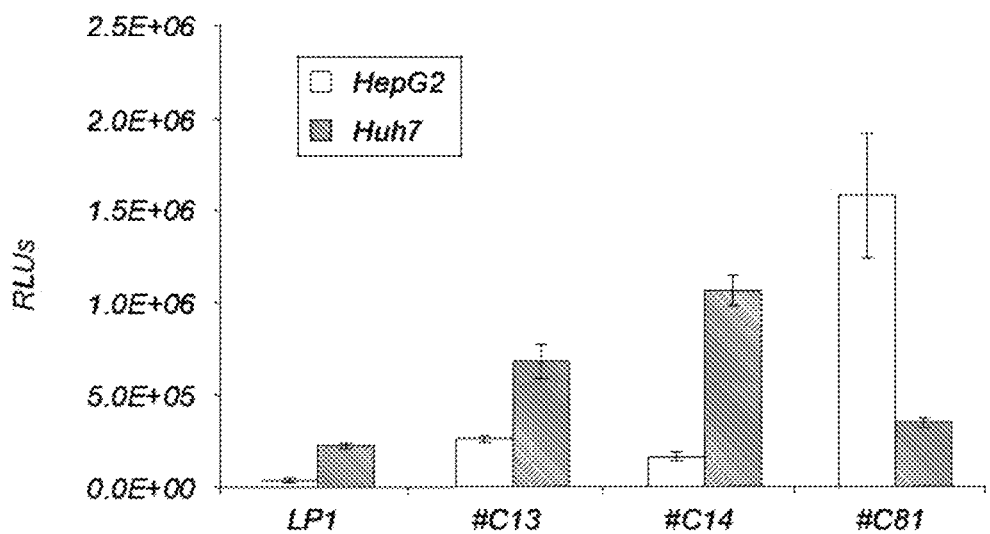
FIG. 14 shows activity of promoters isolated in primary hepatocytes in different cell lines. A. Shows RLUs. B. Shows fold change over LP1. Left bar HepG2 cells, right bar Huh7 cells.
Figure 14B:
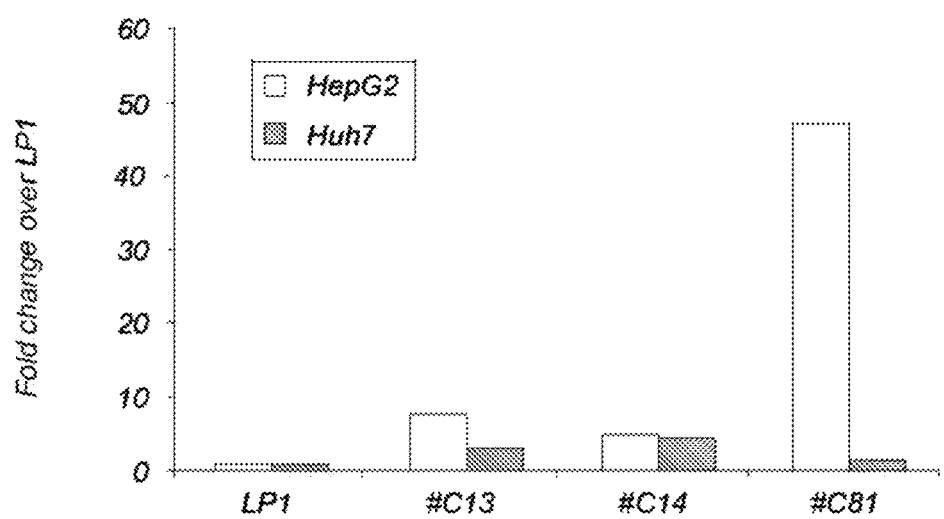

The activities of promoters #C13, #C14 and #C81 was examined in the liver cell lines HepG2 and Huh7 in order to monitor how promoter activity varied across cell types (FIG. 14). In this example, all promoters isolated from primary hepatocytes were more active in HepG2 cells compared to Huh7 (C81 was nearly 50-fold more active than LP-1 in HepG2 cells). Promoter #C14 was consistently more active than the LP-1 promoter in primary hepatocytes, HepG2 cells and Huh7 cells. Table 6 summarizes the expression activities of selected promoter candidates isolated from the different library screens across different liver cell types.

TABLE 6

|     | HepG2 | Huh7 | Hepatocytes |
|-----|-------|------|-------------|
| A2  | 1x    | 5x   | 5x          |
| A5  | 0.5x  | 5x   | 3x          |
| A11 | 1.5x  | 10x  | 0.5x        |
| B4  | 3x    | 7x   | 3x          |
| C13 | 10x   | 2.5x | 0.5x        |
| C14 | 5x    | 5x   | 12x         |
| C81 | 50x   | 1.5x | 2x          |

Figure 32:
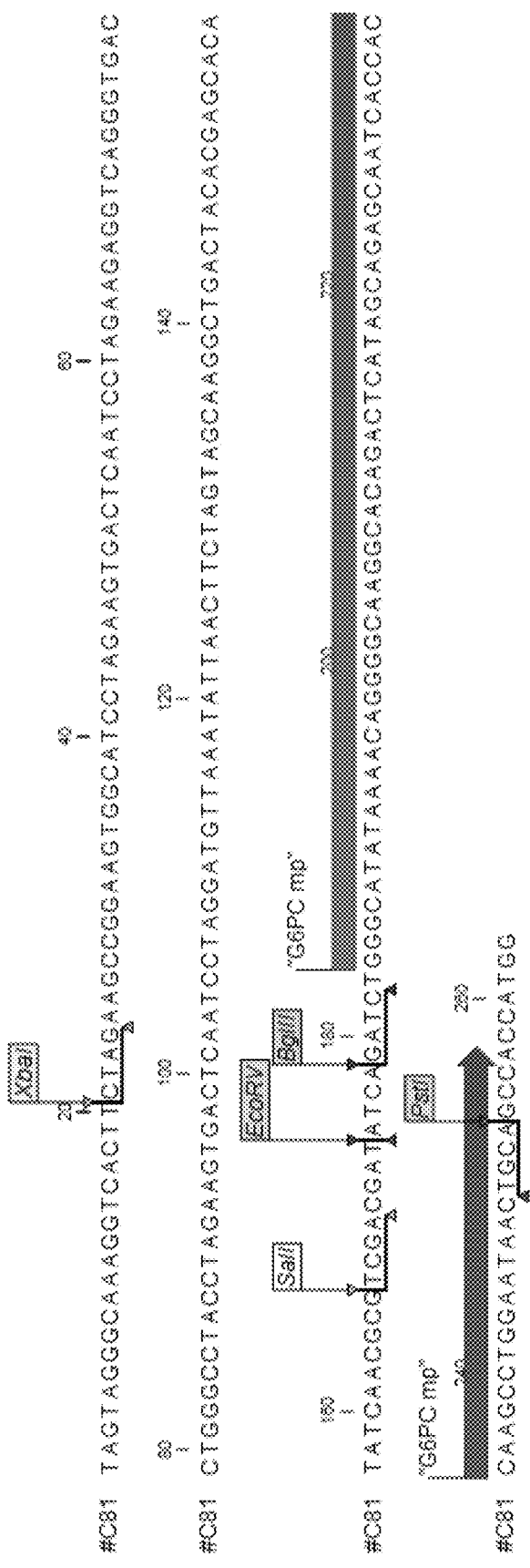
FIG. 32 shows a diagram of #C81 (SEQ ID NO:40).

In this example, promoters #B4 and #C14 were consistently more active across all cell types and in different experiments. Promoter #C13 and #C81 displayed significant variability in activity in hepatocytes in different experiments but also show high levels of expression across different cell types. Diagrams of #C13 and #C81 are provided in FIGS. 31 and 32.

Example 8—Rational Design of Promoter Candidates

In addition to the random shuffling approach to preparing promoter candidates described in Examples 1-7, the inventors additionally used a rational design approach for preparing further novel promoter candidates. Several cis-acting regulatory elements (CREs) containing evolutionary conserved clusters of transcription factor binding site motifs are known and CRM8 has been identified as being particularly potent for expression in the liver. Accordingly, the −137/−37 fragment derived from SERPINA1 was used as starting point for the rational design of variants of HS_CRM8 (De Simone et al. "Cis- and trans-acting elements responsible for the cell-specific expression of the human α1-antitrypsin gene", The EMBO Journal, vol. 6, no. 9, pp. 2759-2766, 1987). Based on bioinformatic predictions a shorter sequence with putative TSS activity was chosen and placed in the 3' end of the synthetic cis-regulatory module (CRM). Orientation and position of the CREs was decided based on bioinformatic predictions and inferred hierarchy of positive and negative interplays between liver specific transcription factors from extensive literature review. The activity of this rationally designed CRM (also referred to as Composite enhancer element) was tested in various difference liver cell types.

Figure 15A:
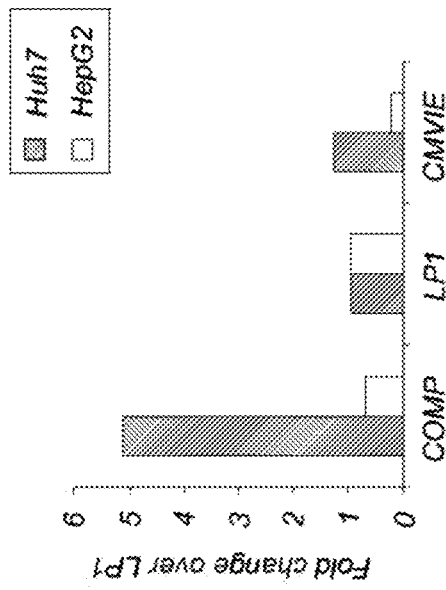
FIG. 15A-C shows fold-activity compared to LP-1 of a composite synthetic promoter in different cell types. A. Shows RLUs. B. Shows fold change over LP1. A. Shows a schematic of the composite synthetic promoter. Left bar Huh7 cells; right bar HepG2 cells.
Figure 15B:
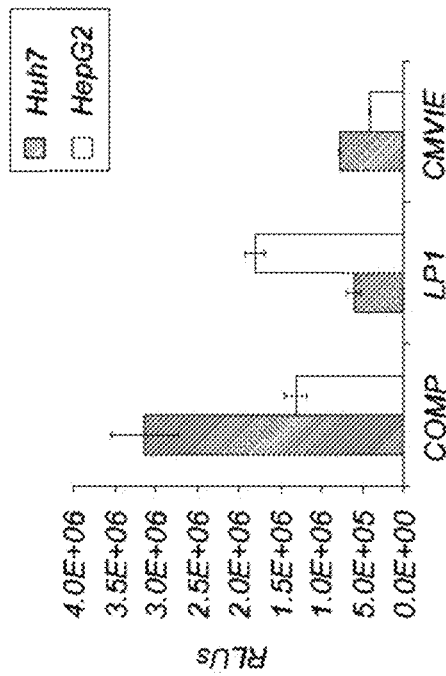
Figure 15C:
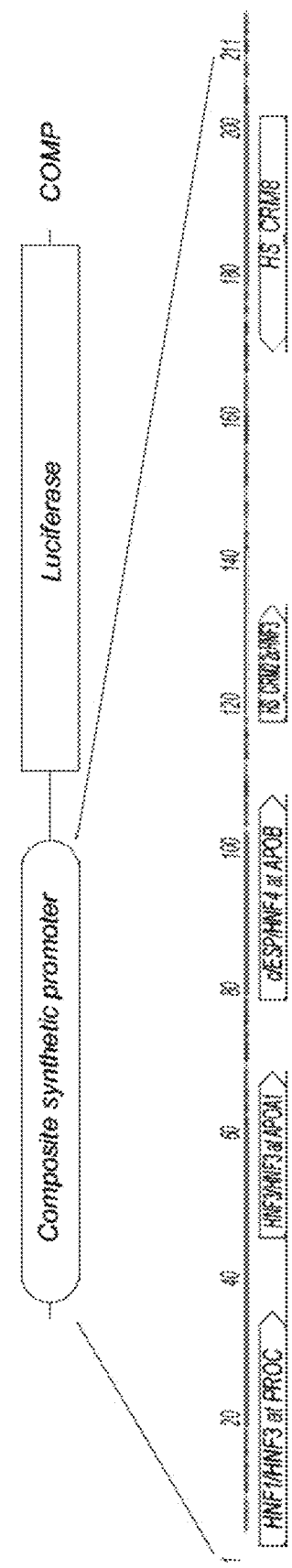

The activity of the rationally designed CRM was examined in different liver cell types. This first iteration of the liver specific CRM showed significant transcriptional activity (FIG. 15).

The data shows that on its own (i.e. without an operably linked minimal promoter), the CRM was as active as the LP-1 promoter in HepG2 cells and 5-fold more active in Huh7 cells.

Figure 16:
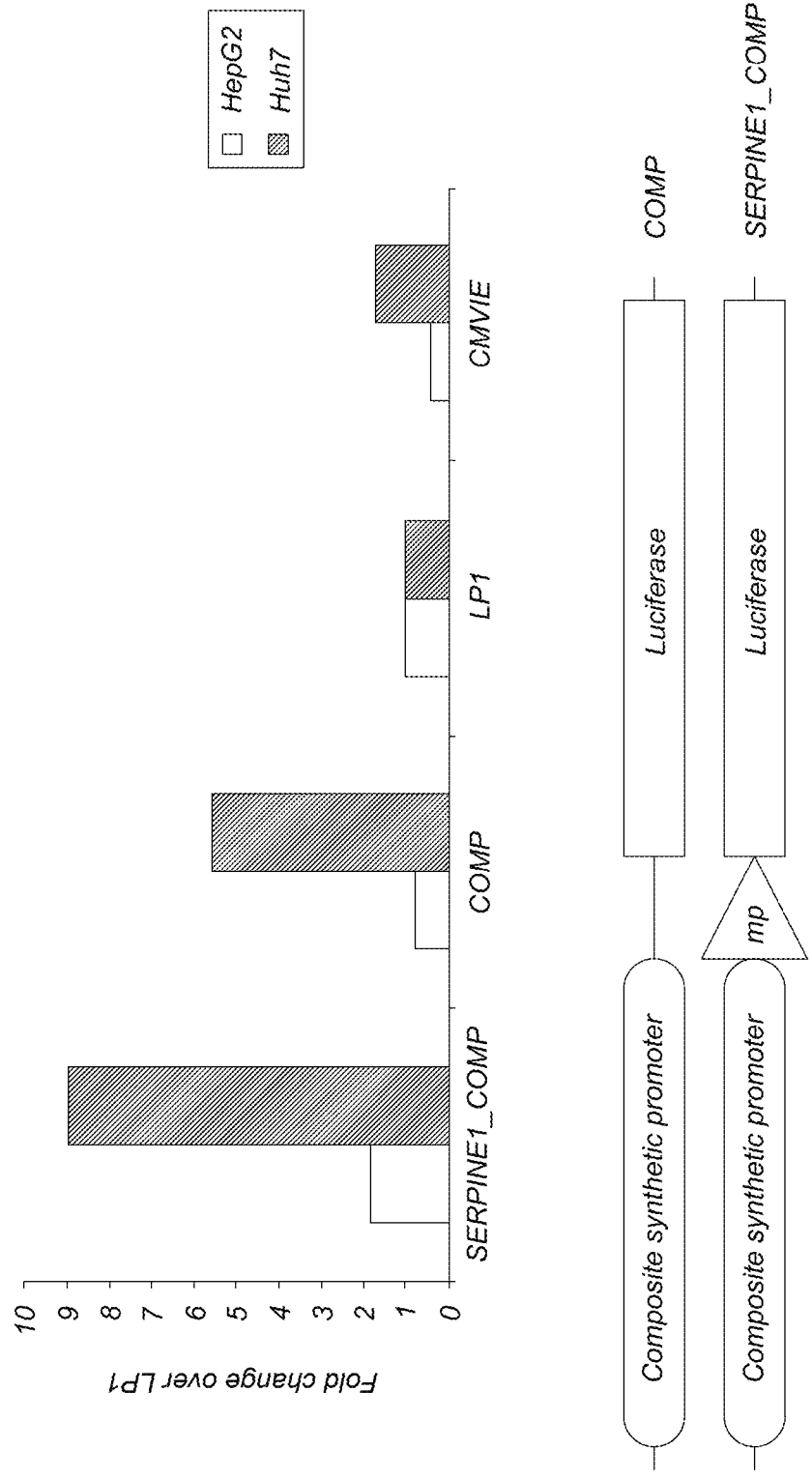
FIG. 16 shows the effect of SERPINE1 on the activity of the Composite enhancer. Left bar HepG2 cells; right bar Huh7 cells.

Next, the CRM was cloned upstream of the SERPINE1 minimal promoter to determine if the CRM would act as a transcriptional enhancer. Expression strength was examined (FIG. 16)

The addition of a minimal promoter downstream of the CRM boosted expression strength so that its activity was 9-fold higher than LP-1 in Huh7 cells and 2-fold more active than LP-1 in HepG2 cells.

Figure 17:
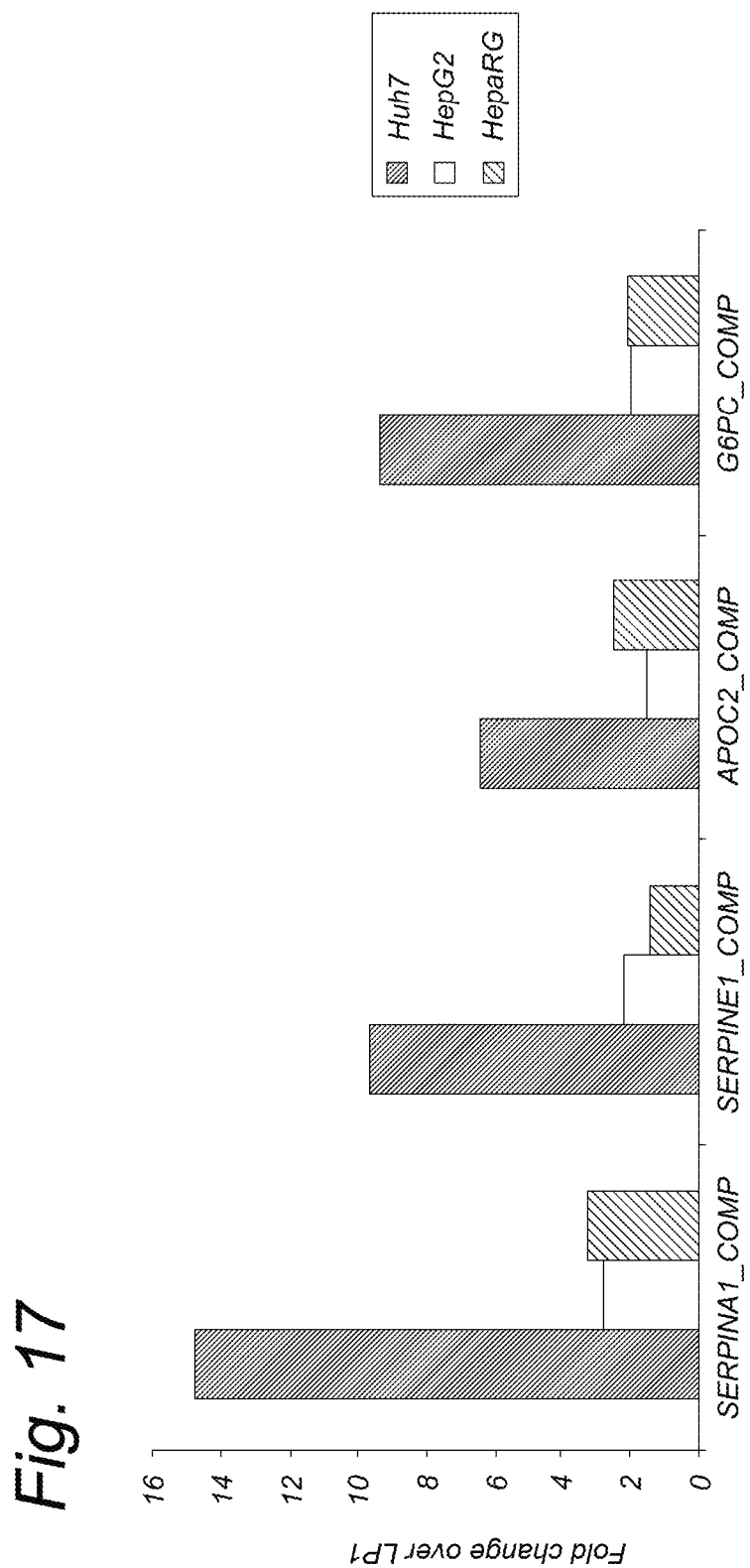
FIG. 17 shows the effect of different minimal promoters on Composite enhancer activity. Left bar Huh7 cells, middle bar HepG2 cells, right bar HepaRG.

Next, the effect of each minimal promoter on the activity of the CRM was examined in three different liver cell lines; HepG2, Huh7 and HepaRG (FIG. 17). All minimal promoters mediated a similar boost in expression strength, but SERPINA1 mediated the highest increase in expression strength of the CRM.

Figure 18:
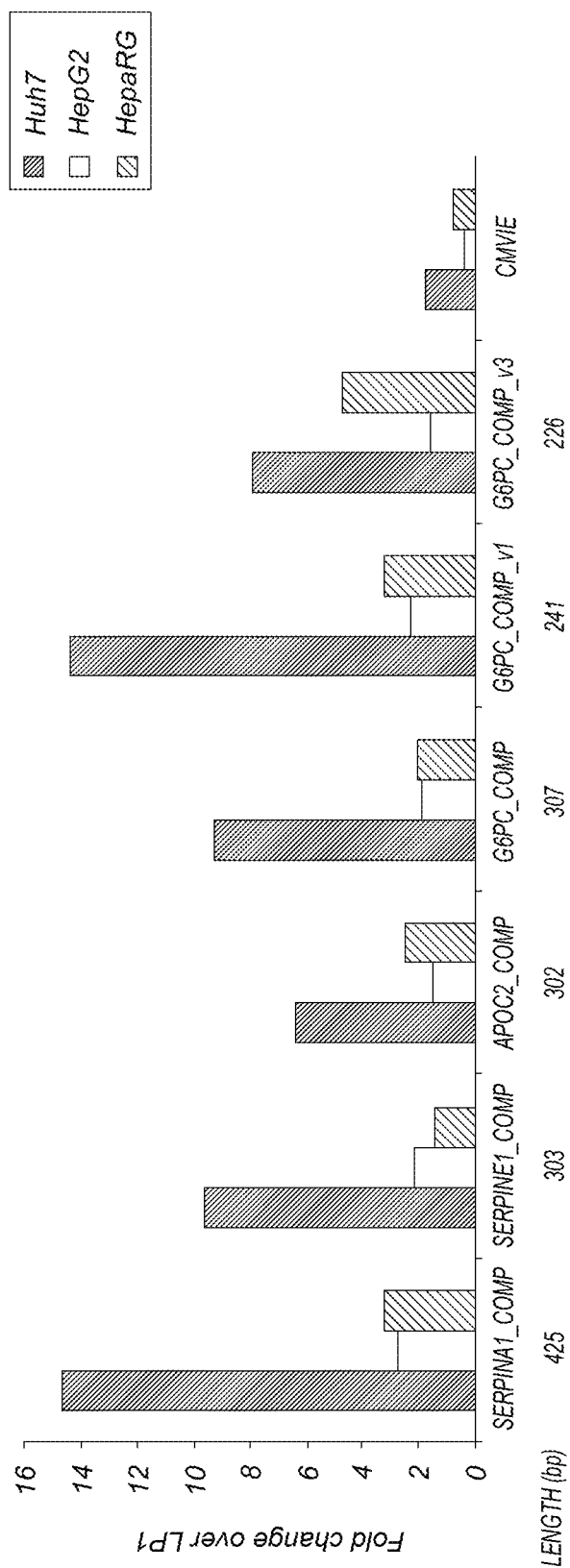
FIG. 18 shows reduction of promoter size and influence on expression strength. Left bar Huh7 cells, middle bar HepG2 cells, right bar HepaRG.

Given the importance of promoter size on the selection of suitable promoters for further analysis in vivo, the promoters derived from the G6PC minimal promoter were further modified in order to reduce overall size by removing spacers and monitor the effect of size reduction on promoter activity. By removing spacer elements to reduce size from 307 bp to 241 bp, the inventors were able to slightly increase activity of the promoter. Reducing its size further to 226 bp had a negative effect on expression strength in Huh7 and HepG2 cells, but a positive effect on strength in HepaRG cells. FIG. 18 shows the activity of all rationally designed promoters in different cell types and the size of each promoter.

Figure 19:
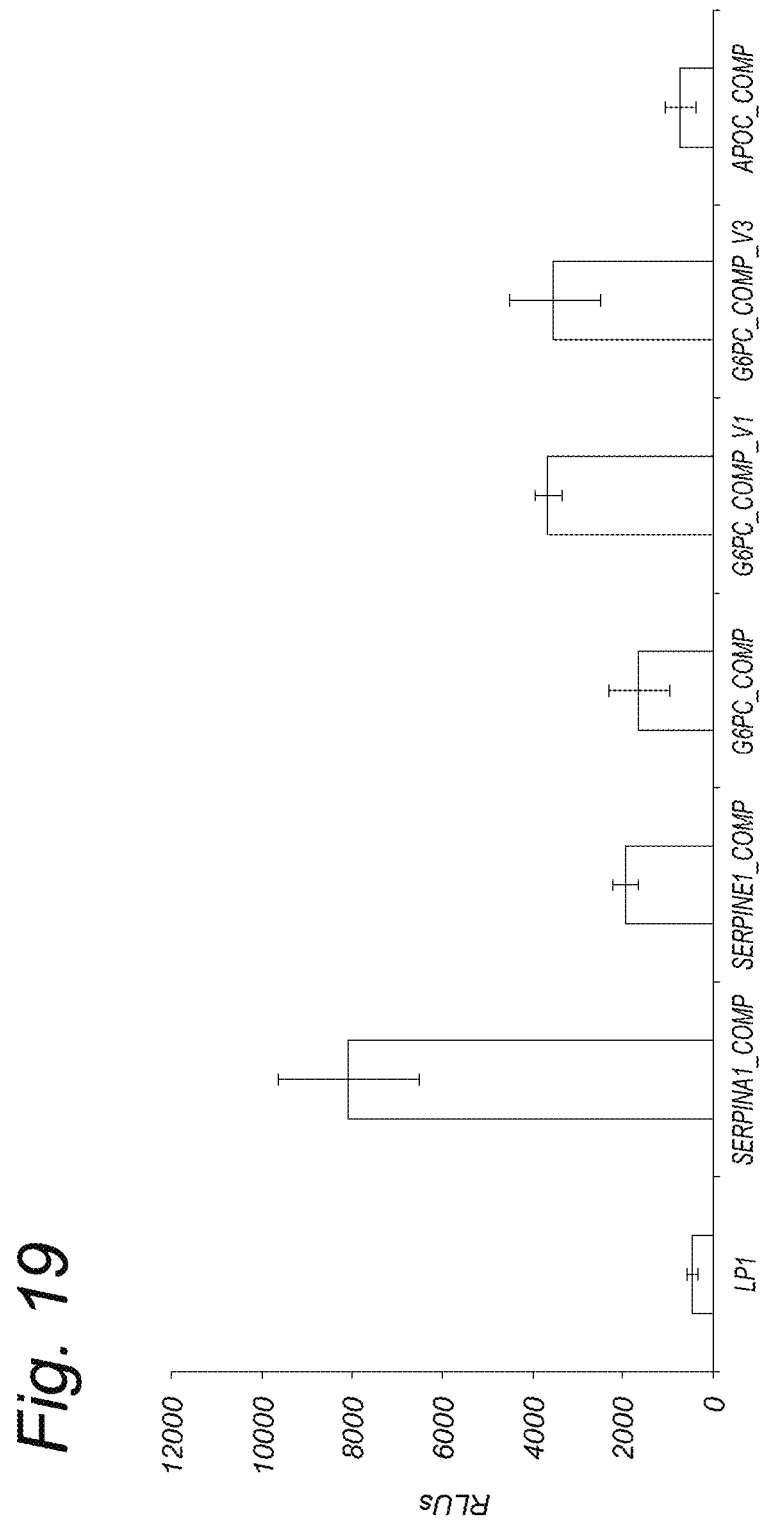
FIG. 19 shows expression strengths of rational-designed promoters in primary hepatocytes.

The activity of rationally designed promoters was examined in primary human hepatoctyes. Primary cells grown in 2% FBS were transfected with synthetic promoter constructs expressing firefly luciferase using FugeneHD using the conditions described herein. The results of the transfections are shown in FIG. 19. The levels of expression in hepatocytes mediated by rationally-designed promoters were much higher than expression levels mediated by the LP-1 promoter. The expression profile was similar to that seen in the liver cell lines in that SERPINA1 mediated the highest levels of protein expression when compared to other minimal promoter constructs.

A summary of the fold-increase expression over the LP-1 promoter for each rationally-designed promoter, as assessed in different cell types, is presented in Table 7.

TABLE 7

|              | Size (bp) | HepG2 | Huh7 | HepaRG | Hepatocytes (2% FBS) |
|--------------|-----------|-------|------|--------|----------------------|
| SERINA1_COMP | 424       | 3x    | 14x  | 3x     | 18x                  |
| SERINE1_COMP | 303       | 2x    | 10x  | 1x     | 4x                   |
| G6CP_COMP    | 307       | 1.5x  | 6x   | 2x     | 4x                   |
| G6CP_COMP    | 241       | 2x    | 9x   | 2x     | 8x                   |

TABLE 7-continued

| | Size (bp) | HepG2 | Huh7 | HepaRG | Hepatocytes (2% FBS) |
|---|---|---|---|---|---|
| G6CP_COMP | 226 | 2x | 14x | 2.5x | 8x |
| APOC2_COMP | 302 | 1.5x | 8x | 2x | 2x |

In this example, it was found that the LP-1 promoter was most active in HepG2 and HepRG cells and least active in Huh7 and primary human hepatocytes. This meant that when comparing the activities of the different synthetic promoter candidates with LP-1, a higher fold-increase in Huh7 and primary human hepatocytes was witnessed. It was surprising that LP-1 had very limited activity in primary cells, suggesting that this may be a consequence of how the promoter was designed and selected.

Example 9—Testing Liver Cell Promoter Sequences in a Panel of Cell Lines to Demonstrate Specificity and Activity Under a Profile Comparable to the LP1 Promoter The activity of the different promoter candidates in cell lines derived from other tissues was assessed. Hela (ovarian cancer), 293 (human embryonic kidney) and A549 (lung adenocarcinoma) cells were transfected with all the identified synthetic promoter candidates with a view to determine the level of specificity each promoter had for liver cells.

Figure 20:
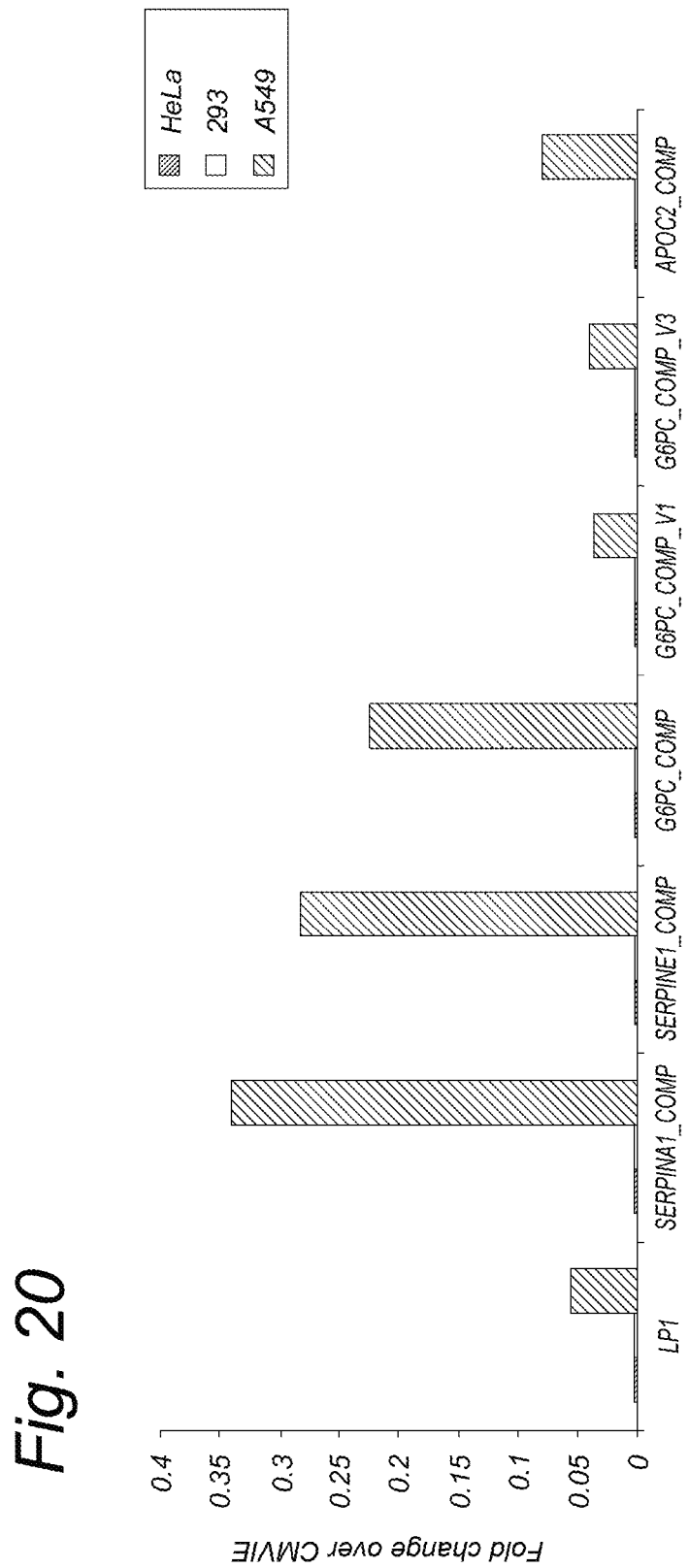
FIG. 20 shows the activity of rationally-designed promoters in non-liver cells.

The activity of the promoters was then compared to the activity of expression mediated by the CMVIE promoter in that cell type. FIG. 20 shows that the LP-1 promoter had 5% of the activity of CMVIE in A549 cells, but no activity in the other two cell types. Of the synthetic promoters, G6PC_COMP_V1, G6PC_COMP_V3 and APOC2_COMP all mediated a similar level of expression in A549. Whereas SERPINA1_COMP, SERPINE1_COMP and G6PC_COMP mediated higher levels of expression in these cells. In this example, no promoter construct showed any measurable activity in 293 and Hela cells.

Figure 21:
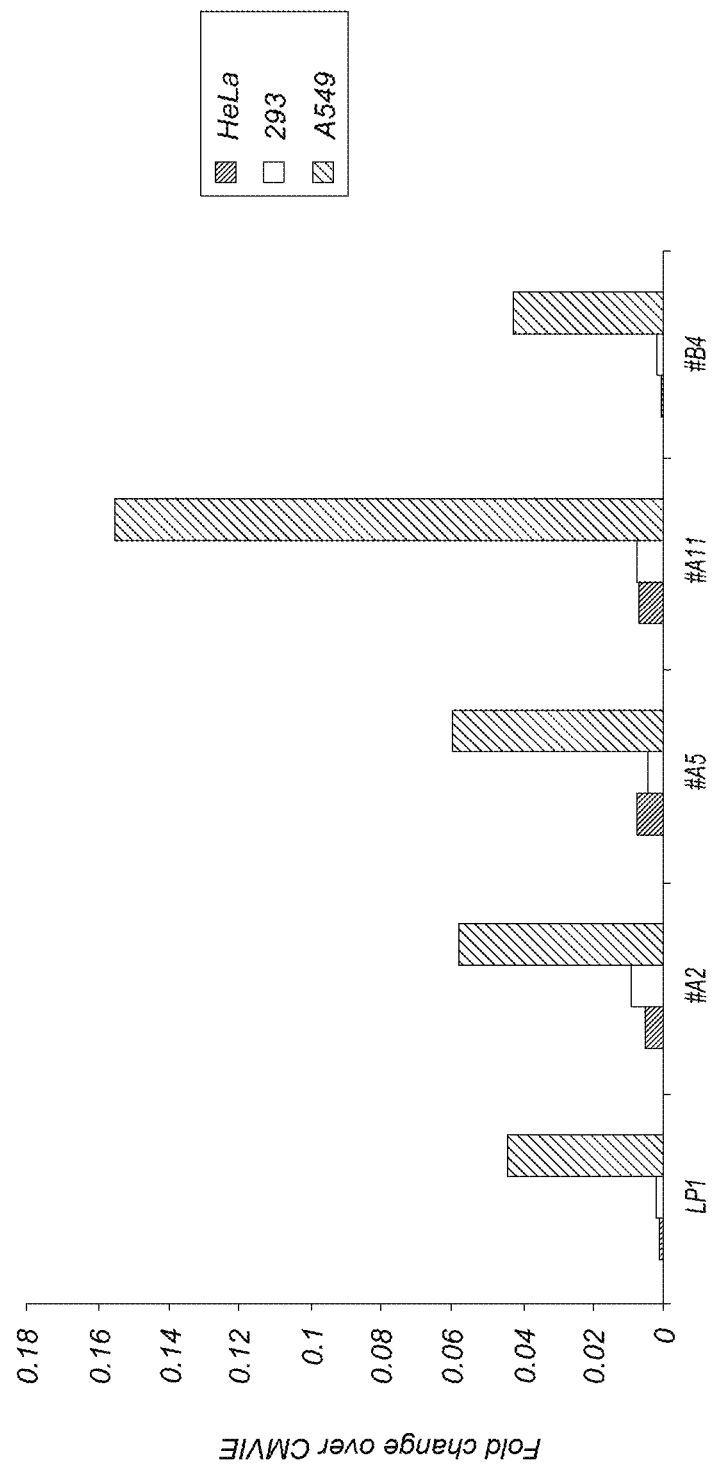
FIG. 21 shows the activity of cell line library screened promoters in non-liver cells. Left bar HeLa cells, middle bar 293 cells, right bar A549 cells.

Next, the activity of library-screened promoters was assessed in the different non-liver cell lines. From the promoters screened in the liver cell lines Huh7 and HepG2, A2, A5 and B4 showed a similar level of specificity displayed by the LP-1 promoter, i.e. they mediated no expression in 293 and Hela cells, and less than 5% expression of CMV in A549 cells (FIG. 21). Promoter A11 showed significantly higher levels of expression (>15% expression of CMVIE) in A549 cells compared to the other promoter candidates.

Figure 22:
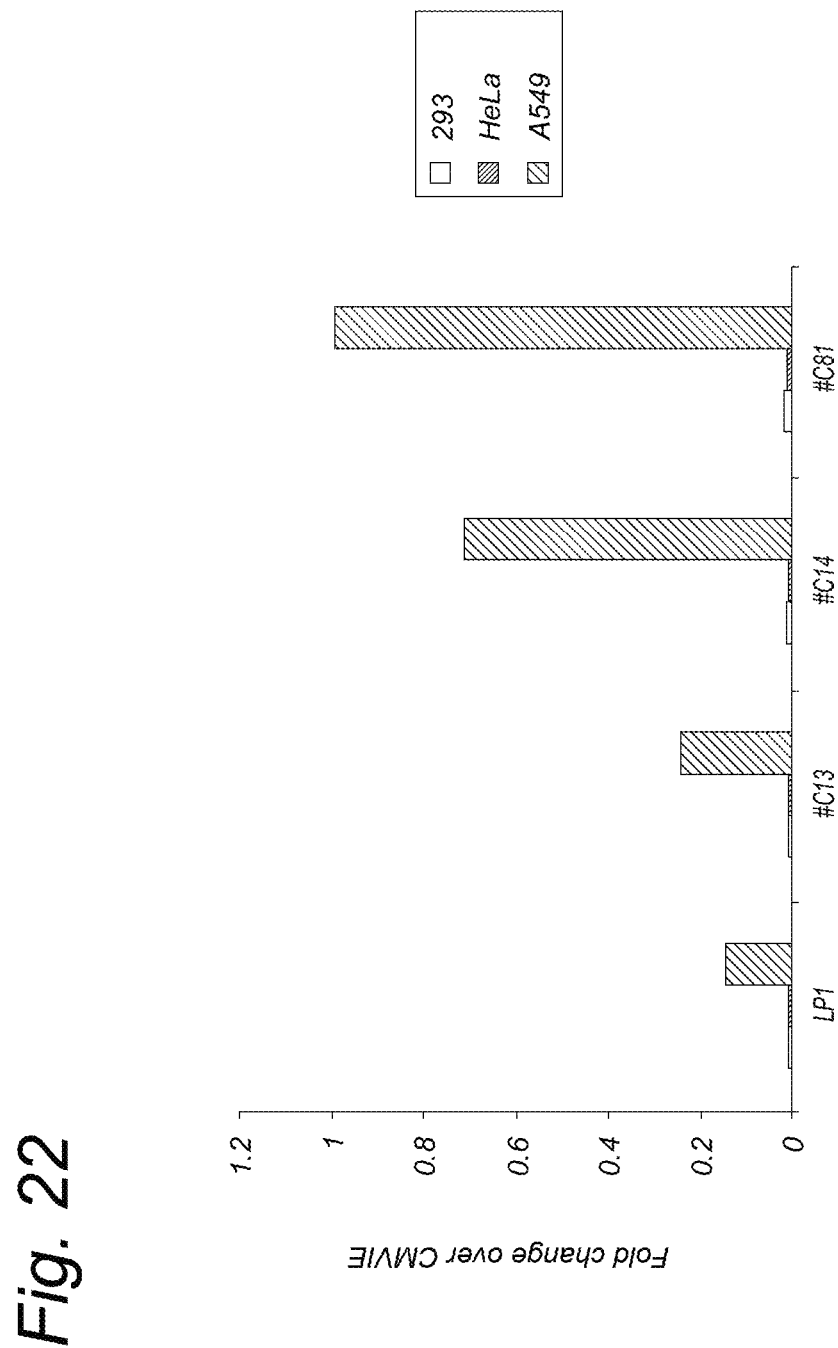
FIG. 22 shows activity of primary hepatocyte library screened promoters in non-liver cells. Left bar 293 cells, middle bar HeLa cells, right bar A549 cells.

The specificity of promoters derived from the hepatocyte-screened library was tested in the three selected non-liver cell lines (FIG. 22). In this experiment, the LP-1 promoter mediated almost four times the amount of expression in A549 cells than it had previously (18% of CMVIE). In general, activity in A549 cells was higher than had been previously observed. In particular, promoter #C14 (60% of CMVIE) and #C81 (90% of CMVIE) mediated high levels of expression in A549, whereas #C13 (22% of CMVIE) mediated similar levels of expression as seen with the LP-1 promoter. As had been observed with all other promoters, promoter candidates derived from the screen in the primary hepatocytes showed no measurable activity in 293 and Hela cells.

Sequences of promoter sequences selected as used in FIGS. 7-14 and 21-22 correspond to SEQ ID NO:36 (#A2), SEQ ID NO:37 (#A4), SEQ ID NO:38 (#A11), SEQ ID NO:39 (#C13), SEQ ID NO:40 (#C81), SEQ ID NO:32 (#B4), SEQ ID NO:34 (#C14). Sequences of promoter sequences selected as used in FIGS. 15-20 correspond to SEQ ID NO:23 (COMP), SEQ ID NO:30 (SERPINE1_COMP), SEQ ID NO:29 (SERPINA1_COMP), SEQ ID NO:21 (APOC2_COMP), SEQ ID NO:25 (G6PC_COMP), SEQ ID NO:26 (G6PC_COMP_v1), SEQ ID NO:28 (G6PC_COMP_v3).

Exemplary features of each promoter are listed in the table below.

TABLE 8

| | Size (bp) | HepG2 | Huh7 | HepaRG | Hepatocytes | AS49 (% of CMV) |
|---|---|---|---|---|---|---|
| SERINA1_COMP | 424 | 3x | 14x | 3x | 8x | 33% |
| SERINE1_COMP | 303 | 2x | 10x | 1x | 4x | 27% |
| G6CP_COMP | 307 | 1.5x | 6x | 2x | 4x | 25% |
| G6CP_COMPv1 | 241 | 2x | 9x | 2x | 20x | 5% |
| G6CP_COMPv3 | 226 | 2x | 14x | 2.5x | 12x | 5% |
| APOC2_COMP | 302 | 1.5x | 8x | 2x | 0.5x | 9% |
| A11 | 410 | 1.5x | 10x | — | 0.5x | 15% |
| B4 | 259 | 3x | 7x | — | 3x | 6% |
| C13 | TBD | 10x | 2.5x | — | 0.5x | 22% |
| C14 | 287 | 5x | 5x | — | 12x | 60% |
| C81 | 263 | 50x | 1.5x | — | 2x | 90% |

Example 10—Shortening and Modifications of Liver Specific Promoter Sequences G6PC_COMP_v1, #B4 and #C14

Figure 23A:
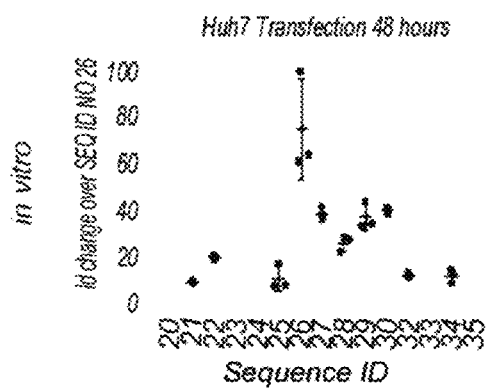
FIG. 23A-E shows a comparison of in vitro versus in vivo expression of a reporter gene. These figures show that the promoter drives the expression of a reporter gene in both in vitro and in vivo experiments. All constructs were tested both in plasmid (transfection; Panels A and B) as well as AAV encapsulated form (transduction; Panels C and D). There is a clear robust response between all the assays. Two controls were included: LP1 promoter as reference liver promoter and a buffer (vehicle) control as negative. In Panel E, it is apparent that DNA copies of the DNA delivered to the mouse liver are comparable for all constructs and therefore the performance of the promoter is valid and confirmed.
Figure 23B:
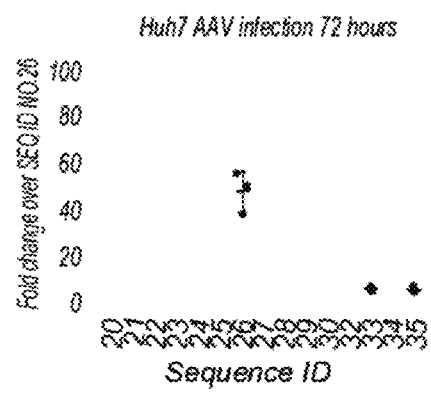
Figure 23C:
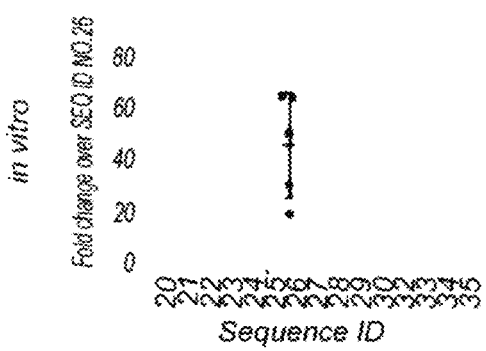
Figure 23D:
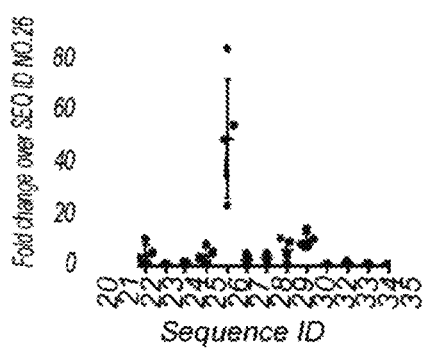
Figure 23E:
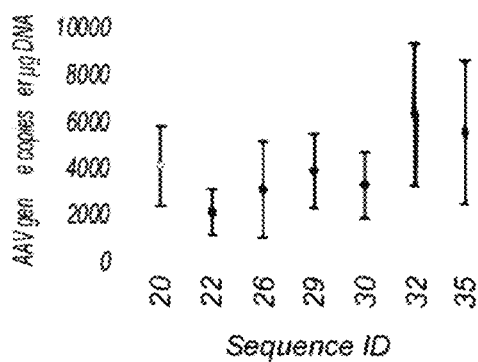
Figure 24B:
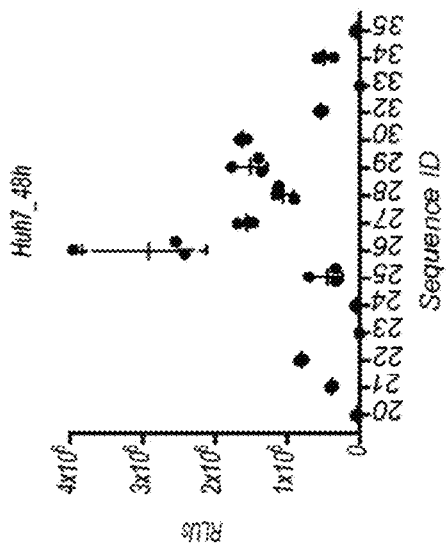
FIG. 24A-D shows transfection of AAV plasmids into cell lines and hpHepatocytes. A. Shows RLUs in HepG2 cells at 48 hrs. B. Shows RLUs in Huh7 cells at 48 hrs. C. Shows RLUs in HepaRG cells at 48 hrs. D. Shows RLUs in hpHepatocytes cells at 48 hrs.
Figure 24D:
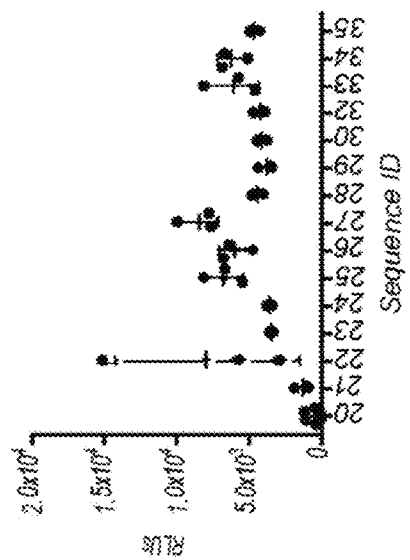
Figure 24A:
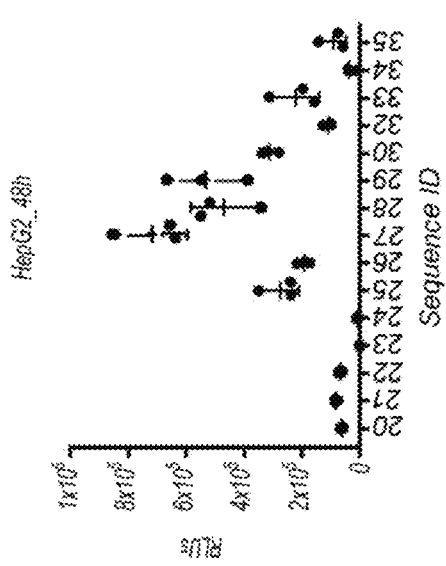
Figure 24C:
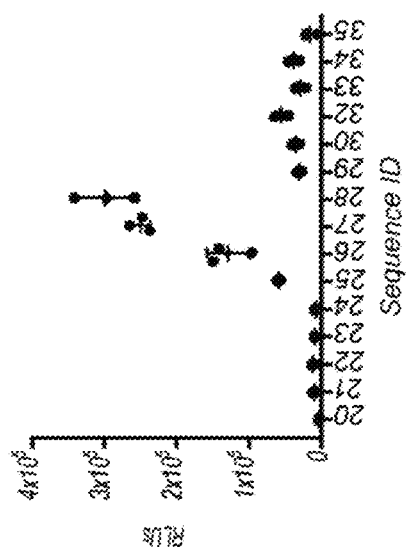

To reduce the size of the promoter sequences generated so far, cloning adaptors and accessory sequences were deleted from the original promoter designs. At the end of the design process, a combination of 16 promoter sequences, including original and size reduced versions were further studied in reporter constructs in an AAV plasmid backbone. These 16 candidates are listed in Table 1, as SEQ ID NOs:21-35, respectively, and include original constructs and size reduced synthetic polynucleotides (all derived from composite promoter sequences and #B4 (SEQ ID NO:32) and #C14 (SEQ ID NO:34) sequences). FIG. 23 shows exemplary results obtained with these constructs. Briefly, FIG. 23A shows data upon in vitro transfection with plasmid DNAs encoding the promoters plus reporter. FIG. 23B shows activity of same promoters+reporter now introduced into cells by AAV infection. FIGS. 23C and 23D show bleeds obtained from mice injected with the AAV vectors after 2 and 6 weeks. FIG. 23E shows the number of AAV genomes per μg DNA in liver 6 weeks after administration of AAV-prom-reporter to mice.

For the purposes of the in vivo experiments, mice were injected with the disclosed synthetic promoter constructs in recombinant AAV2 capsids harboring the expression cassette (SEAP) driven by one of the synthetic promoters. The mice (C57BL/6J) were given tail vein injections of $5 \times 10^{12}$ total genome copies per mouse in groups of five with vehicle as the control group. Blood was collected via facial vein bleeding at week 1, 2, 4 and 6 in-life. At 6 weeks post injection the mice were sacrificed where the liver and a selection of peripheral organs were harvested for biodistribution analysis. SEAP activity analysis was performed on the serum of the mice as per the instructions of the chemi-luminescent SEAP reporter assay kit (Roche).

Figure 25:
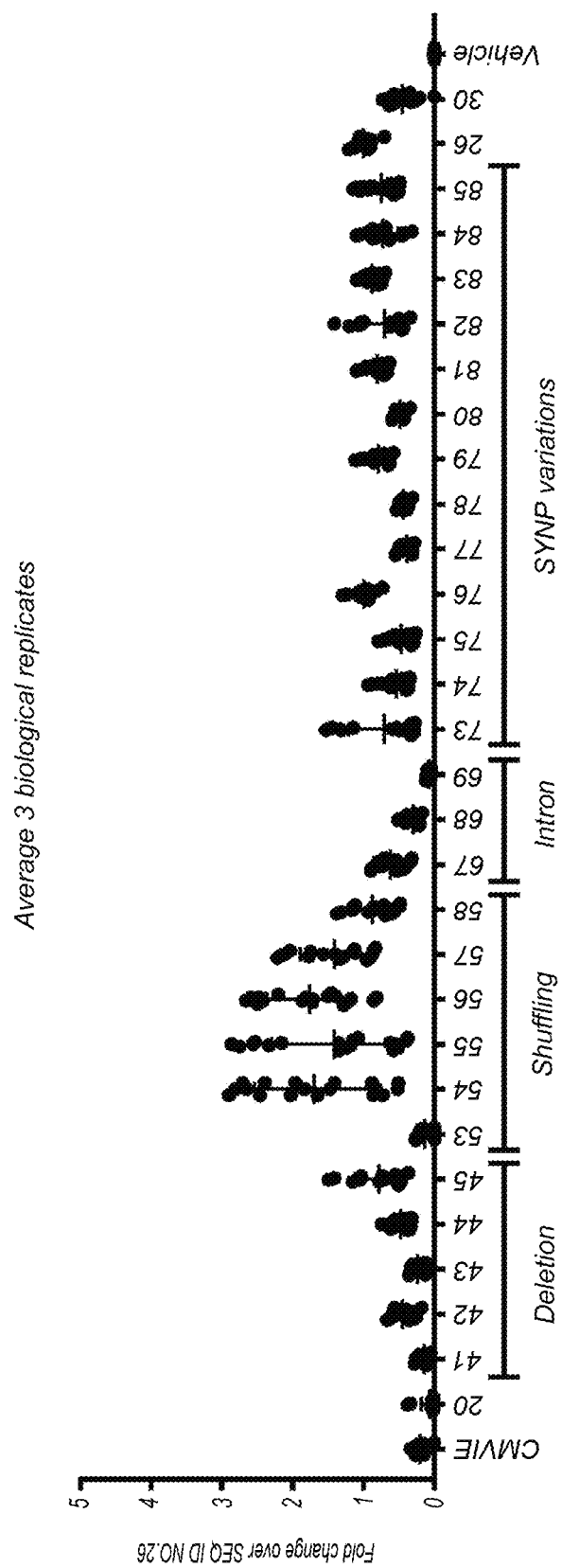
FIG. 25 shows activity of SEQ ID NO:26 derivatives with an average 3 biological replicates. Derivatives and control sequences were screened in Huh7 cells using a standard luciferase assay and promoter activity was normalised to SEQ ID NO:26 promoter to see if the changes made to the original promoter has a positive or negative effect on promoter activity. Transfections were performed in triplicate, luciferase assays were done in duplicate and each plot shows the results from 3 biological replicates.
Figure 26:
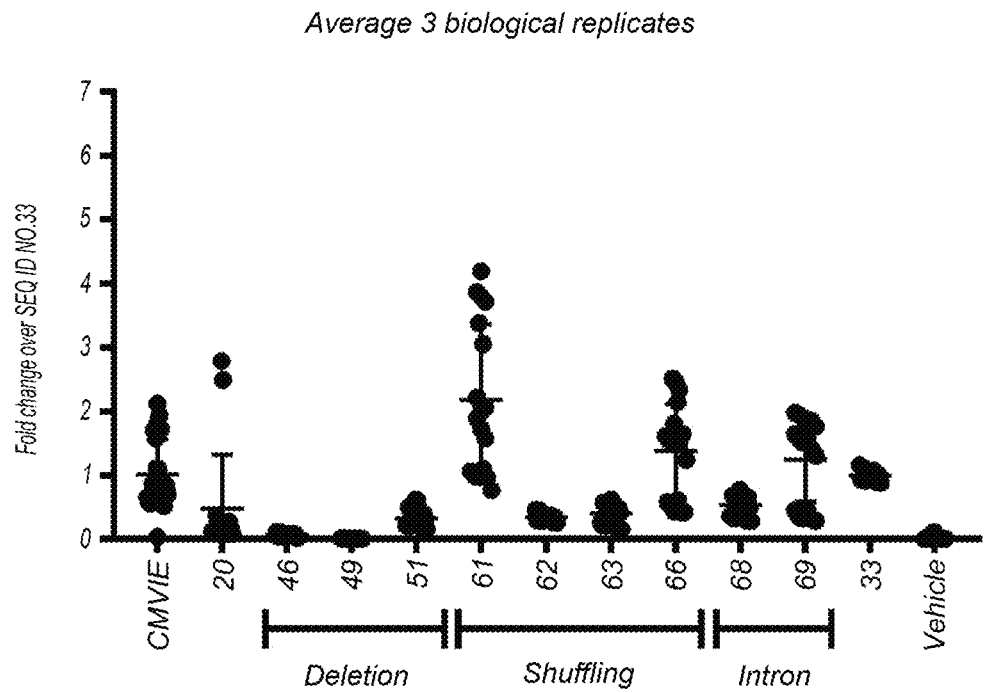
FIG. 26 shows SEQ ID NO:33 derivatives and control sequences were screened in Huh7 cells using a standard luciferase assay and promoter activity was normalized to SEQ ID NO:33 to see if the changes made to the original promoter has a positive or negative effect on promoter activity. Transfections were performed in triplicate, luciferase assays were done in duplicate and each plot shows the results from 3 biological replicates.
Figure 27:
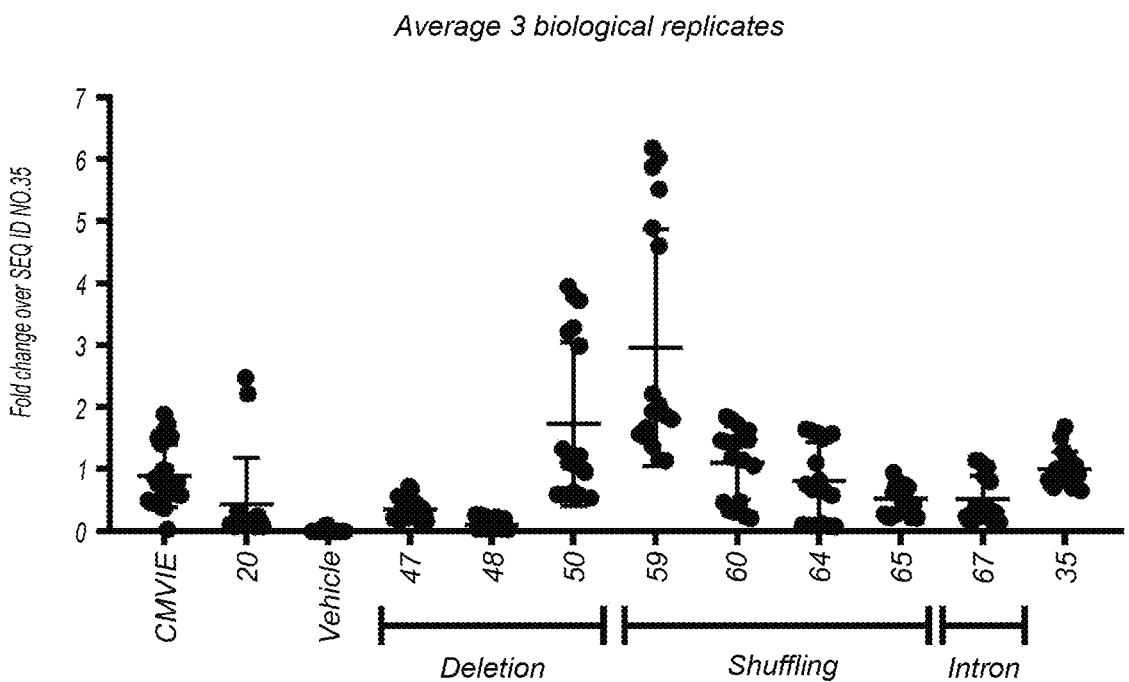
FIG. 27 shows activity of SEQ ID NO:35 derivatives with an average 3 biological replicates. Derivatives and control sequences were screened in Huh7 cells using a standard luciferase assay and promoter activity was normalized to SEQ ID NO:35 promoter to see if the changes made to the original promoter has a positive or negative effect on promoter activity. Transfections were performed in triplicate, luciferase assays were done in duplicate and each plot shows the results from 3 biological replicates.

Further variations that were included were promoter sequences that have promoter elements in reverse orientation, shuffled or deleted. The SEQ ID NO:6 element is a composite element, elements comprised therein were further modified to identify possible further size reduction and/or possible improvements for gene expression in the context of the promoter G6PC_COMP_v1. The further variants are listed in Tables 1 and 2 and correspond to derivatives of SEQ ID NO:26 (G6PC_COMP_v1) (i.e. SEQ ID NOs:41-45, 53-58, 67-69, 73-85) and derivatives of SEQ ID NOs:33 and 35 (i.e. SEQ ID NOs:46-52, 59-66 and 70-72). SEQ ID NOs:41-85 were screened as shown in FIGS. 25-27, which show exemplary results with these constructs. The constructs tested in FIG. 25 were normalized to SEQ ID NO:26 and SEQ ID NO:30 was used as a positive control. The constructs tested in FIG. 26 were normalized to SEQ ID NO:33 and the constructs tested in FIG. 27 were normalized to SEQ ID NO:35.

As said, SEQ ID NO:5 element is a composite element, and elements comprised therein were further modified to identify possible further size reduction and/or possible improvements for gene expression. In addition, deletion of the SEQ ID NO.5 strongly reduced gene expression (See FIG. 29, 01), indicating that this composite element is important for expression. Using the G6PC_COMP_v1 promoter as a starting point, the SEQ ID NO:5 sequence was modified by introducing mutations, introducing deletions, reversing elements, and also comparing it with a larger element in which SEQ ID NO:5 is comprised (SEQ ID NO:100). The larger sequence of SEQ ID NO:100 was found to have the same activity as compared to SEQ ID NO:5 (data not shown). All modifications tested confirmed that SEQ ID NO:5 allows for extensive variation, allowing deletions of spacer elements to reduce the size even further, and also allowing mutations of elements comprised in SEQ ID NO:5 as well as reversing elements comprised therein as well. Hence, it appears that extensive modifications of SEQ ID NO:5 are allowed, thereby confirming that this sequence represents a composite element and that is not required to maintain a full-length sequence thereof, but that it can also be divided in further elements, while still contributing to liver specific gene expression. Judging from the in vitro experiments, the first 2 nucleotides of SEQ ID NO:5 do not appear to be important, as well as the last 3 nucleotides, and these may be further deleted from SEQ ID NO:5, while retaining substantially the same activity as a promoter comprising SEQ ID NO:5. The spacer sequence of 10 nucleotides comprised in SEQ ID NO:5 also results in the promoter having substantially the same activity. Deletion of these sequences combined reduces the size further while maintaining activity (i.e. ending up with a 51 nucleotide sequence). Moreover, functional elements comprised in SEQ ID NO:5 of the liver specific promoter can be reversed, and modified as well, which indicates that these elements are not be required to be oriented in the same way and are not required to be in each other's proximity. Hence, based on the results, a preferred G6PC_COMP_v1 promoter, or any variant thereof, can be defined to include one or more of SEQ ID NO:101 (ACTTAGCCCCTGTTTGCTCCTCCG), and SEQ ID NO:102 (TGACCTTGGTTAATATTCACCAGC), preferably SEQ ID NO:101 and SEQ ID NO:102. It is understood that such a liver specific promoter may also comprise variants of SEQ ID NO:101 and/or SEQ ID NO:102, or the reverse complement of one or both thereof. Hence, wherever in the description herein SEQ ID NO:5 is included in a liver specific promoter, alternatively to SEQ ID NO:5, said promoter can be defined to include SEQ ID NO:101 and/or SEQ ID NO:102, or a functional equivalent to SEQ ID NO:101 and/or SEQ ID NO:102.

Furthermore, as also shown in FIG. 26, many of the variants made of SEQ ID NO:5 results in promoters having very similar activity as compared to SEQ ID NO:5, albeit slightly reduced, while still retaining substantial improvement of activity as compared with LP1. Hence, a variant of the composite element of SEQ ID NO:5 can be defined as composite element comprising SEQ ID NO:101 and a sequence selected from the group consisting of SEQ ID NO:102, SEQ ID NO:104 (TGGTTAATATTCACCAGC), SEQ ID NO:106 (TGACCTTGGTTAATATTCACCA); or a composite element comprising SEQ ID NO:103 (CCCTGTTTGCTCCTCCG) and a sequence selected from the group consisting of SEQ ID NO:102, SEQ ID NO:104 (TGGTTAATATTCACCAGC), SEQ ID NO:106 (TGACCTTGGTTAATATTCACCA); or a composite element comprising SEQ ID NO:105 (CCCTGTTTGCTCC) and sequence TCCG, and a sequence selected from the group consisting of SEQ ID NO:102, SEQ ID NO:104 (TGGTTAATATTCACCAGC), SEQ ID NO:106 (TGACCTTGGTTAATATTCACCA); or a composite element comprising SEQ ID NO:105 and sequence TTAG, and a sequence selected from the group consisting of SEQ ID NO:102, SEQ ID NO:104 (TGGTTAATATTCACCAGC), SEQ ID NO:106 (TGACCTTGGTTAATATTCACCA); or a composite element comprising SEQ ID NO:107 (CCCTATTTACTCC) and sequence TCCG, and a sequence selected from the group consisting of SEQ ID NO:102, SEQ ID NO:104 (TGGTTAATATTCACCAGC), SEQ ID NO:106 (TGACCTTGGTTAATATTCACCA); or a composite element comprising SEQ ID NO:107 and sequence TTAG, and a sequence selected from the group consisting of SEQ ID NO:102, SEQ ID NO:104 (TGGTTAATATTCACCAGC), SEQ ID NO:106 (TGACCTTGGTTAATATTCACCA). It is understood that said composite element preferably has a sequence length which is less than 60 nucleotides. It is understood that the components of the composite elements may also be the reverse complementary sequence thereof instead, as it is shown in the examples.

Activity of modified promoters remained more active over LP1, some modification reduced activity as compared with the original constructs, whereas some modifications improved higher activity even further. Deletion of elements had a more pronounced impact on activity, which supports the combinatorial effect of the elements rather than the strength of individual elements.

Example 13—Testing of AAV Constructs in Primary Human Hepatocytes

Reporter constructs were screened not just by infection in human primary hepatocytes but also in Huh-7, HepG2 and HepaRG. Reporter constructs were assessed by transfection to check the correlation of the promoter activity in the context of plasmid backbone versus AAV genome. SEAP was used as a reporter.

In the transfection experiments, SEAP was assayed 48 hours after transfection. SEAP activity was assayed after 24, 48 and/or 72 hours of infection in some of the cell lines to optimize the timing of the assay; results showed perfect correlation independently of the time when the assay was performed.

Transfection reporter constructs: promoter candidates were synthesized at GeneArt and cloned into pVDX vector (UNQ). Reporter constructs were tested by transfection in Huh7, HepG2 and HepaRG cells. SEQ ID Nos: 23 and 24 show lower activity than LP1 in all the cell lines tested (FIG. 24). This is expected, because these promoters are derived from the original COMP fragment, made up of regulatory elements shown to be liver specific, but lacking a canonical minimal promoter sequence in its 3' end. The rest of reporter constructs show comparable or higher activity than LP1 in all the cells lines tested. SEQ ID Nos: 27 and 28 were among the best performers in all the cell lines tested. In human primary hepatocytes all the reporter constructs tested by transfection showed higher activity than LP1 (FIG. 24).

Transduction by AAV: UNQ produced viral preps (AAV2 serotype) for the mice study that were also tested in in Huh7, HepaRG and human primary hepatocytes (MOI $10^5$ AAV genomes/cell). HepaRG and human primary hepatocytes proved very difficult to transduce by AAV infection in the assayed conditions.

When tested in the context of the AAV genome, an increase in performance of some of the promoter candidates was observed. This effect was quite dramatic in the case of promoter G6PC_COMP_v1 (SEQ ID NO:26) when compared to the results from transfection experiments using a standard luciferase reporter plasmid (pGL4.10 from Promega and SYNP reporter vector). In previous transfection experiments in Huh7 using luciferase as transcriptional reporter and LP1 lacking the SV40 intron as reference, G6PC_COMP_v1 showed approximately 10 times more activity than LP1. When tested by transfection in Huh7 in the context of an AAV backbone, G6PC_COMP_v1 shows more than 50 times the activity of the full version of the LP1 promoter (including the SV40 intron). See FIG. 25 (where SEQ ID NO:20=LP1 and SEQ ID NO:26=G6PC_COMP_v1). Promoter activity tested by transfection of the AAV reporter plasmid and transduction of AAV particles correlates well in Huh7

Reference Example 14—Comparing the Performance of HCR-hAAT, LP1 and HLP Promoters The well-known HCR-hAAT promoter (Nathwani et al. Blood 2006; 107 (7): 2653-2661) and shortened versions thereof including LP1 (Nathwani et al. 2006 supra) and HLP (McIntosh et al. Blood. 2013; 121 (17): 3335-44) were tested in vitro by their ability to drive FVIII protein expression by transfection of Huh-7 cells.

Materials and Methods

Transfection Assays and Cells

Three constructs encoding different codon-optimized FVIII coding sequences (resp. named GD6, GD4 and COSX) were transfected into Huh-7 cells using lipofectamine 3000 reagent. A renilla luciferase plasmid was co-transfected to correct for transfection efficiency. Production of FVIII in the medium was detected by harvesting the supernatant 2 days post-transfection and measuring the antigen levels by ELISA (Affinity Biologicals).

Results

Figure 33:
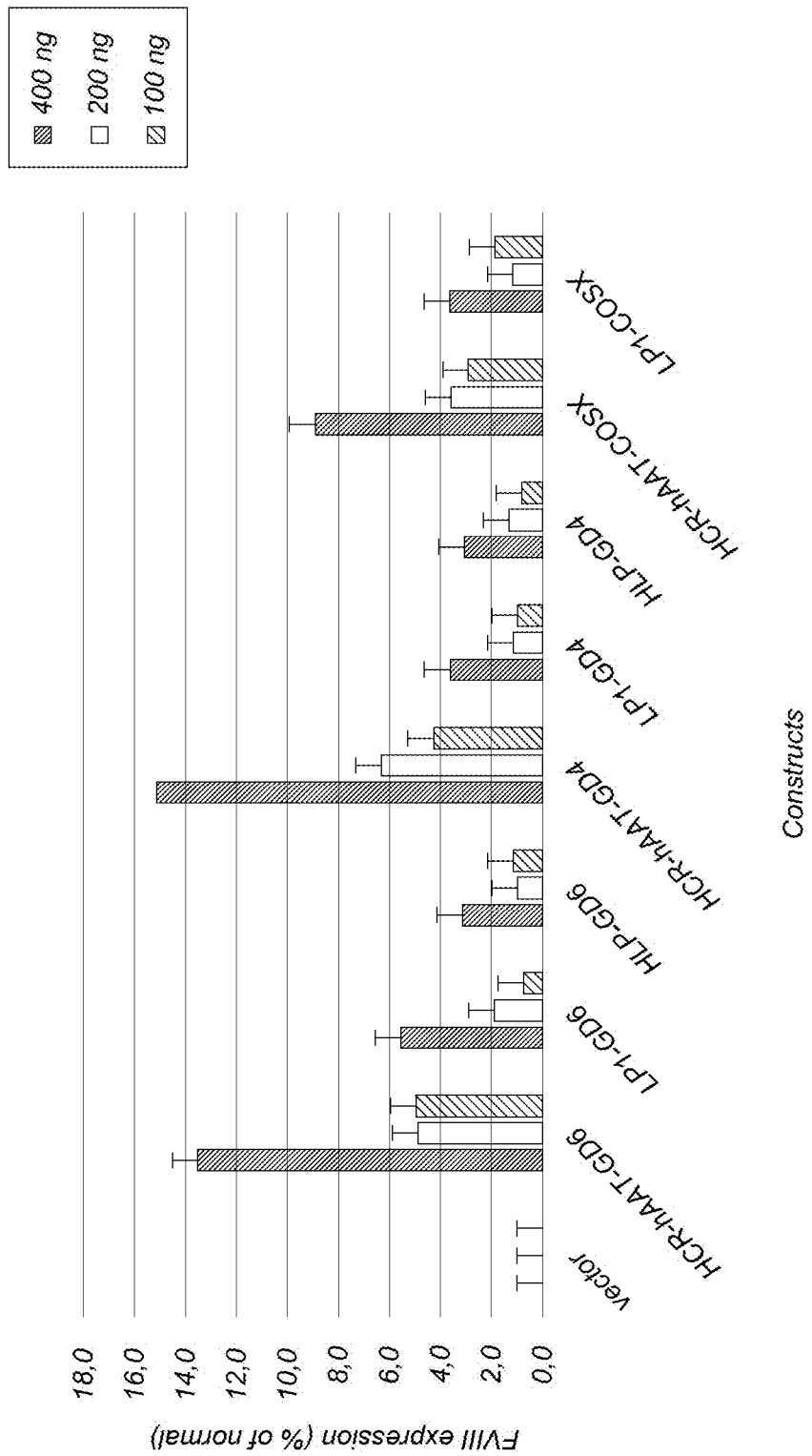
FIG. 33 shows a side-by-side comparison of the HCR-hAAT promoter and its shortened versions, resp. the LP1 and HLP promoters. Three constructs encoding codon-optimized FVIII (named GD6, GD4 and COSX), each driven by the promoter variants as indicated were transfected into Huh-7 cells. Production of FVIII in the medium was detected by harvesting the supernatant 2 days post-transfection and measuring the antigen levels by ELISA (Affinity Biologicals) and corrected for transfection efficiency on the basis of a co-transfected renilla luciferase plasmid.

The potency of the HCR-hAAT promoter was compared with its shortened versions, the LP1 and HLP1 promoters, by transfecting different concentrations of plasmids encoding FVIII driven by the different promoter variants in Huh-7 cells. FVIII protein expression in the supernatant was determined using ELISA. Different codon optimized FVIII constructs were tested that were named GD6, GD4 and COSX. The results in FIG. 33 show that the original sized HCR-hAAT promoter is most efficient in driving FVIII gene expression for all constructs, followed by the LP1 promoter. At least when used at the highest concentration, the LP1 promoter is consistently more potent (GD4 vs GD6) in driving FVIII expression in vitro compared to the HLP promoter.

EQUIVALENTS

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control. Throughout this specification, technical literature is referenced by an author citation, the complete bibliographic details for which are provided below.

The invention claimed is:
1. A synthetic polynucleotide, comprising:
    (a) HNF1/HNF3 (SEQ ID NO:1),
    (b) HNF3/HNF3 (SEQ ID NO:2),
    (c) c/EBP/HNF4 (SEQ ID NO:3),
    (d) HS_CRM2/HNF3 (SEQ ID NO:4), and
    (e) HS_CRM8 (SEQ ID NO:6) or a variant thereof;
or wherein the variant of HS_CRM8 is selected from the group consisting of SEQ ID NO:5, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, and SEQ ID NO:100.

2. The synthetic polynucleotide according to claim 1, comprising at least SEQ ID NO:3 and SEQ ID NO:6 or a variant thereof.

3. The synthetic polynucleotide according to claim 1, wherein the variant of the HS_CRM8 sequence is selected from the group consisting of SEQ ID NO:5, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, and SEQ ID NO:100.

4. The synthetic polynucleotide of claim 1, comprising the five promoter-derived nucleic acids (a)-(e).

5. The synthetic polynucleotide according to claim 4, wherein the synthetic polynucleotide comprises consecutively from the 5' end to the 3'end: SEQ ID NO:1, SEQ ID NO:2, SEQ ID NO:3, SEQ ID NO:4, and SEQ ID NO:6.

6. The synthetic polynucleotide of claim 1, further comprising at least one minimal promoter nucleic acid.

7. The synthetic polynucleotide according to claim 6, wherein the minimal promoter nucleic acid is derived from SERPINE1 (SEQ ID NO:7), SERPINA1 (SEQ ID NO:8), APOC2 (SEQ ID NO:9), or G6PC (SEQ ID NO:10).

8. The synthetic polynucleotide according to claim 7, wherein the minimal promoter nucleic acid comprises a sequence selected from the group consisting of: SEQ ID NOs: 7, 8, 9 and 10.

9. The synthetic polynucleotide of claim 7, wherein the transgene encodes AAT, AGXT, ARG, ASL, ASS, ATP7B, BCKDHA, BCKDHB, CFH, CFTF, CPS, DBT, FAH, FIX, FVIII, HAMP, HFE, JH, MUT, NAGS, OTC, PCCA, PCCB, PI, SLC40A1, TFR2, TTR, UGT1A1, Urokinase, or PXBP.

10. The synthetic polynucleotide of claim 1, further comprising at least one of:
    (i) at least one spacer nucleic acid located between two of the promoter-derived nucleic acids; and,
    (ii) an operably linked nucleic acid sequence encoding an intron.

11. The synthetic polynucleotide of claim 10, wherein the intron is derived from SV40.

12. The synthetic polynucleotide of claim 1, wherein the synthetic polynucleotide is less than 250 base pairs in length.

13. The synthetic polynucleotide of claim 12, wherein the polynucleotide is less than 250 base pairs in length.

14. The synthetic polynucleotide of claim 1, wherein the polynucleotide has a sequence selected from the group consisting of SEQ ID NOs: 21, 22, 23, 24, 25, 26, 27, 28, 29, 30, 31, 41-45, 53-58, 67-69 and 73-86.

15. The synthetic polynucleotide of claim 1, wherein:
    (i) the synthetic polynucleotide promotes liver-specific transgene expression in the liver,
    (ii) the synthetic polynucleotide is suitable for promoting liver-specific transgene expression at a level at least 1.5 fold greater than an LP1 promoter,
    (iii) the synthetic polynucleotide has a reduced transgene expression at a level of at least 4 fold less than a CMV promoter in non-liver derived A549 cells,
    (iv) the synthetic polynucleotide is suitable for promoting liver-specific transgene expression at a level at least 1.5 fold greater than a CMV promoter in liver-derived cells, or
    (v) the synthetic polynucleotide has reduced transgene expression at a level of at least 1.5 fold less than an LP1 promoter in non-liver derived cells.

16. The synthetic polynucleotide of claim 1, further comprising at least one of:
    (i) an operably linked nucleic acid sequence encoding a post-transcriptional regulatory element;
    (ii) an operably linked nucleic acid sequence encoding polyA element; and,
    (iii) an operably linked transgene.

17. An expression cassette comprising a synthetic polynucleotide according to claim 1 and an operably linked polynucleotide sequence encoding a transgene, wherein the transgene encodes a therapeutic polypeptide suitable for use in treating a disease or condition associated with the liver.

18. The expression cassette according to claim 17, further comprising at least one of:
    (i) a nucleic acid encoding a posttranscriptional regulatory element; and,
    (ii) a nucleic acid encoding a polyA element.

19. A gene therapy vector comprising the synthetic polynucleotide of claim 1.

20. The gene therapy vector according to claim 1, wherein the vector is a retroviral vector, a lentiviral vector, an adenoviral vector, or an adeno-associated viral vector (AAV).

21. The gene therapy vector of claim 20, wherein the vector is an AAV is selected from the group consisting of AAV2, AAV5, AAV6, AAV7, AAV8, AAV9, AAV6.2, AAVrh.64R1, AAVhu.37, AAVrh.8, AAVrh.32.33, AAV3B, and LK03.

22. A recombinant viral particle comprising the synthetic polynucleotide of claim 1.

* * * * *